(12) United States Patent
Šikšnys et al.

(10) Patent No.: US 12,123,031 B2
(45) Date of Patent: Oct. 22, 2024

(54) REGULATION OF CRISPR-ASSOCIATED ROSSMAN FOLD (CARF) DOMAIN CONTAINING PROTEINS BY OLIGOADENYLATES

(71) Applicant: VILNIUS UNIVERSITY, Vilnius (LT)

(72) Inventors: Virginijus Šikšnys, Vilnius (LT); Migle Kazlauskiene, Vilnius (LT); Georgij Kostiuk, Vilnius (LT); Gintautas Tamulaitis, Vilnius (LT)

(73) Assignee: VILNIUS UNIVERSITY, Vilnius (LT)

( * ) Notice: Subject to any disclaimer, the term of this patent is extended or adjusted under 35 U.S.C. 154(b) by 1272 days.

(21) Appl. No.: 16/618,238

(22) PCT Filed: May 31, 2018

(86) PCT No.: PCT/IB2018/053906
§ 371 (c)(1),
(2) Date: Nov. 29, 2019

(87) PCT Pub. No.: WO2018/220583
PCT Pub. Date: Dec. 6, 2018

(65) Prior Publication Data
US 2021/0130799 A1 May 6, 2021

Related U.S. Application Data

(60) Provisional application No. 62/512,868, filed on May 31, 2017.

(51) Int. Cl.
| C12N 9/22 | (2006.01) |
| C12N 9/12 | (2006.01) |
| C12P 19/34 | (2006.01) |
| C12Q 1/6811 | (2018.01) |

(52) U.S. Cl.
CPC .............. *C12N 9/22* (2013.01); *C12N 9/1241* (2013.01); *C12P 19/34* (2013.01); *C12Q 1/6811* (2013.01); *C12Y 207/07* (2013.01); *C12N 2310/20* (2017.05)

(58) Field of Classification Search
CPC .... C12N 9/22; C12N 9/1241; C12N 2310/20; C12P 19/34; C12Q 1/6811; C12Y 207/07; C07H 21/00
See application file for complete search history.

(56) References Cited

PUBLICATIONS

Fujimoto, M. et al., "Identity of Phosphodiesterase and Phosphomonesterase Activities with Nuclease P1 (a Nuclease from Penicillium citrinum)," Agricultural and Biological Chemistry, 38:4, 785-790, 1974.
Fujimoto, M. et al., "Substrate Specificity of Nuclease P1," Agricultural and Biological Chemistry, 38:9, 1555-1561, 1974.
Genschik, P. et al., "Characterization of the *Escherichia coli* RNA 3'-Terminal Phosphate Cyclase and Its σ54-Regulated Operon," The Journal of Biological Chemistry, vol. 273, No. 39, Sep. 25, 1998, pp. 25516-25526.
Makarova, K. et al., "A DNA repair system specific for thermophilic Archaea and bacteria predicted by genomic context analysis," Nucleic Acids Research, 2002, vol. 30, No. 2, pp. 482-496.
Yoshioka, K., "Ky-Plot—A User-oriented Tool for Statistical Data Analysis and Visualization," Computational Statistics (2002) 17:425-437.
Pedersen, K., et al., "The Bacterial Toxin RelE Displays Codon-Specific Cleavage of mRNAs in the Ribosomal A Site," Cell, vol. 112, 131-140, Jan. 10, 2003.
Kubota, K. et al., "Identification of 2'-Phosphodiesterase, Which Plays a Role in the 2-5A System Regulated by Interferon," The Journal of Biological Chemistry, vol. 278, No. 36, Sep. 3, 2004, pp. 37832-37841.
Zheng, L. et al., "An efficient one-step site-directed and site-saturation mutagenesis protocol," Nucleic Acids Research, 2004, vol. 32, No. 14, e115.
Makarova, K. et al., "A putative RNA-interference-based immune system in prokaryotes: computational analysis of the predicted enzymatic machinery, functional analogies with eukaryotic RNAi, and hypothetical mechanisms of action," Biology Direct 2006, 1:7.
Silverman, R., "A scientific journey through the 2-5A/RNase L system," Cytokine & Growth Factor Reviews 18 (2007) 381-388.
Andreev, D. et al., "The bacterial toxin RelE induces specific mRNA cleavage in the A site of the eukaryote ribosome," RNA (2008), 14:233-239.
Zhang, B., et al., "An easy-to-use site-directed mutagenesis method with a designed restriction site for convenient and reliable mutant screening," Journal of Zhejiang University Science B 2009 10(6):479-482.
Goldman, S. et al., "NanoRNAs Prime Transcription Initiation In Vivo," Molecular Cell 42, 817-825, Jun. 24, 2011.
Lintner, N. et al., "The Structure of the CRISPR-Associated Protein Csa3 Provides Insight into the Regulation of the CRISPR/Cas System," Journal of Molecular Biology (2011) 405, 939-955.
Makarova, K. et al., Unification of Cas protein families and a simple scenario for the origin and evolution of CRISPR-Cas systems, Biology Direct 2011, 6:38.
Makarova, K. et al., "Evolution and classification of the CRISPR-Cas systems," Nature Reviews Microbiology, 2011, pp. 1-11.
Poulsen, J. et al., "Human 2'-phosphodiesterase localizes to the mitochondrial matrix with a putative function in mitochondrial RNA turnover," Nucleic Acids Research, 2011, vol. 39, No. 9, Jan. 17, 2011.
Chakravarty, A. et al., "RNA ligase RtcB splices 3'-phosphate and 5'-OH ends via covalent RtcB-(histidinyl)-GMP and polynucleotide-(3')pp(5')G intermediates," 6072-6077, PNAS, Apr. 17, 2012, vol. 109, No. 16.

(Continued)

*Primary Examiner* — Elly-Gerald Stoica
(74) *Attorney, Agent, or Firm* — NIXON & VANDERHYE

(57) ABSTRACT

A method of synthetizing cyclic oligoadenylates using a novel catalytic activity of a protein possessing the Palm domain, such as the Cas10 protein, and using such compounds for activation of proteins possessing the CARF doman, such as the Csm6 protein.

8 Claims, 29 Drawing Sheets

Specification includes a Sequence Listing.

(56) References Cited

PUBLICATIONS

Tanaka, N. et al., "RtcB, a Novel RNA Ligase, Can Catalyze tRNA Splicing and HAC1 mRNA Splicing in Vivo," The Journal of Biological Chemistry, vol. 286, No. 35, pp. 30253-30257, Sep. 2, 2011.

Wiedenheft, B. et al., "RNA-guided genetic silencing systems in bacteria and archaea," Nature, vol. 482, pp. 331-338, Feb. 16, 2012.

Zhu, X. et al., "Crystal structure of Cmr2 suggests a nucleotide cyclase-related enzyme in type III CRISPR-Cas systems," FEBS Letters, Mar. 1, 2012.

Anantharaman, V. et al., "Comprehensive analysis of the HEPN superfamily: identification of novel roles in intra-genomic conflicts, defense, pathogenesis and RNA processing," Biology Direct 2013, 8:15.

Corrigan, R. et al., "Cyclic di-AMP: another second messenger enters the fray," Nature Reviews Microbiology, vol. 11, Aug. 2013, pp. 513-524.

Danilchanka, O. et al., "Cyclic Dinucleotides and the Innate Immune Response," Cell 154, Aug. 29, 2013, pp. 962-970.

Kim, Y. et al., "Crystal structure and nucleic acid-binding activity of the CRISPR-associated protein Csx1 of Pyrococcus furiosus," Proteins 2013; 81:261-270.

Koonin, E. et al., "CRISPR-CAS Evolution of an RNA-based adaptive immunity system in prokaryotes," RNA Biology 10:5, 679-686, May 2013.

Osawa, T. et al., "Crystal Structure of the Cmr2-Cmr3 Subcomplex in the CRISPR-Cas RNA Silencing Effector Complex," J. Mol. Biol. (2013) 425, 3811-3823.

Xiao, T. et al., "The cGAS-Sting Pathway for DNA Sensing," Molecular Cell 51, Jul. 25, 2013, pp. 135-139.

Goldberg, G. et al., "Conditional tolerance of temperate phages via transcription-dependent CRISPR-Cas targeting," Nature vol. 514, Oct. 30, 2014.

Hatoum-Aslan, A. et al., "Genetic Characterization of Antiplasmid Immunity through a Type III-A CRISPR-Cas System," Journal of Bacteriology, vol. 196, No. 2, Jan. 2014, pp. 310-317.

Makarova, K. et al., "CARF and WYL domains: ligand-binding regulators of prokaryotic defense systems," Frontiers in Genetics: Bioinformatics and Computational Biology, vol. 5, Article 102, Apr. 2014, pp. 1-9.

Tamulaitis, G. et al., "Programmable RNA Shredding by the Type III-A CRISPR-Cas System of *Streptococcus thermophilus*," Molecular Cell 56, Nov. 20, 2014, pp. 1-12.

Poulsen, J. et al., "Enzyme assays for synthesis and degradation of 2-5As and other 2'-5' oligoadenylates," BMC Biochemistry (2015) 16:15.

Samai, P. et al., "Co-transcriptional DNA and RNA Cleavage during Type III CRISPR-Cas Immunity," 2015, Cell 161, 1-11.

Cao, L. et al., "Identification and functional study of type III-A CRISPR-Cas systems in clinical isolates of *Staphylococcus aureus*," International Journal of Medical Microbiology, 2016.

Elmore, J. et al., "Bipartite recognition of target RNAs activates DNA cleavage by the Type III-B CRISPR-Cas system," Genes & Development 30:1-13, 2015.

Engl, C. et al., "Cellular and molecular phenotypes depending upon the RNA repair system RtcAB of *Escherichia coli*," Nucleic Acids Research, 2016, vol. 44, No. 20, 9933-9941.

Estrella, M. et al., "RNA-activated DNA cleavage by the Type III-B CRISPR-Cas effector complex," Genes & Development 30:1-11, 2016.

Han, W. et al., "A type III-B CRISPR-Cas effector complex mediating massive target DNA destruction," Nucleic Acids Research, 2016, pp. 1-11.

Jiang, W. et al., "Degradation of Phage Transcripts by CRISPR-Associated RNases Enables Type III CRISPR-Cas Immunity," 2016, Cell 164, 1-12.

Kazlauskiene, M. et al., "Spatiotemporal Control of Type III-A CRISPR-Cas Immunity: Coupling DNA Degradation with the Target RNA Recognition," 2016, Molecular Cell 62, 295-306.

Niewoehner, O. et al., "Structural basis for the endoribonuclease activity of the type III-A CRISPR-associated protein Csm6," RNA 22:1-12, 2016.

Opoku-Temeng, C. et al., "Cyclic dinucleotide (c-di-GMP, c-di-AMP, and cGAMP) signalings have come of age to be inhibited by small molecules," Chem. Commun. 2016, 52, 9327.

Page, R. et al., "Toxin-antitoxin systems in bacterial growth arrest and persistence," Nature Chemical Biology, vol. 12, Apr. 2016, pp. 208-214.

Sheppard, N. et al., "The CRISPR-associated Csx1 protein of Pyrococcus furiosus is an adenosine-specific endoribonuclease," RNA 22:1-9, 2016.

Gootenberg, J. et al., "Nucleic acid detection with CRISPR-Cas13a/C2c2," Science, Apr. 13, 2017.

Cocozaki, A. et al., "Structure of the Cmr2 Subunit of the CRISPR-Cas RNA Silencing Complex," Structure 20, 545-553, Mar. 7, 2012.

Kazlauskiene, M. et al., "A cyclic oligonucleotide signaling pathway in type III CRISPR-Cas systems," Science 357, 605-609 (2017).

Liu, T. et al., "RNA and DNA Targeting by a Reconsituted Thermus thermophiles Type III-A CRISPR-Cas System," PLos One 12(1): e0170552, 2017.

Niewoehner, O. et al., "Type III CRISPR-Cas systems produce cyclic oligoadenylate second messengers," Nature, Aug. 31, 2017, vol. 548.

Tamulaitis, G. et al., "Type III CRISPR-Cas Immunity: Major Differences Brushed Aside," Trends in Microbiology 1381, 2017.

FIGS. 1A, B, C, D, and E

FIGS. 2A, B, C, D and E

FIGS. 3A and B

FIGS. 4A, B, C, and D

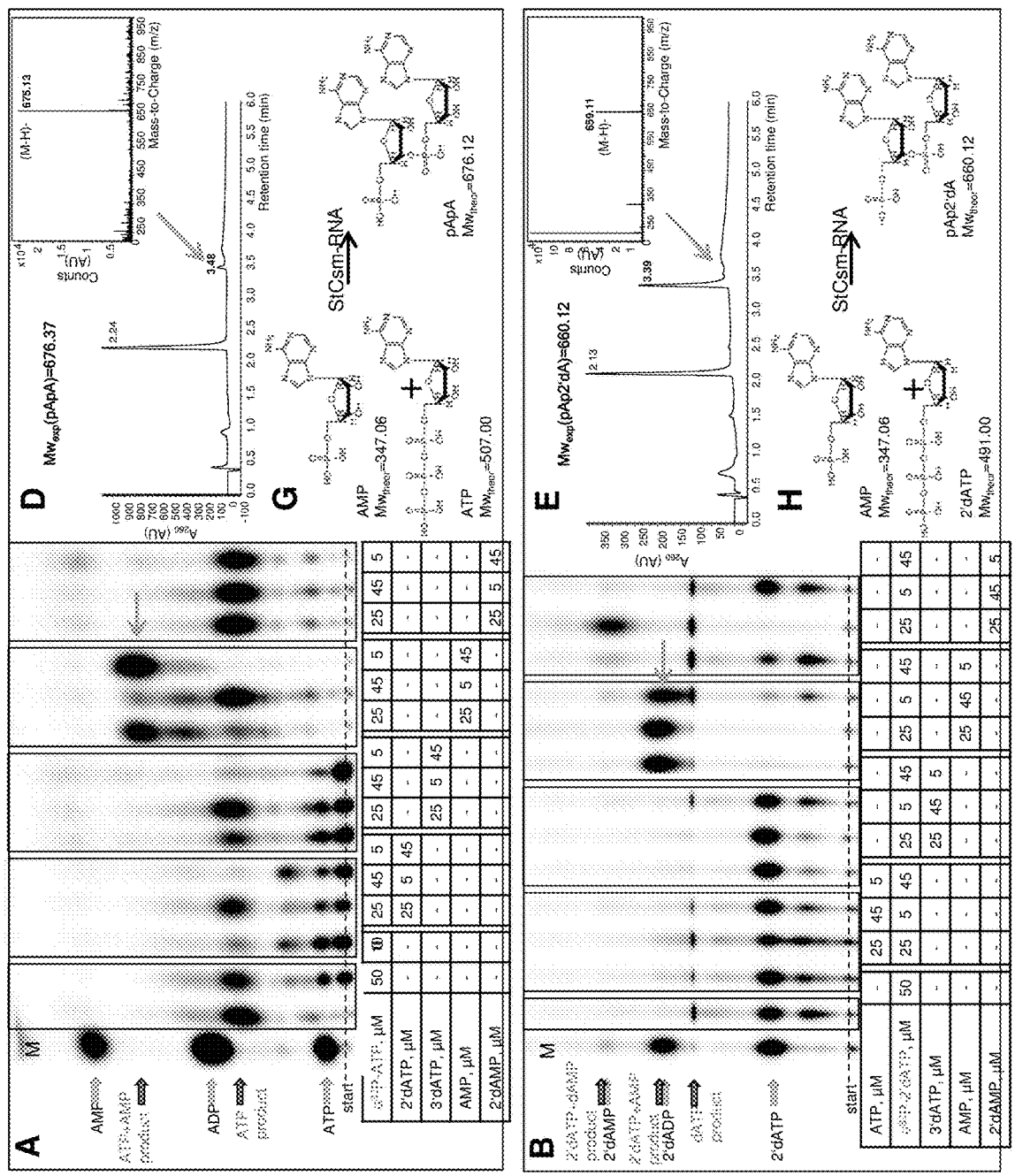
FIGS. 8A, B, D, G, E, H

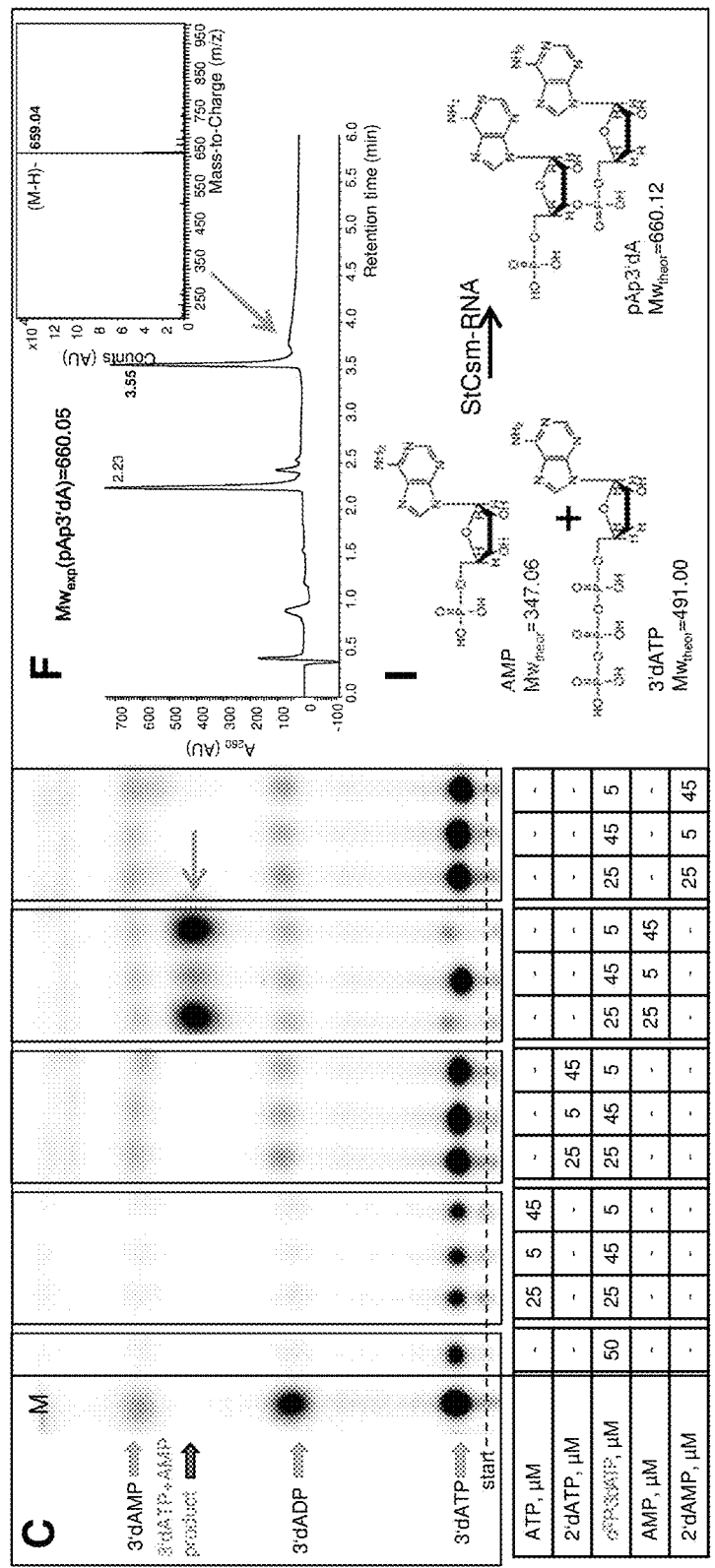
FIGS. 8C, F, I

FIGS. 9A, B and C
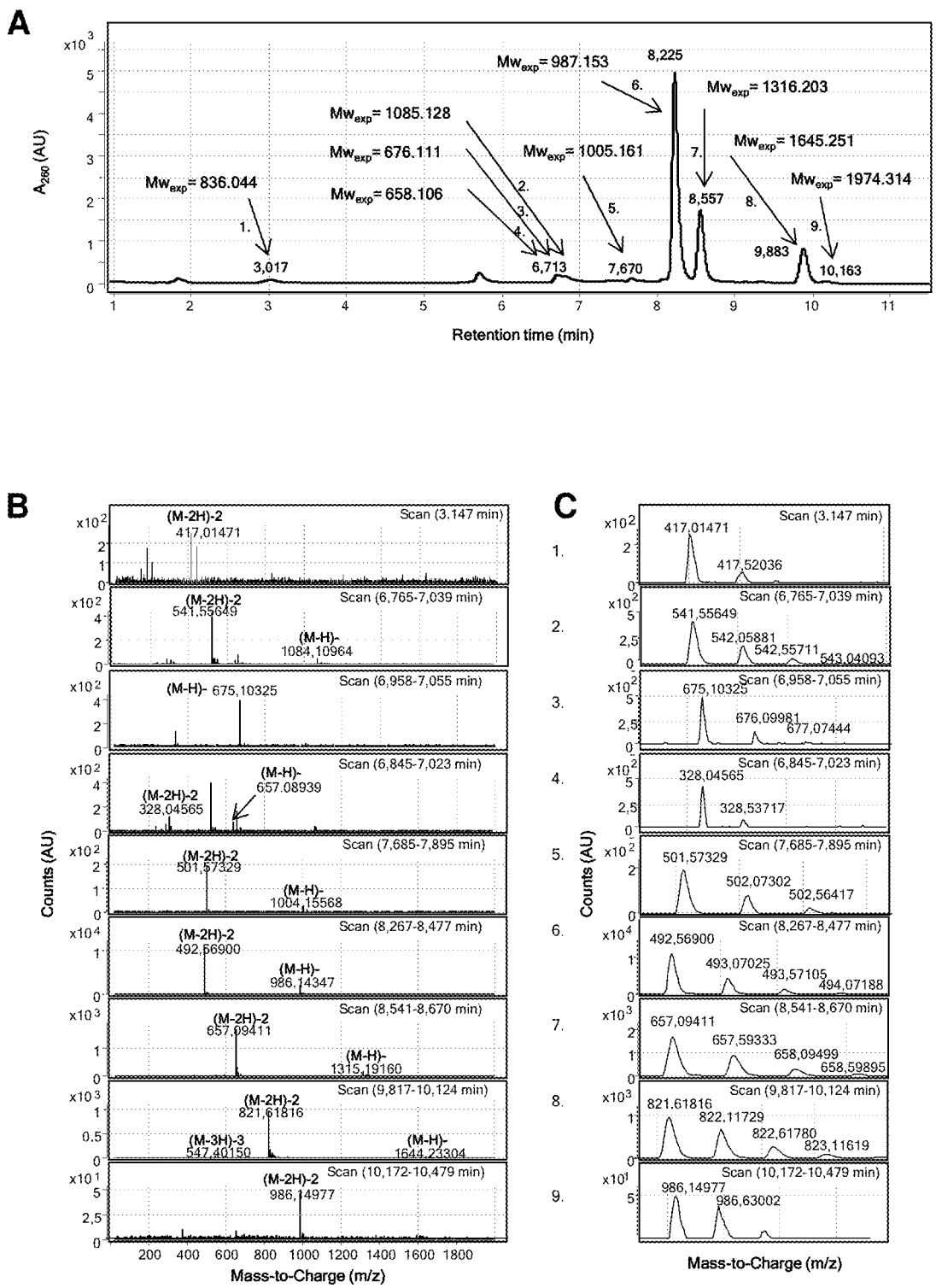

| | t, min | Observed experimental m/z | | | Mw. exp.calc. | Mw. theoretical | Composition, % | Putative compound |
|---|---|---|---|---|---|---|---|---|
| | | (M-H)- | (M-2H)-2 | (M-3H)-3 | | | | |
| 1 | 3.02 | | 417.015 | | 836.044 | 836.048 | 4.0 | pppApA or ppApAp or pApApp or ApAppp |
| 2 | 6.71 | 1084.110 | 541.557 | | 1085.128 | 1085.128 | 5.2 | ppApApA or pApApAp or ApApApp |
| 3 | 6.71 | 675.103 | | | 676.111 | 676.116 | | pApA or ApAp |
| 4 | 6.71 | 657.089 | 328.046 | | 658.106 | 658.105 | | c(AMP)₂ or ApA(2',3')>p |
| 5 | 7.67 | 1004.156 | 501.573 | | 1005.161 | 1005.168 | 1.0 | pApApA or ApApAp |
| 6 | 8.23 | 986.143 | 492.569 | | 987.153 | 987.158 | 63.6 | c(AMP)₃ or ApApA(2',3')>p |
| 7 | 8.56 | 1315.192 | 657.094 | | 1316.203 | 1316.210 | 17.7 | c(AMP)₄ or ApApApA(2',3')>p |
| 8 | 9.88 | 1644.233 | 821.618 | 547.402 | 1645.251 | 1645.263 | 8.0 | c(AMP)₅ or ApApApApA(2',3')>p |
| 9 | 10.16 | | 986.150 | | 1974.314 | 1974.315 | 0.5 | c(AMP)₆ or ApApApApApA(2',3')>p |

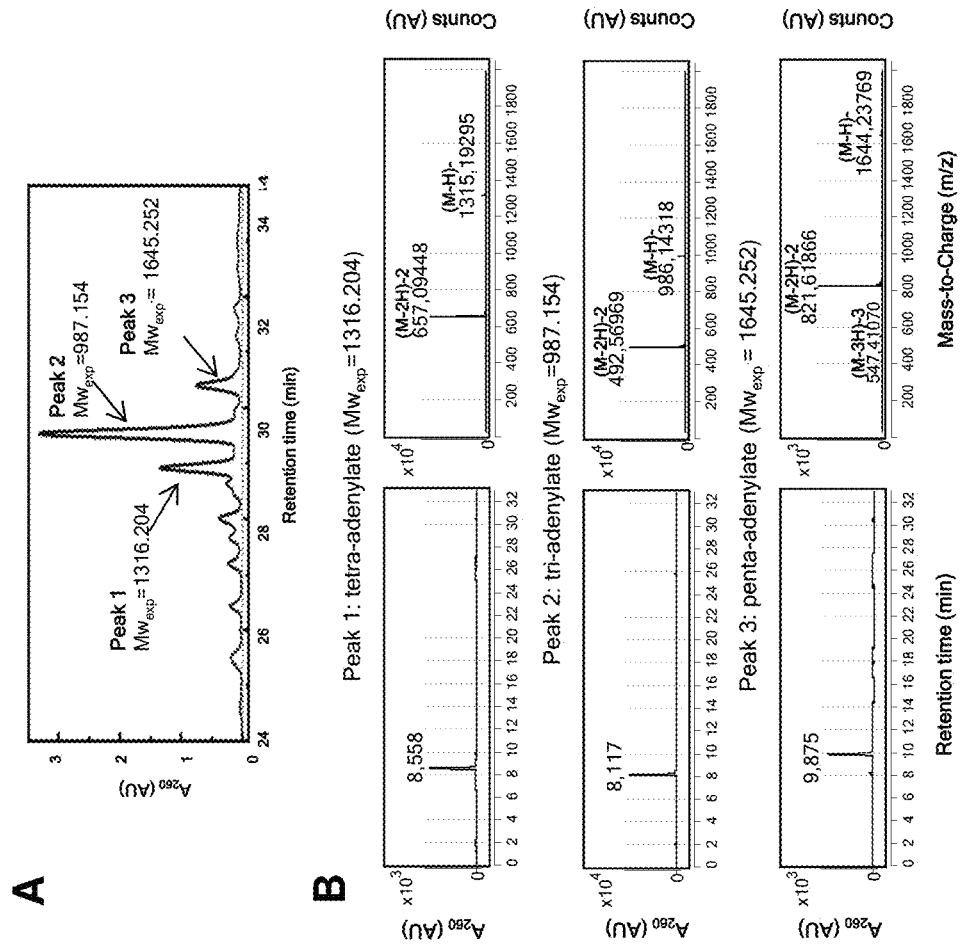
FIGS. 10A and B

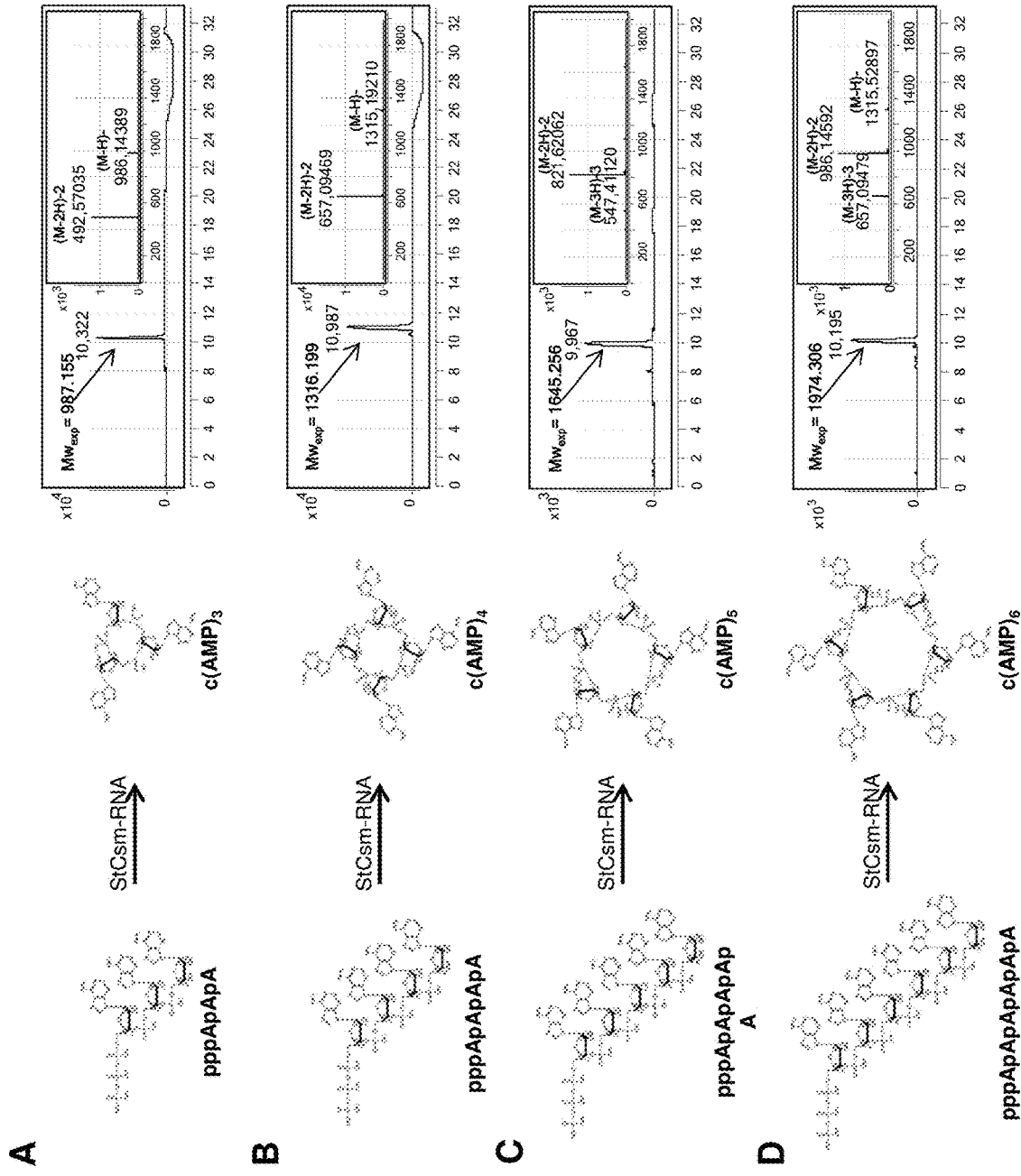
FIGS. 12A, B, C, and D

FIGS. 13A, B, C, and D
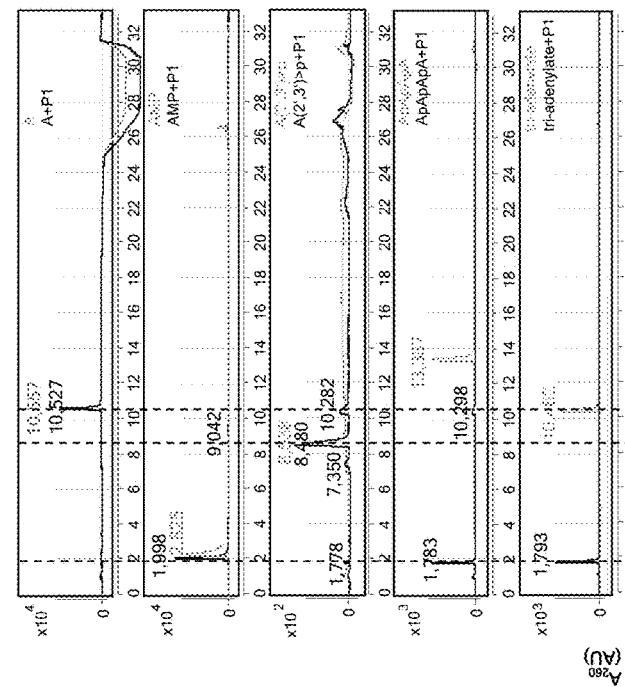
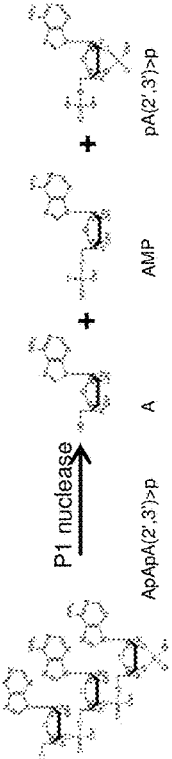

FIGS. 15A and B

FIGS. 16A, B, C, D and E

FIGS. 17A and B

FIGS. 18A and B

FIGS. 19A, B, C, D, E, and F

FIGS. 20A, B, C, D, and E

FIGS. 21A, B, and C

FIGS. 23A and B

FIG. 24A and B

FIGS. 25A, B, C, D and E

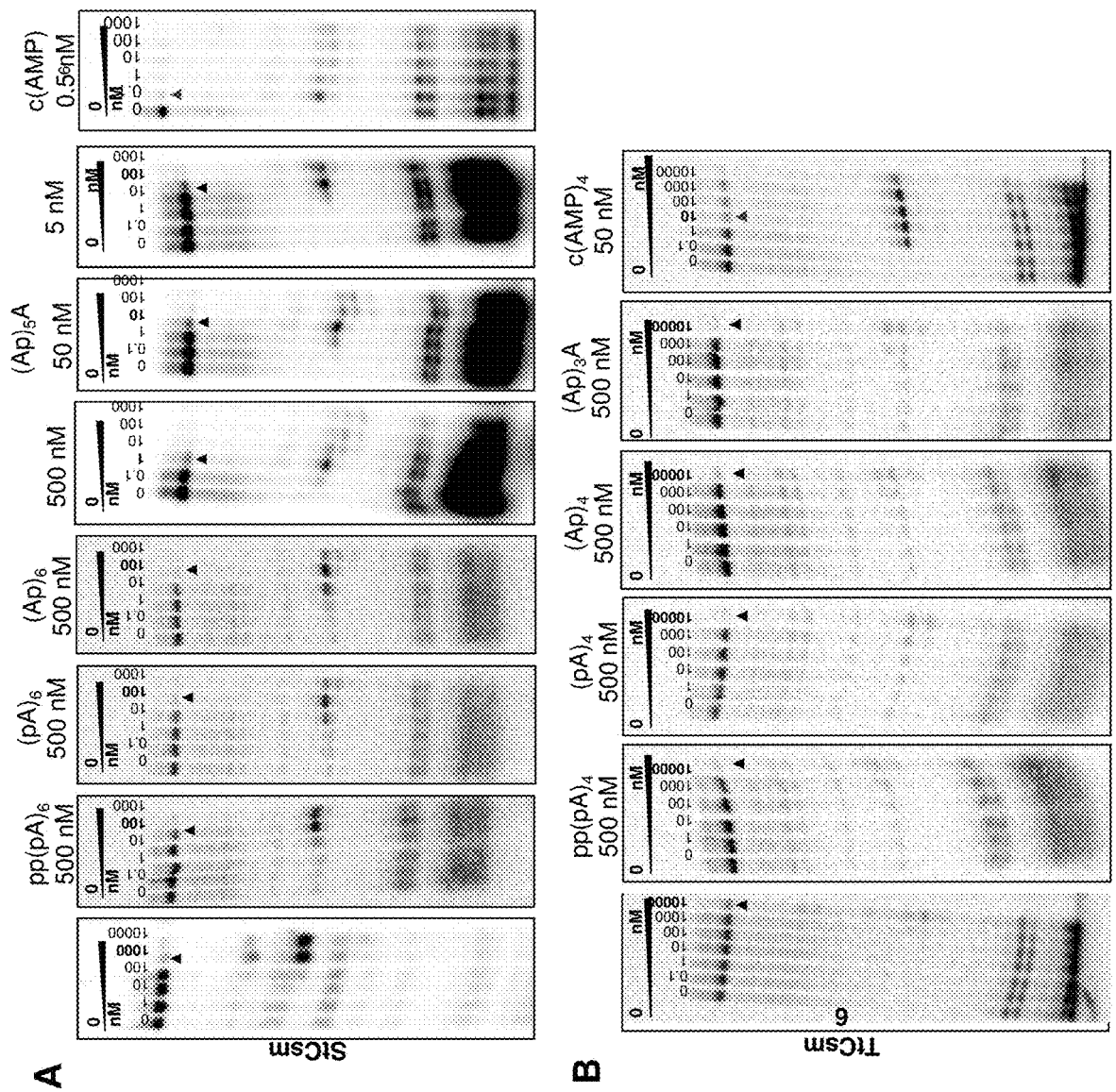
FIGS. 27A and B

REGULATION OF CRISPR-ASSOCIATED ROSSMAN FOLD (CARF) DOMAIN CONTAINING PROTEINS BY OLIGOADENYLATES

INCORPORATION BY REFERENCE

The text file named "ADENYLATES_ST25 (3)" created on May 26, 2020, and sized 19,603 bytes, which contains sequence ID listings, is herein expressly incorporated by reference.

New signal molecules used to allosterically regulate enzymes are disclosed, and a method of synthetizing cyclic oligoadenylates from enzymes possessing the GGDD (SEQ ID NO: 1)-motif and/or their use for activation of proteins possessing CRISPR-Associated Rossmann Fold (CARF) domain. An exemplary enzyme having this GGDD (SEQ ID NO: 1)-motif is Cas10 of the *Streptococcus thermophilus* Type III-A Csm (StCsm) complex. Exemplary enzymes having the CARF domain include StCsm6 and StCsm6' from *Streptococcus thermophilus*, and TtCsm6 from *Thermus thermophilus*.

In one embodiment, the method uses a novel catalytic activity of the Cas10 protein subunit in the target RNA-bound Csm complex of the Type III CRISPR-Cas system to convert adenosine triphosphate (ATP), or linear oligoadenylate triphosphate precursors, to cyclic oligoadenylates which can be used for allosteric activation of CARF family Csm6 ribonuclease. The reaction is shown schematically both below and with additional detail in FIG. 11:

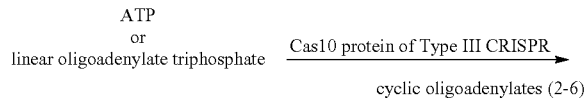

The conversion occurs with >95% efficiency, and in a short reaction time. Cyclic oligoadenylates ranging from 2 to 6 are obtained. Enzymes possessing the Palm domain with a GGDD (SEQ ID NO: 1) motif, such as Csm complexes from other organisms or related Cmr complexes (16), can be used to produce cyclic oligoadenylates. Cas10 protein contains an N-terminal HD-domain, two small α-helical domains, and two Palm domains that share a ferredoxin-like fold with the core domain of nucleic acid polymerases and nucleotide cyclases. Cas10 contains two active sites: the nuclease active site in HD-domain, responsible for target RNA-activated ssDNA hydrolysis, and the GGDD (SEQ ID NO: 1) motif in one of the Palm domains (16-19). The inventors have demonstrated here that GGDD-active site of Cas10 is responsible for adenylate synthesis from ATP or linear oligoadenylate triphosphate precursors.

The method demonstrated, in three Csm6 proteins, that cyclic oligoadenylates act as allosteric regulators of CARF-family Csm6 ribonuclease. This method is shown schematically both below and with additional detail in FIG. 26:

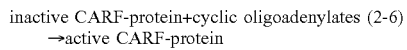

In this method other enzymes possessing the CARF domain can be activated by cyclic oligoadenylates produced by a Cas10-containing complex. The Csm6 CARF-family nuclease is comprised of two domains: CARF family effector domain and HEPN-family ribonuclease domain (30). The core of the CARF domain is a six-stranded Rossmann-like fold with the core strand-5 and strand-6 forming a β-hairpin. The main regions of sequence conservation are associated with strand-1 and strand-4 of the core domain: the end of strand-1 is often characterized by a polar residue, typically with an alcoholic side chain (S/T),whereas immediately downstream of strand-4 is a highly conserved basic residue (K/R) often associated with [DN]X[ST]XXX[RK] signature (SEQ ID NO: 2) (8). CARF domains occur fused not only to RNases but also DNases, membrane-associated protein domains, TIM barrel adenosine deaminase Ada domain (8); more domain combinations are likely to be found. Such proteins could be allosterically regulated by cyclic oligoadenylates or similar compounds, expanding the inventive method to their regulation.

BRIEF DESCRIPTION OF THE FIGURES

FIGS. 8A, B, C, D, E, F, G, H and I show StCsm mediated AMP reaction with ATP, 2'dATP and 3'dATP.

FIGS. 9A, B, C, and D show characterization of the StCsm mediated ATP reaction products by liquid chromatography ESI-MS analysis.

FIGS. 10A and B show characterization of the HPLC-purified oligoadenylates by liquid chromatography ESI-MS analysis.

FIGS. 12A, B, C, and D show StCsm mediated conversion of synthetic linear oligoadenylates triphosphate into the corresponding cyclic oligoadenylates.

FIGS. 13A, B, C, and D show the effect of P1 nuclease on StCsm mediated ATP reaction products.

FIGS. 27A and B shows that under certain conditions linear, instead of cyclic oligoadenylates, can be used for stimulation of Csm6 ribonucleases.

DETAILED DESCRIPTION

Figure 1:
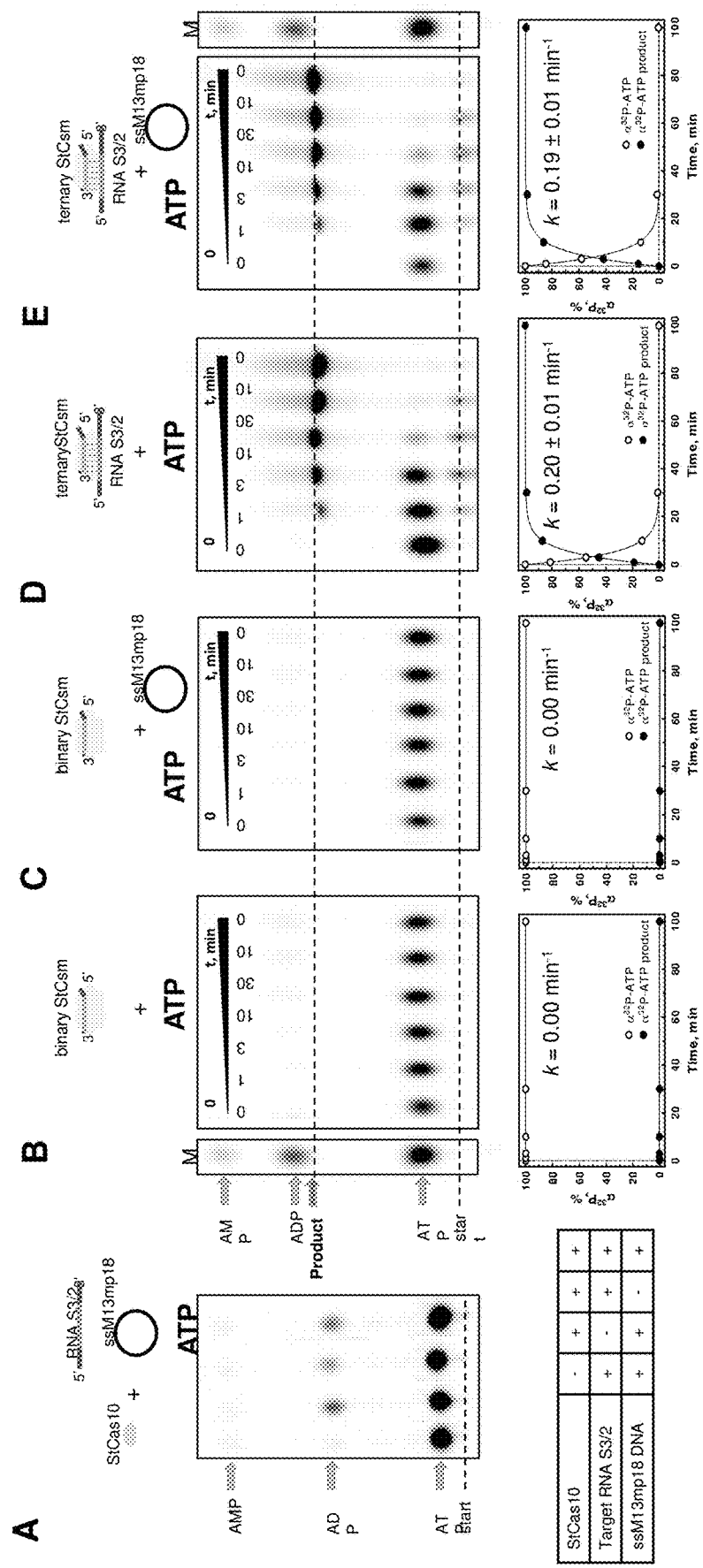
FIGS. 1A, B, C, D, and E show StCsm mediated conversion of ATP to the reaction products.

Protein cloning, expression and purification. Wild type (wt) and mutant *Streptococcus thermophilus* (St) Csm complexes were obtained as described (2). Briefly, *Escherichia coli* BL21 (DE3) was transformed with three plasmids: (i) plasmid pCas/Csm, which contains a cassette including all the cas/csm genes (except cas1 and cast) of the Type III-A CRISPR-Cas system from *S. thermophilus* DGCC8004, (ii) plasmid pCRISPR_S3, which contains four identical tandem copies of the repeat-spacer S3 unit flanked by the leader sequence and the terminal repeat, (iii) plasmid pCsm2-Tag, which contains a N-terminal-Strepll-tagged variant of csm2 gene. Next, such cells were grown at 37° C. in LB medium supplemented with streptomycin (25 µg/µl), ampicillin (50 µg/µl), and chloramphenicol (30 µg/µl) and expression of StCsm complex was induced with 1 mM IPTG. The StCsm complex was isolated by subsequent Strep-chelating affinity and size exclusion chromatography steps.

Genomic DNA isolated from *S. thermophilus* DGCC8004 strain was also used as the template for PCR amplification of the cas10 gene (1). The resulting PCR product, containing the cas10 gene, was cloned into pBAD24_C-HSH expression vector via NcoI and XhoI sites. HSH tag is a combination of Strepll-tag and two 6×Histidine-tags used to purify Cas10 protein using two different affinity chromatography steps. Full sequencing of cloned DNA fragments confirmed their identity to the original sequences. For purification of Cas10 subunit, *E. coli* DH10B (ara-) bearing wt pCas10-C-HSH plasmid was grown overnight at 16° C. in LB medium supplemented with ampicillin (50 µg/µl) after the induction of Cas10 expression with 0.2% arabinose. Cas10 protein was purified using chelating Ni-NTA (nickel-nitrilotriacetic acid) and Strep-Tactin affinity chromatographies. The elutant, containing Cas10, was dialyzed against 10 mM Tris-HCI (pH 8.5) buffer containing 300 mM KCI, 1 mM DTT, 0.1 mM EDTA, and 50% (v/v) glycerol, and stored at −20° C.

csm6 and csm6' genes were amplified separately by means of PCR, using genomic S. thermophilus DGCC8004 DNA as a template, and cloned into pJET1.2 vector. Resulting plasmids were then amplified in *E. coli* cells, purified, and cleaved with Eco31 I and PstI in order to clone these genes into pBAD24_N-HSH expression vector and generate pStCsm6-N-HSH and pStCsm6'-N-HSH plasmids. *Thermus thermophilus* csm6 gene (GenBank accession number TTHB152) was synthesized with a C-HSH Tag (General Biosystems) and cloned into pBAD24_N-Strepll vector, resulting in pTtCsm6-N-Strepll-C-HSH plasmid. Full sequencing of cloned DNA fragments confirmed their identity to the original sequences. *E. coli* DH10B (ara) was transformed with either pStCsm6-N-Tag, pStCsm6'-N-Tag or pTtCsm6-N-Strepll-C-HSH plasmid. Next, such cells were grown at 37° C. in LB medium supplemented with ampicillin (50 µg/µl) and expression of Csm6 proteins was induced with 0.2% arabinose. Subsequent His- and Strep-chelating affinity chromatography steps were employed to isolate StCsm6, StCsm6' and TtCsm6. The elutants, containing StCsm6, StCsm6' or TtCsm6, were dialyzed against 10 mM Tris-HCI (pH 8.0) buffer containing 300 mM KCl, 1 mM DTT, 0.1 mM EDTA, and 50% (v/v) glycerol, and stored at −20° C.

Plasmids p0AS1, encoding human OAS1 fused with an N-terminal His-Tag, and pPDE12, encoding human PDE12 stripped for the mitochondrial targeting peptide and containing a C-terminal His-Tag, were kindly provided by Dr. P. M. Martensen at Aarhus University. *E. coli* BL21 (DE3) cells were transformed with either p0AS1 or pPDE12 plasmid and grown at 37° C. in LB medium supplemented with ampicillin (50 µg/µl). After protein expression was induced with 1 mM IPTG, the growth temperature was reduced to 20° C. for OAS1 and 25° C. for PDE12. PDE12 was purified using chelating Ni-NTA and subsequent ion exchange (Mono Q XL, GE Healthcare) chromatographies while chelating Ni-NTA chromatography was sufficient to isolate OAS1. The elutant, containing OAS1, was dialyzed against 10 mM sodium phosphate (pH 7.4) buffer containing 300 mM NaCl, and 50% (v/v) glycerol while the PDE12-containing elutant was dialyzed against 20 mM Tris-HCI (pH 7.5) buffer containing 200 mM KCl, 1 mM DTT, and 50% (v/v) glycerol. Both were stored at −20° C.

Mutagenesis. StCsm containing Cas10 mutations D16A and D575A&D576A were obtained by the Quick Change Mutagenesis (QCM) protocol [37] and isolated following the procedures described for the wt StCsm (see above), as described in [1].

StCsm6 mutations H24A, T107A, N102A+S105A+T107A, Q129A, and R371A+H376A, as well as StCsm6' mutation R331A+H336A, were introduced into pStCsm6-N-HSH or pStCsm6'-N-HSH plasmids by means of Phusion Site-Directed Mutagenesis [38]. StCsm6 and StCsm6' proteins containing point mutations were isolated using the same protocol as for the wt Csm6 (see above). The sequences of wild-type (wt) Cas10, wt Csm6' and wt Csm6 were deposited in GenBank (accession number KM222358 for the sequence of CRISPR2-cas locus of DGCC8004).

Gel filtration. Gel filtration was carried out at room temperature on an ÄKTA FPLC system (GE Healthcare) using a Superdex 10/300 GL column (GE Healthcare), preequilibrated with 20 mM Tris-HCI (pH 8.5), 0.5 M NaCl, 7 mM 2-mercatoethanol, 1 mM EDTA. StCsm6 and StCsm6' protein samples at 0.5 mg/ml-0.6 mg/ml loading concentration were prepared in 100 µl of the above buffer. Elution from the column was monitored by measuring absorbance at 220 nm. The apparent molecular weights of proteins were evaluated from the elution volume using a series of standards (Gel filtration Calibration Kit from GE Healthcare).

Nucleotide binding assay. Nucleotide binding assays were performed by incubating different amounts of StCsm complexes with 10 nM of $^{32}$P-radiolabeled-nucleoside triphosphates in the Binding buffer (40 mM Tris, 20 mM acetic acid (pH 8.4 at 25° C.), 1 mM EDTA, 0.1 mg/ml BSA, 10% (v/v) glycerol). All reactions were incubated for 15 min at room temperature prior to electrophoresis on native 8% (w/v)

polyacrylamide gel (PAAG). Electrophoresis was carried out at room temperature for 2 h at 6 V/cm using 40 mM Tris, 20 mM acetic acid (pH 8.4 at 25° C.), 0.1 mM EDTA as the running buffer. Gels were dried and visualized by a FLA-5100 phosphorimager (Fujifilm).

StCsm mediated synthesis of cyclic oligoadenylates from ATP. The synthesis reactions of cyclic oligoadenylates by StCsm were initiated by adding 10 mM $CoCl_2$ into a mix of 200 nM StCsm, 200 nM target RNA, 50 µM ATP and 10 nM $\alpha^{32}$P-ATP in the Reaction buffer (33 mM Tris-acetate (pH 7.6 at 37° C.), 66 mM K-acetate, 0.1 mg/ml BSA) and carried out at 37° C. for 1 h or 1.5 h, unless stated otherwise. StCsm reactions on different nucleoside triphosphates contained 200 nM of ternary StCsm, 50 µM of the non-labeled nucleotide and 10 nM of the corresponding $\alpha^{32}$P-nucleotide. The reactions were stopped by adding 15 mM EDTA. Reaction products were separated by TLC on PEI Cellulose F plates (Merck) in 0.5 M phosphate buffer (pH 3.5 at 23° C.) or a denaturating 24% (19:1 acrylamide:bis-acrylamide) PAAG and visualized using autoradiography.

StCsm mediated synthesis of cyclic oligoadenylates from linear adenylate triphosphate precursors. 200 nM StCsm was mixed with 200 nM target RNA and 17 µM of triphosphate oligoadenylates $(pp(pA)_{3-6})$ in the Reaction buffer (33 mM Tris-acetate (pH 7.9 at 37° C.), 66 mM K-acetate, 0.1 mg/ml BSA) and incubated for 20 min at 37° C. before initiating the polymerase/cyclase reactions by adding 10 mM $CoCl_2$. The reactions were performed for 1.5 h at 37° C.

HLPC-MS. StCsm mediated ATP reaction products were analyzed using MS. Electrospray Ionization mass spectrometry (ESI-MS) was performed in negative mode using an integrated HPLC/ESI-MS system (1290 Infinity, Agilent Technologies/Q-TOF 6520, Agilent Technologies) equipped with a Supelco Discovery®HS C18 column (7.5 cm×2.1 mm, 3 µm). Elution was performed with a linear gradient of solvents A (5 mM ammonium acetate in water, pH 7.0) and B (acetonitrile) at a flow of 0.3 ml/min at 30° C. as follows: 0-2 min, 0% B; 2-22 min, 20% B; 22-25 min, 50% B, 25-29 min 100% B. Ionization capillary voltage was set to 5000 V, fragmentor—to 150V.

Products of the StCsm mediated AMP reactions with ATP, 2'dATP and 3'dATP were analyzed using Vanquish Binary U HPLC with DAD coupled to Q Exactive PLUS (Orbitrap) with ESI ion source. HPLC system was equipped with Hypercarb (50 mm×2.1 mm, 5p mparticle; Thermo Fisher Scientific) column. The chromatography was performed by elution with a linear gradient of solvents A (1.0 mM $NH_4HCO_3$, pH=7.8 water/acetonitrile, 95/5 (v/v)) and B (50 mM $NH_4HCO_3$, pH=9.5 water/acetonitrile, 40/60 (v/v)) at a flow of 0.4 ml/min at 50° C. as follows: 0% B to 100% B in 3 min; 100% B hold for 4 min, 100% B to 0% in 0.5 min followed by 3.5 min reconditioning. ESI-MS data was acquired in MS Scan mode from 200 to 2000 m/z at 35 k resolution in negative ionization mode. ESI parameters: Cappilary voltage 2.5 kV; Sheath Gas 35 (Arb); Aux Gas 10 (Arb); Sweep Gas 0 (Arb); Ion Tranfer Tube Temp 325° C.; Vaporizer Temp 275° C.

Purification of cyclic oligoadenylates. 200 nM StCsm was mixed with 200 nM target RNA and 50 µM ATP in the Reaction buffer (33 mM Tris-acetate (pH 7.6 at 37° C.), 66 mM K-acetate, 0.1 mg/ml BSA) and incubated for 20 min at 37° C. before initiating the reactions by adding 10 mM $CoCl_2$. The reactions were performed for 1.5 h at 37° C. Next, samples were purified by HPLC. HPLC was performed at room temperature on Waters Breeze HPLC system using a Discovery HS C18 Column (15 cm×10 mm, 5 µm) (Sigma-Aldrich Supelco) pre-equilibrated with buffer A (100 mM TEAA (pH 7.0)). Samples were fractionated at the at 1 ml/min flow rate with a linear gradient of B (60% $CH_3CN$ in buffer A) in A (0%-100% of B over 100 ml). Fractions containing different cyclic adenylates were pooled and the samples were concentrated on a vacuum concentrator (Eppendorf) prior to ESI-MS analysis.

Treatment with P1. 12 µM of cyclic oligoadenylate was incubated with 5 mU P1 nuclease (Sigma) in the P1 reaction buffer (10 mM Tris-acetate (pH 7.1 at 37° C.), 1 mM Zn-acetate) at 37° C. for 1 h. 10 µl of such reaction mix was diluted with water and loaded onto HPLC/ESI-MS system for analysis.

Treatment with PDE12. To be used as control, 2',5'-oligoadenylates were synthesized by incubating 17 pg/ml OAS1 with 2 mM ATP and 5 nM $oc^{32}$P-ATP in the OAS1 reaction buffer (4 mM Tris-HCl (pH 7.8 at 37° C.), 0.2 mM DTT, 0.1 mg/ml BSA), supplemented with 0.2 mg/ml dsRNA and 4 mM Mg-acetate, at 37° C. for 3 h. Every 10 min the reaction mix was supplemented with additional 1 mM ATP and 0.25 nM $oc^{32}$P-ATP.

12 µM of compound (mix of ATP reaction products, linear oligoadenylate (Metabion), or OAS1 reaction product) containing 7.5 nM of radioactively labeled compound, was incubated with 1.3 µg PDE12 in the PDE12 reaction buffer (20 mM HEPES (pH 7.0 at 37° C.), 1 mM DTT, 1 mM Mg-acetate) at 37° C. for 1 h. The nuclease reaction products, along with control lanes containing identical amount of untreated labeled compound, were analyzed on 24% (19:1 acrylamide:bis-acrylamide) denaturing PAAG and visualized by autoradiography.

5'-labeling reactions. 50 µM of compound (linear oligoadenylate (Metabion) or HPLC purified cyclic oligoadenylate) was incubated with 0.5 U T4 Polynucleotide kinase (PNK) and 100 nM $\gamma^{33}$P-ATP in the Reaction buffer A (50 mM Tris-HCl (pH 7.6 at 25° C.), 10 mM $MgCl_2$, 5 mM DTT, 1 mM spermidine) at 37° C. for 30 min. In case of direct 5'-labeling of the StCsm ATP reaction mix, which initially contained 50 pM ATP, the sample was diluted twice and then incubated with T4 PNK under identical conditions. The 5'-labeling reaction products were analyzed on 24% (19:1 acrylamide:bis-acrylamide) denaturing PAAG and visualized by autoradiography.

Sequence alignment. Clustal Omega (Sievers et al. Molecular Systems Biology 7 (2011) 539 (2011) and McWilliam et al. Nucleic acids research 41(W1):W597-W600 (2013) was used for multiple sequence alignment of different Csm6 proteins.

Csm6 nuclease assay. StCsm6, StCsm6', and TtCsm6 nuclease assays were conducted in the Reaction buffer (33 mM Tris-acetate (pH 7.6 at 37° C.), 66 mM K-acetate, 0.1 mg/ml BSA) supplemented with 1 mM EDTA and containing 5 nM of 5'-radiolabeled and 5 nM of unlabeled RNA NS (unless stated otherwise; see all RNA substrates used in this study in Table 1) and 500 nM of cyclic oligoadenylate mixture or 0.5-500 nM of the HPLC purified cyclic oligoadenylate effectors or 5-500 nM linear oligoadenylate with various phosphorylation levels—linear oligoadenylate 5'-triphosphate (ChemGenes); non-phosphorylated, 3'P (Metabion) or 5'P containing linear oligoadenylates. 5'P-oligoadenylates were obtained by incubating 3.(3) µM of non-phosphorylated linear oligoadenylate with 0.5 U T4 polynucleotide kinase and 1 mM ATP in the Reaction buffer A at 37° C. for 40 min.

Reactions were started by adding 0-10 µM Csm6 and carried out at 37° C. The reaction products were separated on a denaturing 15% (29:1 acrylamide:bis-acrylamide)

PAAG and visualized by autoradiography. StCsm6 nuclease assays with ATP additionally contained 1 mM of ATP in the reaction mixture.

Data analysis. The Kyplot 2.0 software [45] was used for calculation of StCsm ATP reaction rate and StCsm6 and StCsm6' ssRNA cleavage efficiency.

FIG. 1 shows StCsm mediated conversion of ATP to the reaction products. (FIG. 1A) ATP reaction of an individual StCas10 subunit. The reactions contained 200 nM StCas10, 50 μM ATP, 10 nM $\alpha^{32}$P-ATP (Perkin Elmer), 200 nM target RNA S3/2 and/or 5 nM M13 mp18 ssDNA. The assays were performed at 37° C. in the Reaction buffer supplemented with 10 mM $CoCl_2$. Samples were analyzed by thin-layer chromatography (TLC), followed by phosphorimaging. Reaction products of the binary StCsm complex (Cas/Csm proteins plus crRNA) and ATP in the absence or in the presence of single-stranded (ss) DNA are presented in (FIG. 1B) and (FIG. 1C), respectively. Reaction products of the ternary StCsm complex (Cas/Csm proteins plus crRNA and target RNA) and ATP in the absence or in the presence of ssDNA are presented in (FIG. 1D) and (FIG. 1E), respectively. The reactions contained 200 nM of the binary or ternary StCsm, 50 μM ATP, 10 nM $\alpha^{32}$P-ATP and 10 nM M13 mp18 ssDNA. The assays were performed at 37° C. in the Reaction buffer supplemented with 10 mM $CoCl_2$ and the samples were analyzed by TLC, followed by phosphorimaging. Heating $\alpha^{32}$P-ATP at 95° C. for 60 min was used to generate radiolabeled ADP and AMP, which were used as a TLC control (marked as lane M). Rate constants of ATP decay, which are presented bellow each TLC plate, were calculated by fitting single exponentials to the substrate depletion data. Cartoons above the graphs depict reaction components: protospacer is grey in between black lines, the complementary strand (matching spacer in crRNA) is lighter grey, DNA is a black circle.

Figure 2:
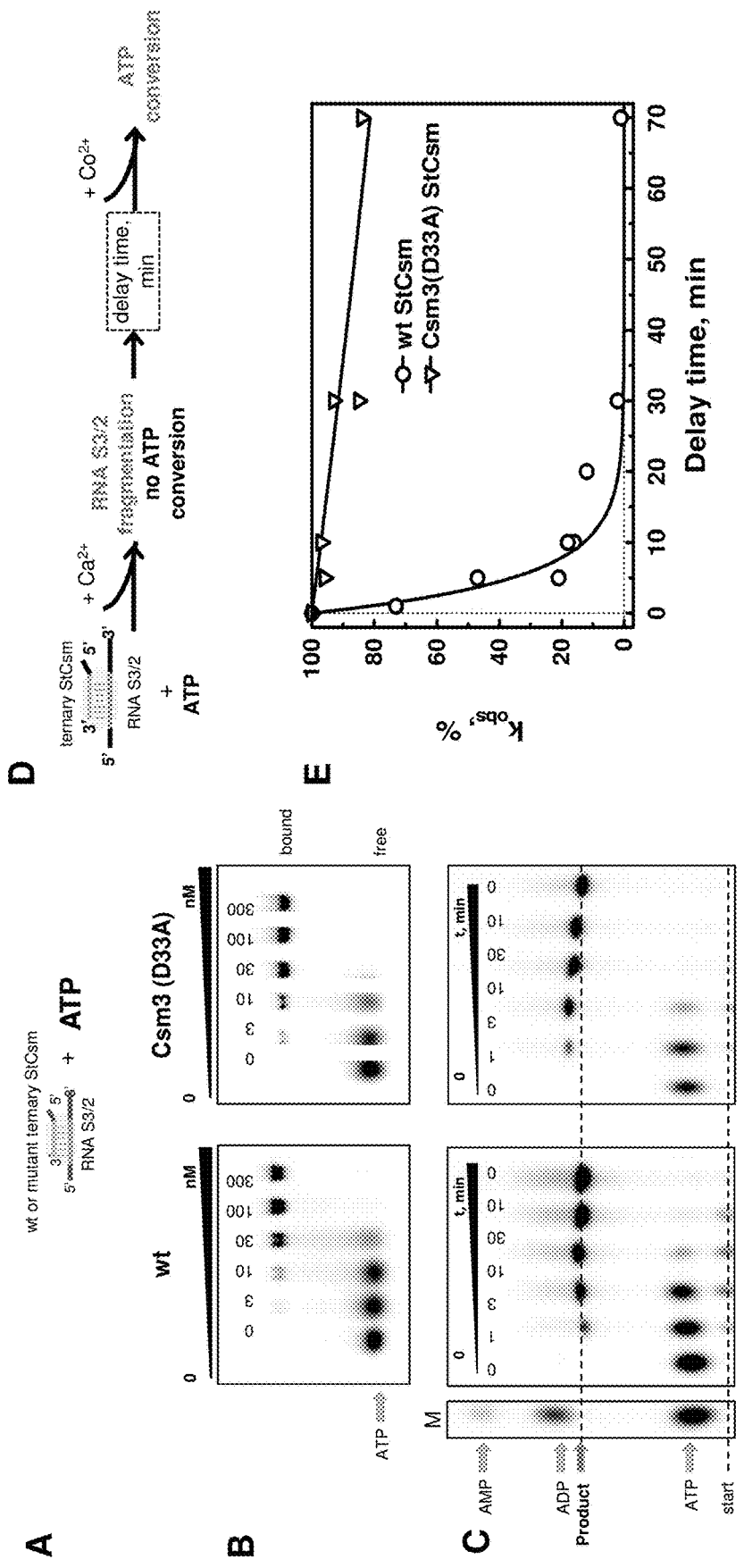
FIGS. 2A, B, C, D, and E show RNase-activity-deficient (Csm3 D33A mutant) ternary StCsm complex mediated conversion of ATP to the reaction products.

FIG. 2 shows RNase-activity-deficient (Csm3 D33A mutant) ternary StCsm complex mediated conversion of ATP to the reaction products. (FIG. 2A) Reaction components are shown schematically in the same manner as in FIG. 1. (FIG. 2B) Electrophoretic mobility shift assay (EMSA) of ATP binding by wild-type (wt) and RNase-activity-deficient ternary StCsm complexes. The binding reactions contained 2 nM $\alpha^{32}$P-radiolabeled, 8 nM non-labeled ATP and the ternary StCsm at concentrations indicated by each lane. Samples were analyzed in polyacrylamide gel (PAAG) under non-denaturing conditions. (FIG. 2C) The reactions contained 200 nM of the ternary wt or mutant StCsm, 50 μM ATP and 10 nM $\alpha^{32}$P-ATP. The assays were performed at 37° C. in the Reaction buffer supplemented with 10 mM $CoCl_2$ and the samples were analyzed by TLC, followed by phosphorimaging. Heating $\alpha^{32}$P-ATP at 95° C. for 60 min was used to generate radiolabeled ADP and AMP, which were used as a TLC control (marked as lane M). (FIG. 2D) Cartoon depicting the experimental strategy to monitor the temporal control of ATP conversion to the reaction products by the ternary StCsm. First, StCsm ternary complex is mixed with ATP and RNase cleavage is triggered by addition of $Ca^{2+}$ cofactor. After a certain delay time, the ATP conversion to the reaction products is initiated by adding $Co^{2+}$. (FIG. 2E) Delay time dependence of the relative ATP conversion to the reaction products by the wt StCsm and RNA cleavage deficient StCsm (Csm3 D33A) variant. The reactions contained 200 nM of the ternary wt or mutant StCsm, 50 μM ATP and 10 nM $\alpha^{32}$P-ATP. The assays were performed at 37° C. in the Reaction buffer supplemented first with 1 mM $CaCl_2$ and, after a certain delay time, with 10 mM $CoCl_2$. The samples were analyzed by TLC, followed by phosphorimaging. Reaction rate with 0 delay time was equated to 100%.

Figure 3:
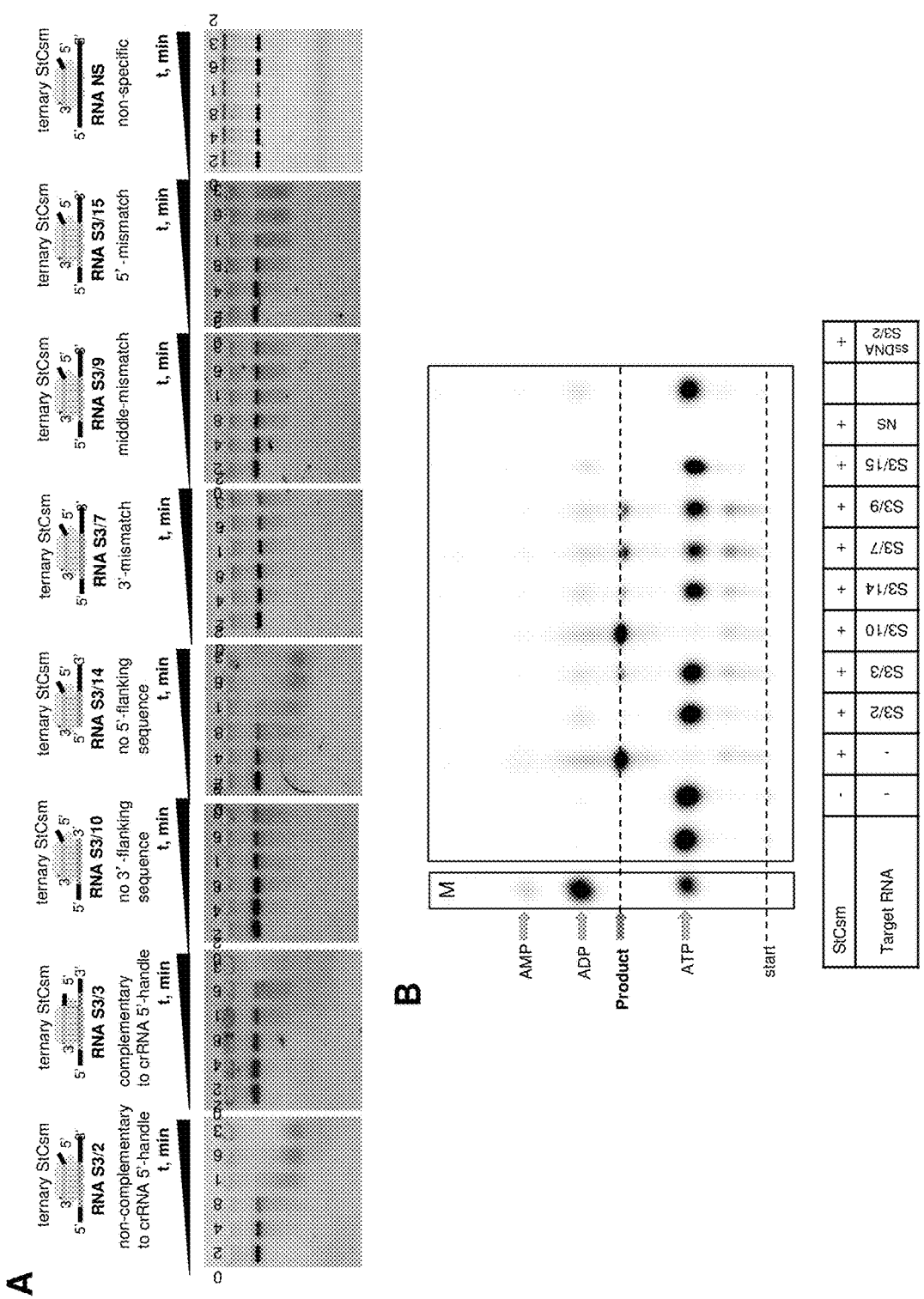
FIGS. 3A and B show target RNA sequence requirements for the StCsm mediated conversion of ATP to the reaction products.

FIG. 3 shows target RNA sequence requirements for the StCsm mediated conversion of ATP to the reaction products. (FIG. 3A) Cartoons above gels depict ternary StCsm complexes that differ in the bound target RNA molecules in the same manner as in FIG. 1. The agarose gels show degradation patterns of 1 nM of circular M13 mp18 ssDNA in the presence of 5 nM ternary StCsm complexes containing different RNAs FIG. 3A is reproduced from (1). All RNA substrates used here are bound and cleaved by the StCsm ribonuclease (2). (FIG. 3B) Reaction products of various ternary StCsm complexes with ATP. The reactions contained 200 nM of the ternary StCsm with different nucleic acids (NA), 50 μM ATP and 10 nM $\alpha^{32}$P-ATP. The assays were performed at 37° C. in the Reaction buffer supplemented with 10 mM $CoCl_2$ and the samples were analyzed by TLC, followed by phosphorimaging. Heating $\alpha^{32}$P-ATP at 95° C. for 60 min was used to generate radiolabeled ADP and AMP, which were used as a TLC control (marked as lane M).

Figure 4:
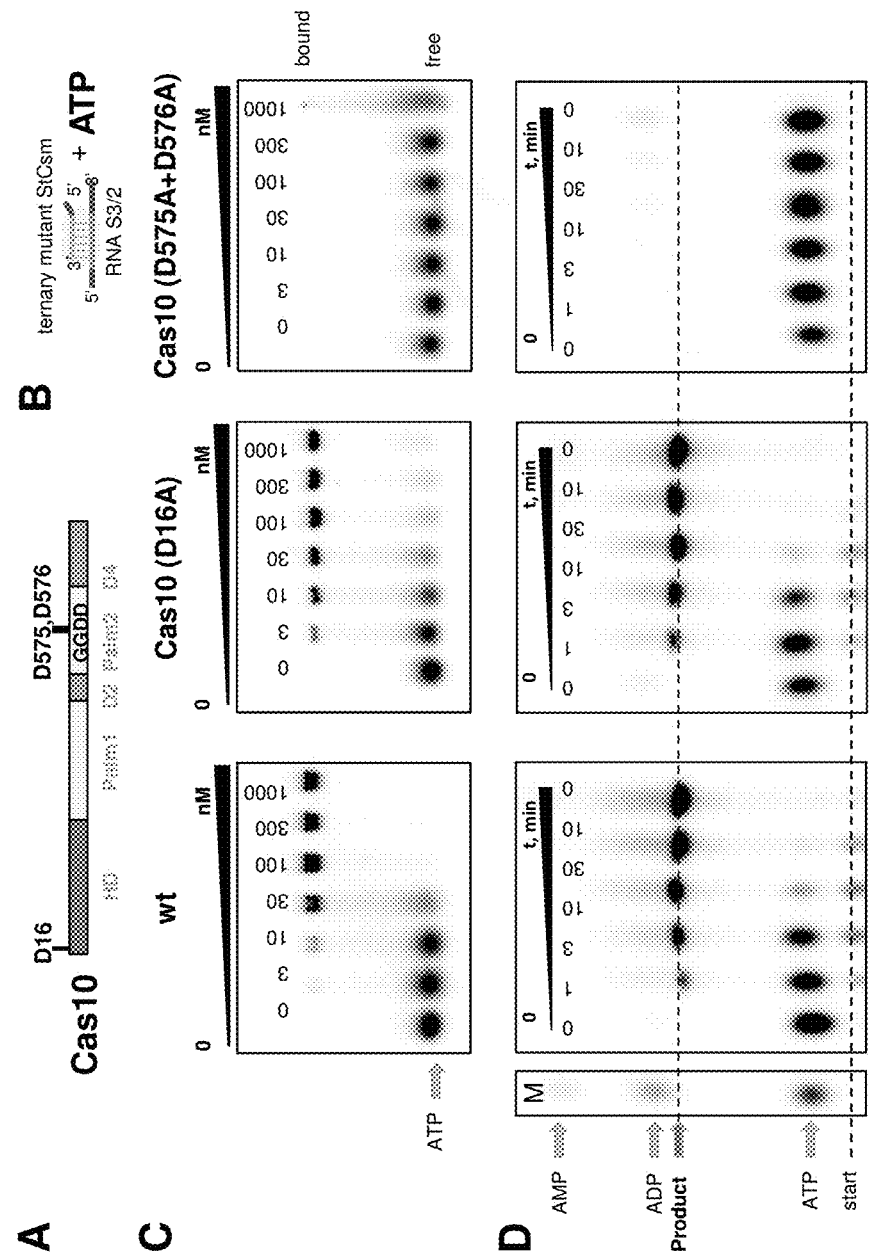
FIGS. 4 A, B, C, and D show the effect of mutations in StCsm Cas10 HD and Palm domains on the conversion of ATP to the reaction products.

FIG. 4 shows the effect of mutations in StCsm Cas10 HD and Palm domains on the conversion of ATP to the reaction products. (FIG. 4A) Domain architecture of the *S. thermophilus* Cas10 protein. HD-domain denotes HD-type phosphohydrolase/nuclease domain (dark grey or left); two Palm-domains denote polymerase/cyclase-like Palm domains, one of which contains GGDD-motif (light grey) (SEQ ID NO: 1); D2 and D4 denote a-helical domains (grey). Conserved active site residues subjected to alanine mutagenesis are indicated above the boxes. (FIG. 4B) Reaction components are shown schematically in the same manner as in FIG. 1. (FIG. 4C) EMSA of ATP binding by wt and Cas10-mutant ternary StCsm complexes. The binding reactions contained 2 nM $\alpha^{32}$P-radiolabeled, 8 nM non-labeled ATP and the ternary StCsm at concentrations indicated by each lane. Samples were analyzed in PAAG under nondenaturing conditions. (FIG. 4D) Reaction products of the wt and Cas10-mutant ternary StCsm complex and ATP. The reactions contained 200 nM of the ternary mutant StCsm, 50 μM ATP and 10 nM $\alpha^{32}$P-ATP. The assays were performed at 37° C. in the Reaction buffer supplemented with 10 mM $CoCl_2$ and the samples were analyzed by TLC, followed by phosphorimaging. Heating $\alpha^{32}$P-ATP at 95° C. for 60 min was used to generate radiolabeled ADP and AMP, which were used as a TLC control (marked as lane M).

Figure 5:
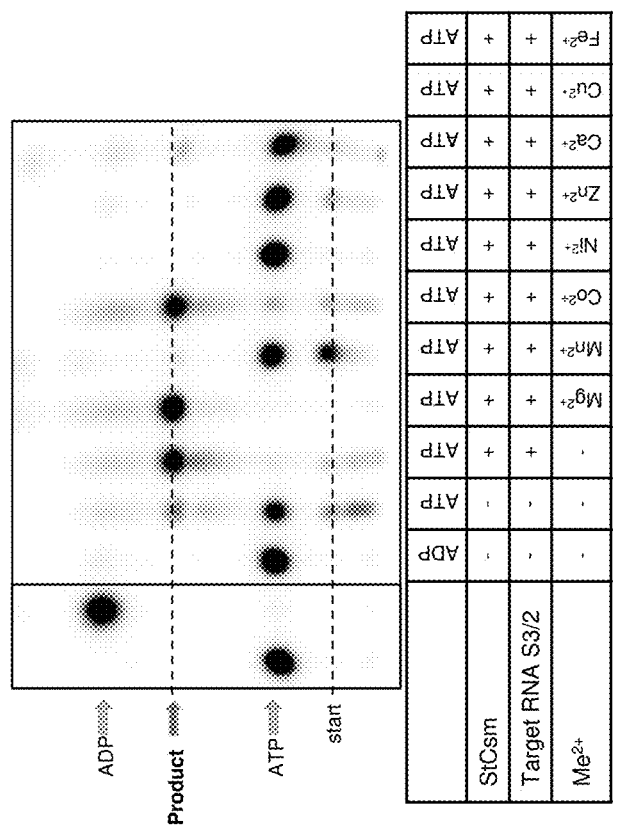
FIG. 5 shows metal ion requirements for the StCsm mediated conversion of ATP to the reaction products.

FIG. 5 shows metal ion requirements for the StCsm mediated conversion of ATP to the reaction products. The reactions contained 200 nM of the ternary StCsm, 50 μM ATP and 10 nM $\alpha^{32P}$-ATP. The assays were performed at 37° C. in the Reaction buffer supplemented with 1 mM EDTA, 10 mM Mg-acetate, 10 mM $MnCl_2$, 10 mM $CoCl_2$, 0.1 mM $NiCl_2$, 0.1 mM $ZnSO_4$, 1 mM Ca-acetate, 1 mM $CuSO_4$ or 10 mM $FeSO_4$ and the samples were analyzed by TLC, followed by phosphorimaging. For control, radiolabeled ADP was generated by mixing $\alpha^{32}$P-ATP, T4 PNK and ssDNA S3/2 in PNK A buffer (ThermoFisher) and incubating at 37° C. for 30 min.

Figure 6:
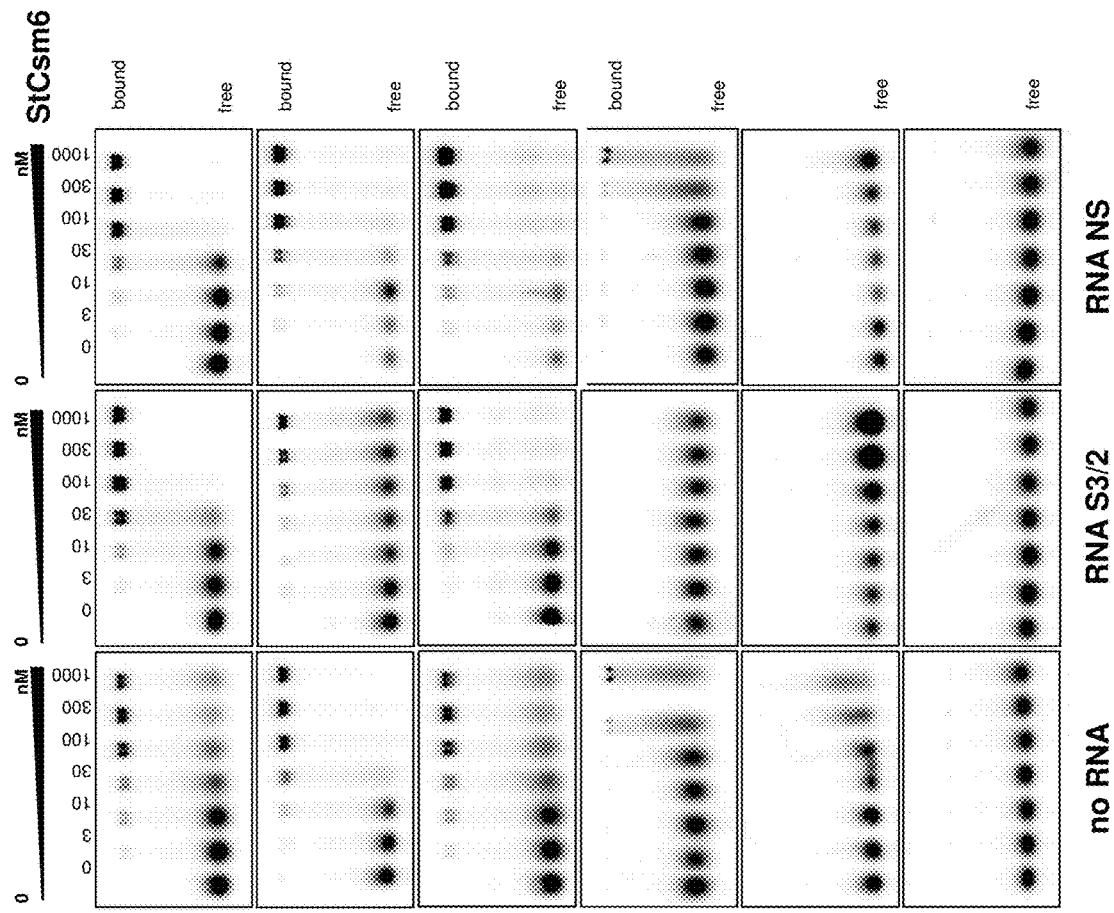
FIG. 6 shows StCsm binding selectivity for various nucleoside triphosphates (NTPs).

FIG. 6 shows StCsm binding selectivity for various nucleoside triphosphates (NTPs). NTP binding by binary and ternary StCsm complexes was monitored using EMSA. The binding reactions contained 2 nM of $\alpha^{32}$P-radiolabeled and 8 nM of the corresponding non-labeled nucleotide (ATP, 2'dATP, 3'dATP, GTP, UTP or CTP (Perkin Elmer)) in addition to the StCsm complex (without RNA, with the target RNA S3/2 or non-specific RNA NS, as denoted above the gels), at concentrations indicated by each lane. Samples were analyzed in PAAG under non-denaturing conditions.

Figure 7:
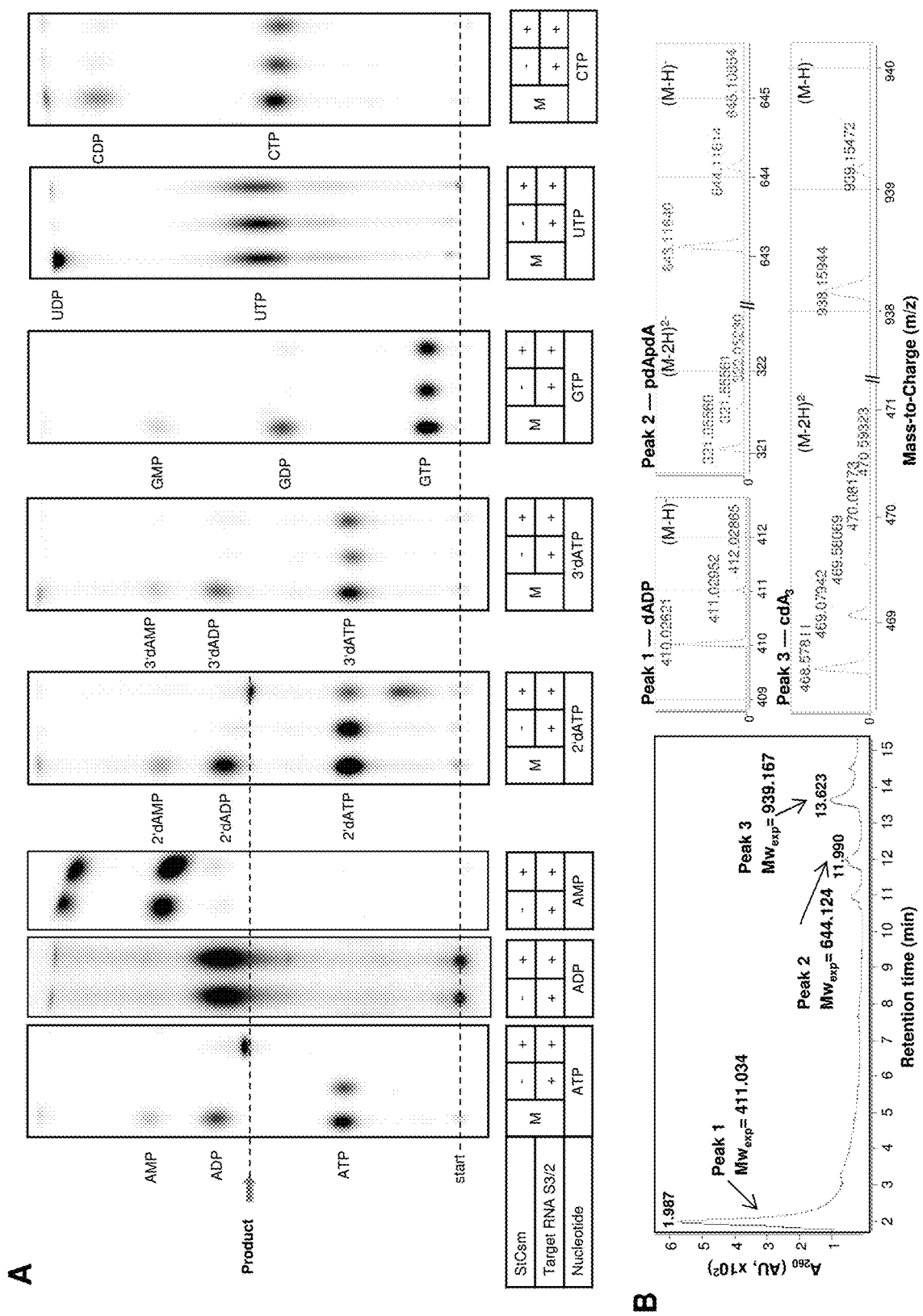
FIG. 7 shows StCsm reactions on different NTPs.

FIG. 7 shows StCsm reactions on different NTPs. (A) Ternary StCsm complex was incubated with ATP, 2'dATP, 3'dATP, GTP, CTP or UTP radiolabeled nucleotides. The reactions contained 200 nM of the ternary StCsm, 50 µM of the non-labeled nucleotide and 10 nM of the corresponding $\alpha^{32}$P-nucleotide. The assays were performed at 37° C. for 60 min in the Reaction buffer supplemented with 10 mM $CoCl_2$ and samples were analyzed by TLC, followed by phosphorimaging. (B) The products of StCsm-mediated 2'dATP reaction were further analyzed by ion pair reverse-phase (RP) HPLC-MS. On the left panel, HPLC analysis is presented. On the right panels, the isotopic patterns of ions (without one, (M-H)-, or two (M-2H)2-protons) of the identified compounds are presented.

FIG. 8 shows StCsm mediated AMP reaction with ATP, 2'dATP and 3'dATP. TLC analysis of StCsm reaction products involving 10 nM of $\alpha^{32}$P-radiolabeled ATP (FIG. 8A), 2'-dATP (FIG. 8B) or 3'-dATP (FIG. 8C). 200 nM of ternary StCsm complex were mixed with the nucleotides (concentrations are indicated below the TLC plate) and incubated at 37° C. for 90 min in the Reaction buffer supplemented with 10 mM $CoCl_2$ and samples were analyzed by TLC, followed by phosphorimaging. Heating $\alpha^{32}$P-NTP at 95° C. for 60 min was used to generate radiolabeled ADP and AMP (or corresponding deoxynucleotides), which were used as a TLC control (first control lane in FIGS. 8A-C, marked as lane M). In case of AMP reaction with ATP, 2'dATP or 3'dATP, new bands in TLC plates, corresponding to unknown products, were identified. These unlabeled products were then prepared incubating ternary StCsm with 25 µM AMP and 25 µM of corresponding non-radioactive NTP and products were analyzed by HPLC-MS (FIGS. 8D-F), identifying the reaction products as corresponding dinucleotides, depicted in (FIGS. 8G-I).

FIG. 9 shows characterization of the StCsm mediated ATP reaction products by liquid chromatography ESI-MS analysis. (FIG. 9A) Ion pair reverse-phase (RP) HPLC analysis of StCsm ATP reaction products is presented. (FIG. 9B) Mass spectra of compounds identified in StCsm ATP reaction mixture. (FIG. 9C) Isotopic patterns of the identified compounds. (FIG. 9D) Observed molecular masses and yields of the identified putative compounds.

FIG. 10 shows characterization of the HPLC-purified oligoadenylates by liquid chromatography ESI-MS analysis. (FIG. 10A) Ion pair RP HPLC chromatogram of StCsm ATP reaction products is presented. Fractions for three main peaks were pooled separately and analyzed further by ESI MS/MS analysis. (FIG. 10B) Ion pair RP HPLC analysis and ESI-MS spectra of the HPLC-purified oligoadenylates.

Figure 11:
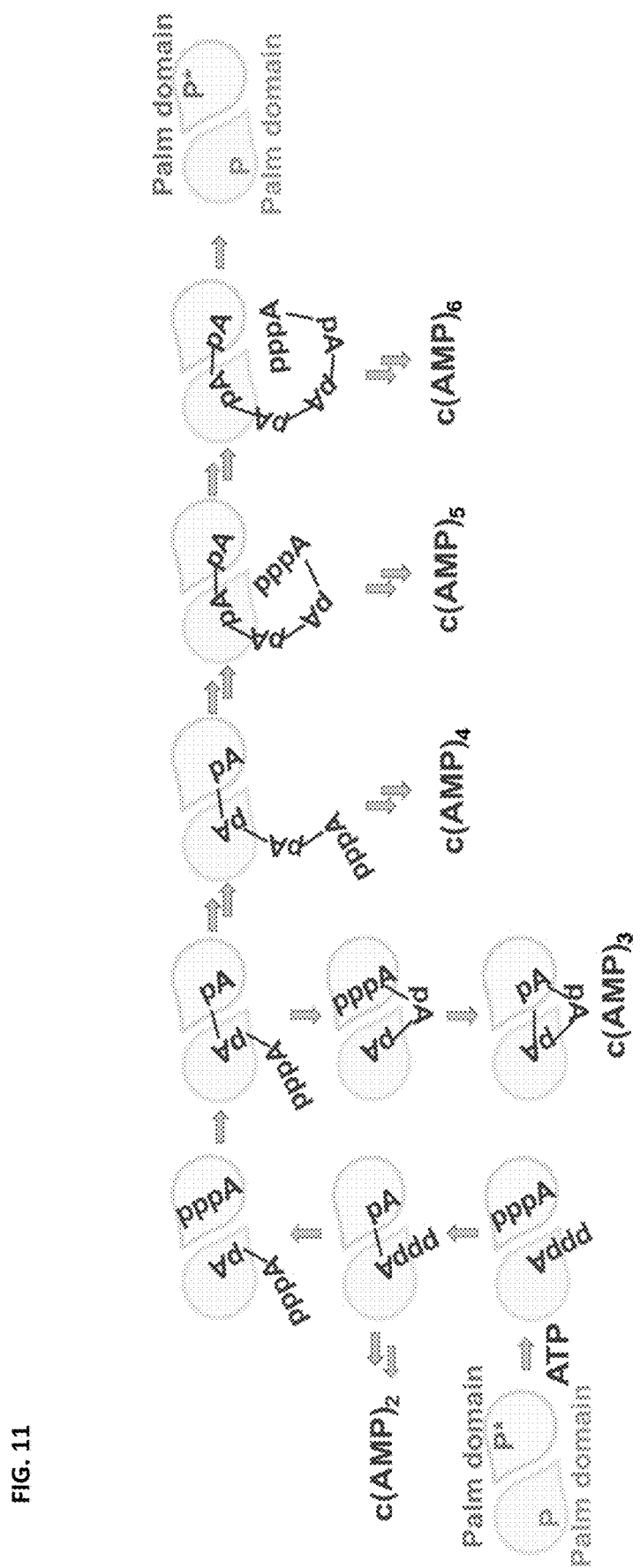
FIG. 11 shows a proposed model for StCsm-mediated ATP polymerase and cyclase reaction mechanism.

FIG. 11 shows a proposed model for StCsm-mediated ATP polymerase and cyclase reaction mechanism. Cas10 protein, which is part of the StCsm effector complex, possesses two ferredoxin-like fold domains P* and P, homologous to the Palm domain of nucleic acid polymerases and nucleotide cyclases. The one Palm domain appears to be catalytically inactive, whereas the other has a putative active site featuring the conserved GGDD-motif (SEQ ID NO: 1). Both of them could be capable of binding ATP molecules. ATP binding in the P site positions the 3'-OH for the nucleophilic attack on the αP atom of the ATP molecule bound in the P* site. After the initial reaction, the product could reposition between the Palm domains so that the 3'-hydroxyl group of pppApA dinucleotide could attack its own triphosphate moiety, yielding cyclic (c) $(AMP)_2$ (also known as c-di-AMP). Alternatively, the triphosphate moiety of pppApA dinucleotide could be bound in only one of the Palm domains and ready for attack by a new ATP molecule. After a trinucleotide is formed, there are two competing ways for the reaction to go. Under the conditions described herein, formation of $c(AMP)_3$ was observed as the predominant reaction. In such case the trinucleotide could reposition within the two Palm domains for an intramolecular cyclisation reaction, in which the 3'-hydroxyl group of pppApApA trinucleotide would attack the 5'-triphosphate group, resulting in formation of $c(AMP)_3$. Alternatively, the trinucleotide could polymerize further with another ATP molecule before the cyclisation reaction would occur, which would result in $c(AMP)_4$, $c(AMP)_5$ or $c(AMP)_6$.

FIG. 12 shows StCsm mediated conversion of synthetic linear oligoadenylates triphosphate into the corresponding cyclic oligoadenylates. 200 nM of ternary StCsm was incubated with 17 µM of triphosphate oligoadenylate—$pp(pA)_3$ (FIG. 12A), $pp(pA)_4$ (FIG. 12B), $pp(pA)_5$ (FIG. 12C) and $pp(pA)_6$ (FIG. 12D) (ChemGenes))—in the Reaction buffer supplemented with 10 mM $CoCl_2$ for 90 min at 37° C. The samples were purified by HPLC and analyzed by ion pair RP HPLC and ESI-MS.

FIG. 13 shows hydrolysis of StCsm mediated ATP reaction products by P1 nuclease. P1 nuclease from Penicillium citrinum degrades single-stranded RNA (and less efficiently DNA) to nucleoside 5'-monophosphates. P1 nuclease shows high phosphomonoesterase activity toward 3'-ribonucleotides, but 2'-ribonucleotides are extremely resistant to P1 (3, 4). HPLC purified compounds (tri-adenylate, tetra-adenylate, penta-adenylate, synthesized by StCsm from ATP, and hexa-adenylate, synthesized by StCsm from $pp(pA)_6$ precursor) were tested under P1 nuclease digestion. Next, the samples were analyzed by ion pair RP HPLC and ESI-MS. HPLC chromatograms are presented in (FIG. 13A). ESI-MS results are summarized in the Table (FIG. 13B). MW 347.06 was identified in tri-adenylate, tetra-adenylate, penta-adenylate and hexa-adenylate P1 nuclease digestion reactions and corresponds to AMP (theoretical MW 347.06). Molecular mass of adenosine-2', 3'-cyclic phosphate, which could result from digestion of the linear oligoadenylate (schematically presented in (FIG. 13C)), was not detected. Scheme for cyclic-triadenylate compound hydrolysis by P1 nuclease, which would result in only adenosine monophosphate (AMP), is presented in panel (FIG. 13D).

Figure 14:
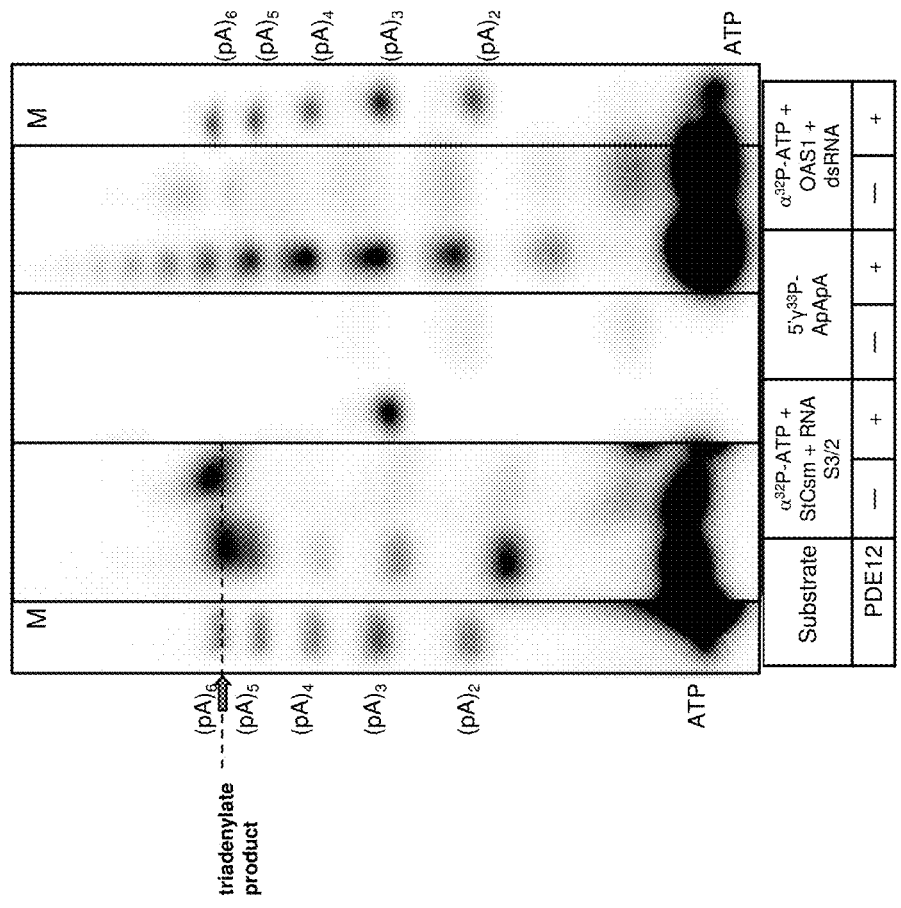
FIG. 14 shows the effect of nuclease PDE12 hydrolysis on the StCsm mediated ATP reaction products.

FIG. 14 shows treatment of the StCsm mediated ATP reaction products with nuclease PDE12. PDE12 exhibits exonuclease activity on 2',5'- and 3',5'-adenylates (5, 6). The products of reaction containing 200 nM of ternary StCsm, 50 µM ATP and 10 nM $\alpha^{32}$P-ATP were mixed with unlabeled products of analogous reaction (total compound concentration 12 µM) and incubated with PDE12 at 37° C. for 1 h in the PDE12 reaction buffer. As a control, a 5'- $\gamma^{33}$P-labeled tri-adenylate (with 3'-5' phosphodiester bonds) and $\alpha^{32}$P-labeled 2',5'-oligoadenylates, produced by OAS1 (7), were subjected to identical PDE12 treatment.

Figure 15:
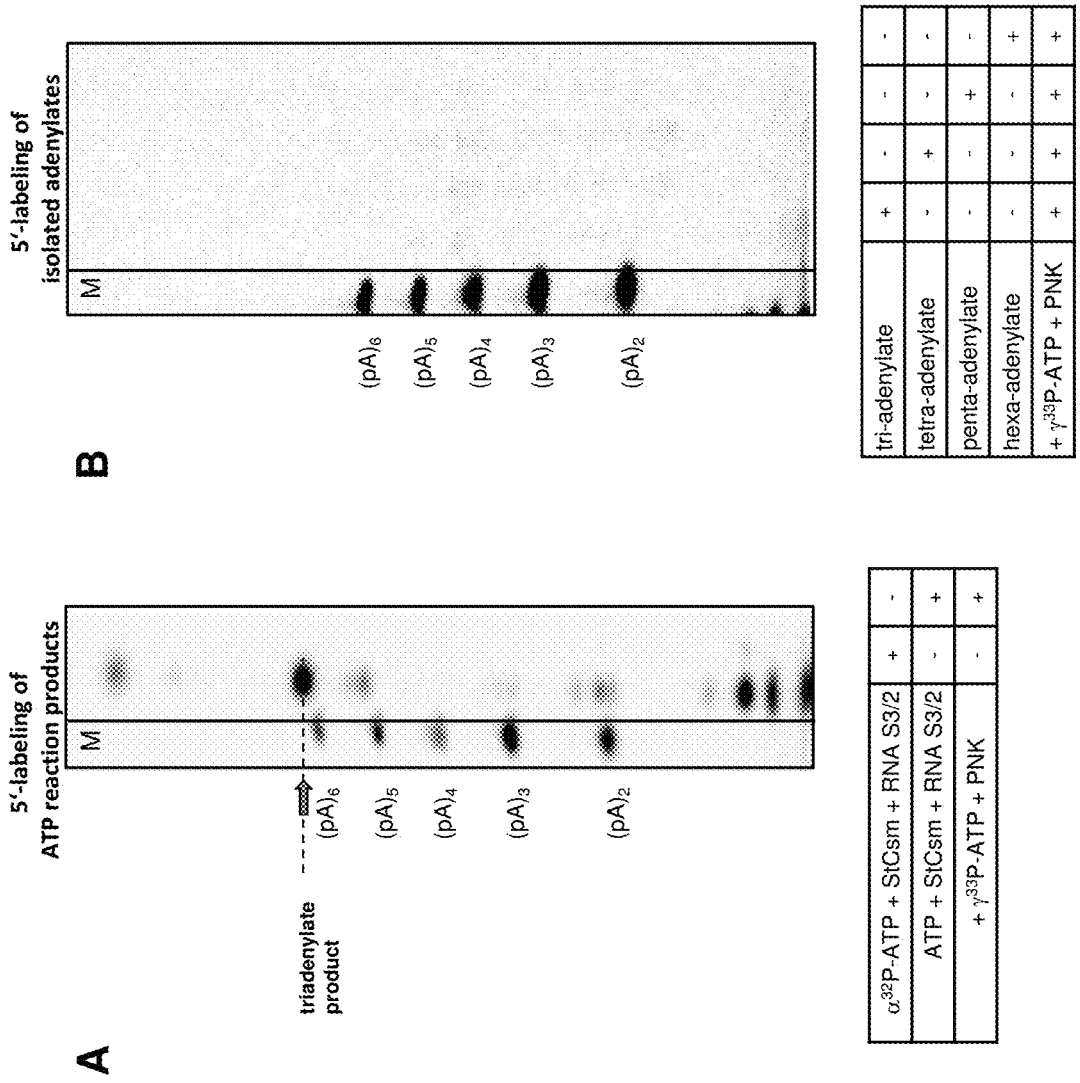
FIGS. 15A and B show 5'-end labeling of the StCsm mediated ATP reaction products.

FIG. 15 shows 5'-end labeling of the StCsm mediated ATP reaction products. (FIG. 15A) The products from ATP reaction, which contained 200 nM of the ternary StCsm and 50 µM ATP, was labeled in the 5'-labeling reaction using T4 PNK and $\gamma^{33}$P ATP (Perkin Elmer). Only traces of linear pApA were detected. (FIG. 15B) 50 µM of HPLC purified compounds (tri-adenylate, tetra-adenylate, penta-adenylate, synthesized by StCsm from ATP, and hexa-adenylate, synthesized by StCsm from $pp(pA)_6$ precursor) were subjected to identical 5'-labeling reactions. Linear oligoadenylates (ApA, ApApA, $(Ap)_3A$, $(Ap)_4A$, $(Ap)_5A$, (Metabion)) were 5'-radiolabeled in the same way to serve as both control and marker. All samples were analyzed in PAAG under denaturating conditions, together with the products gained from reaction containing 200 nM of the ternary StCsm, 50 µM ATP and 10 nM $\alpha^{32}$P-ATP.

Figure 16:
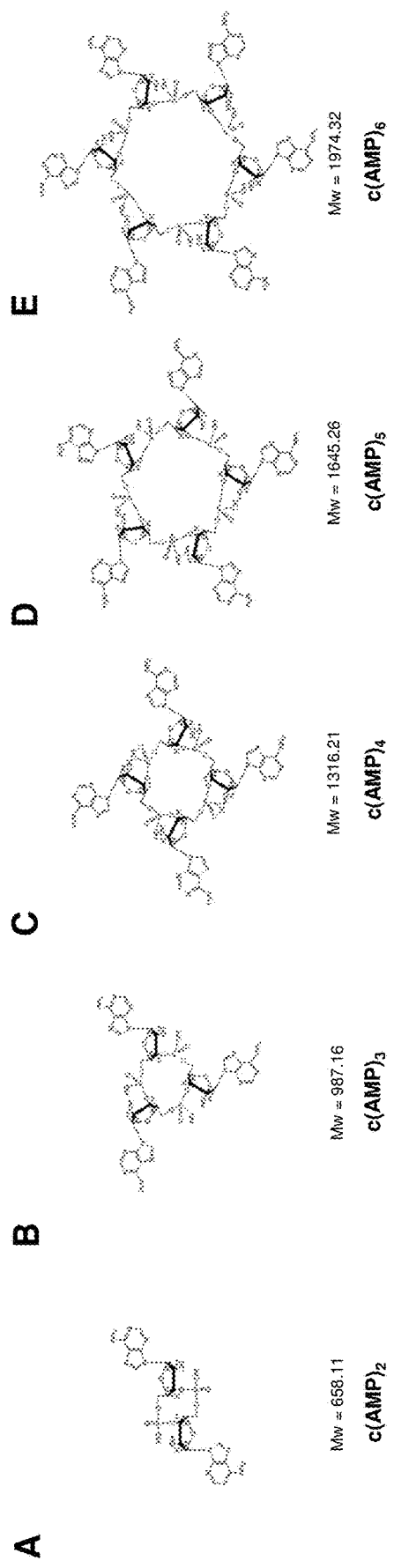
FIGS. 16A, B, C, D, and E show compounds synthesized from ATP by StCsm. Cyclic (c) (3'-5') di-adenylate, tri-adenylate, c-tetra-adenylate, c-penta-adenylate and c-hexa-adenylate are shown schematically.

FIG. 16 shows compounds synthesized from ATP by StCsm. Cyclic (c) (3'-5') di-adenylate, tri-adenylate, c-tetra-adenylate, c-penta-adenylate and c-hexa-adenylate are shown schematically.

Figure 17:
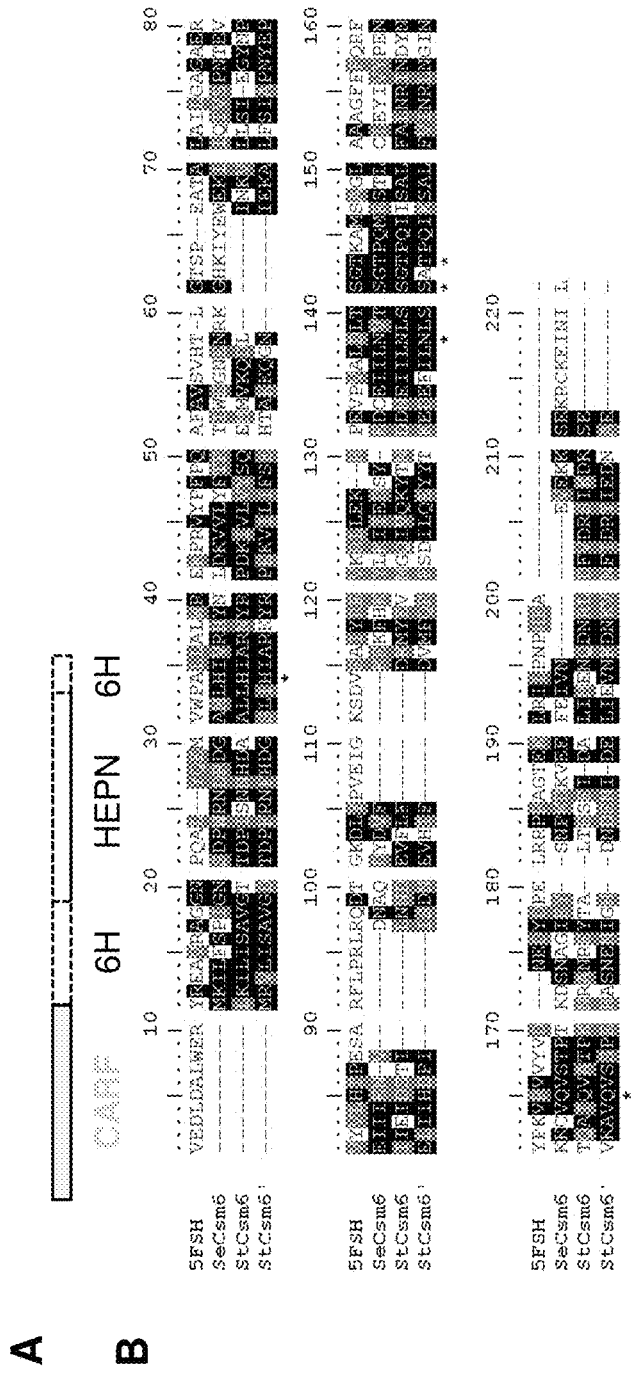
FIGS. 17A and B show frames and sequence alignment, respectively, of the CARF domain of each of 5FSH (SEQ ID NO: 3), SeCsm6 (SEQ ID NO: 4), StCsm6 (SEQ ID NO: 5) and StCsm6' (SEQ ID NO: 6).

FIG. 17 shows sequence alignment of the CARF domain of StCsm6 and StCsm6'. (FIG. 17A) Domain architecture of StCsm6. Only CARF domain (light grey or left) was used in the alignment. (FIG. 17B) Sequence alignment of the CARF domain of *Thermus thermophilus* Csm6 (TtCsm6, PDB ID: 5FSH (SEQ ID NO: 3)) with StCsm6 (SEQ ID NO: 5), StCsm6' (SEQ ID NO: 6) and *Staphylococcus epidermidis* Csm6 (SeCsm6; SEQ ID NO: 4). Putative ligand binding site residues targeted for mutagenesis in StCsm6 are denoted by asterisks below the alignment. 4RGP (SEQ ID NO: 7), SeCsm6 (SEQ ID NO: 8), StCsm6 (SEQ ID NO: 9) and StCsm6' (SEQ ID NO: 10).

Figure 18:
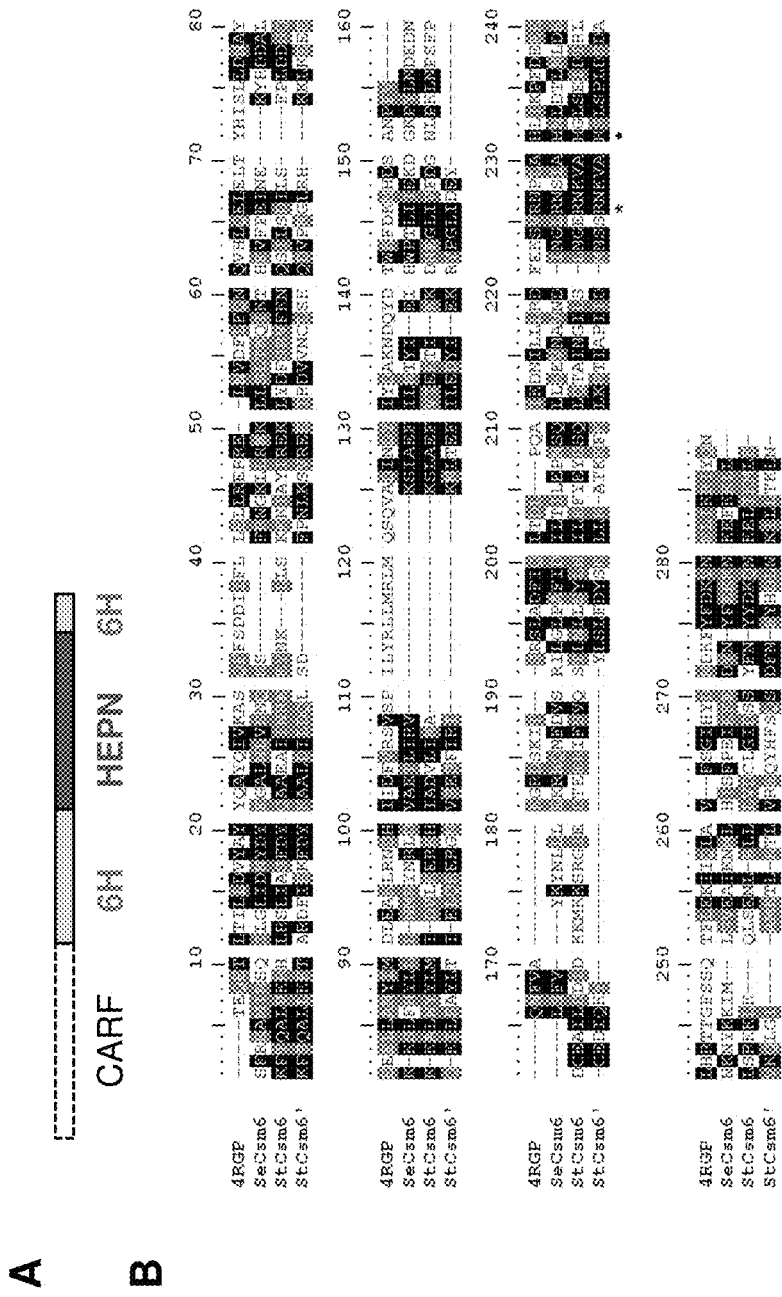
FIGS. 18A and B show frames and sequence alignment, respectively, of the HEPN domain of 4RGP (SEQ ID NO: 7), SeCsm6 (SEQ ID NO: 8), StCsm6 (SEQ ID NO: 9) and StCsm6' (SEQ ID NO: 10).

FIG. 18 shows sequence alignment of the HEPN domain of StCsm6 and StCsm6'. (FIG. 18A) Domain architecture of the *S. thermophilus* Csm6 protein. Only C-terminal region containing HEPN domains (dark grey) and a-helical region (denoted as 6H [8], light grey) was used in the alignment. (FIG. 18B) Alignment of Streptococcus mutans Csm6 (SmCsm6, PDB ID: 4RGP (SEQ ID NO: 7)) with StCsm6 (SEQ ID NO: 9), StCsm6' (SEQ ID NO: 10) and SeCsm6 (SEQ ID NO: 8). Residues of the active site motif (RXXXXH) (SEQ ID NO: 14) targeted for mutagenesis in HEPN domain are denoted by asterisks below the alignment.

Figure 19:
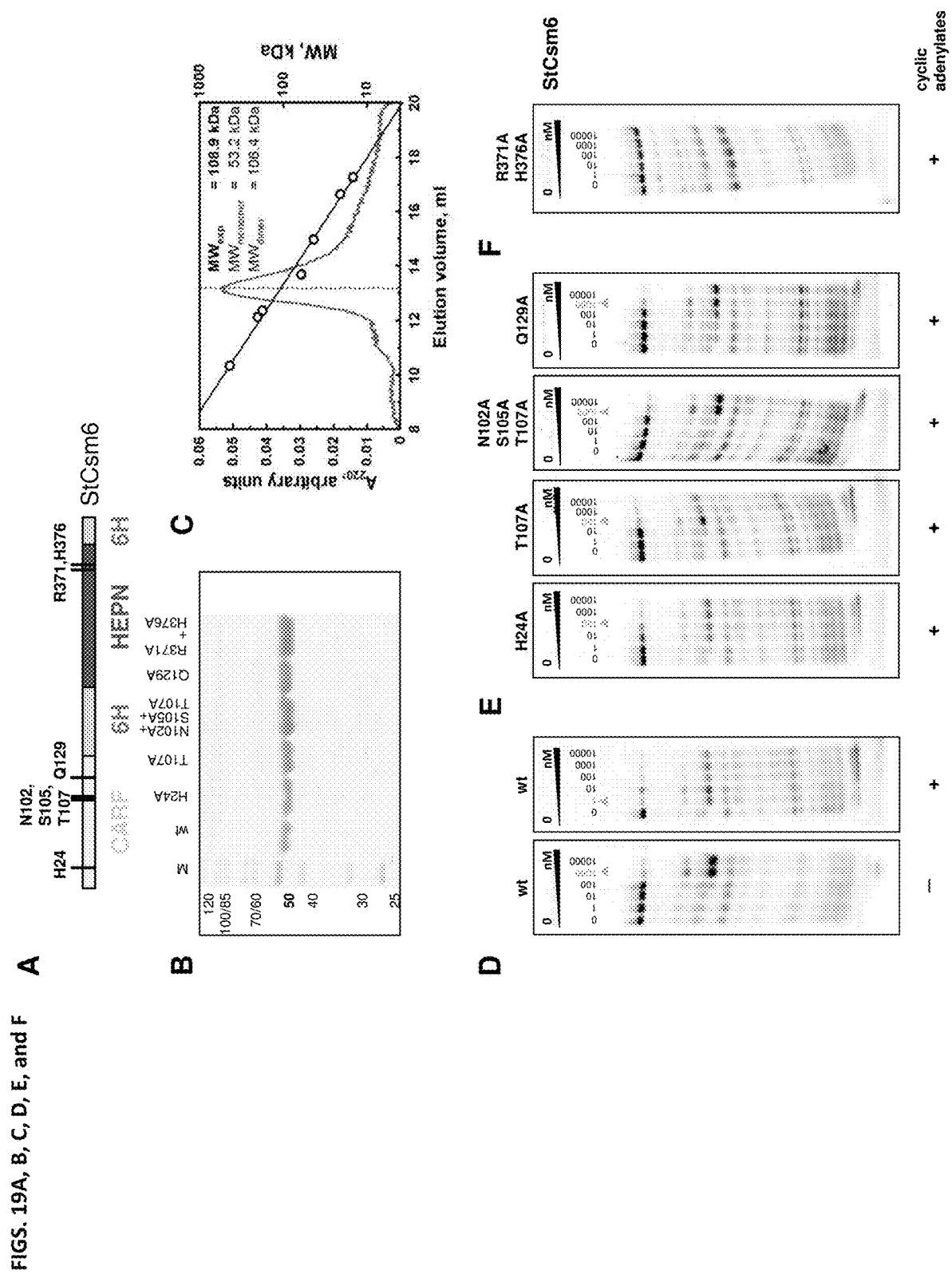
FIGS. 19A, B, C, D, E, and F show activation of StCsm6 ribonuclease by cyclic oligoadenylates.

FIG. 19 shows activation of StCsm6 ribonuclease by cyclic oligoadenylates. (FIG. 19A) Domain arrangement of StCsm6. Conserved residues characteristic of the different domains and subject to alanine mutagenesis are indicated above the boxes. (FIG. 19B) SDS-PAGE analysis of the purified StCsm6, M—protein mass marker. (FIG. 19C) Size-exclusion chromatography. The elution profile of the StCsm6 is presented with the calculated experimental molecular weight 108.9 kDa, corresponding to protein dimer. The size markers are ferritin (398 kDa), catalase (226 kDa), aldolase (146 kDa), BSA (62.9 kDa), ovalbumin (47.6 kDa), chymotripsin (19.4 kDa), ribonuclease A (15.6 kDa). (FIG. 19D) Dependence of StCsm6 RNase activity on cyclic oligoadenylates. Nuclease assay was performed at 37° C. for 30 min in the Reaction buffer supplemented with 1 mM EDTA, 0-10 µM StCsm6 (at concentration indicated above each lane), and 10 nM 5'-$^{33}$P-labeled RNA NS, in the absence or presence of 0.5 µM of the mixture of cyclic oligoadenylates, produced by StCsm. Samples were analyzed in denaturing PAAG, followed by phosphorimaging. (FIG. 19E) RNase activity of StCsm6 CARF mutants. Reaction conditions as in (FIG. 19D). (FIG. 19F) RNase activity of StCsm6 HEPN mutant. Reaction conditions as in (FIG. 19D). In the absence of cyclic oligoadenylates, StCsm6 degrades RNA only at high excess concentrations (1 µM). Addition of mixture of different cyclic oligoadenylates activates StCsm6 RNase (which then degrades RNA effectively at 1 nM). The lowest concentration of StCsm6 required for RNA degradation is indicated by a triangle.

Figure 20:
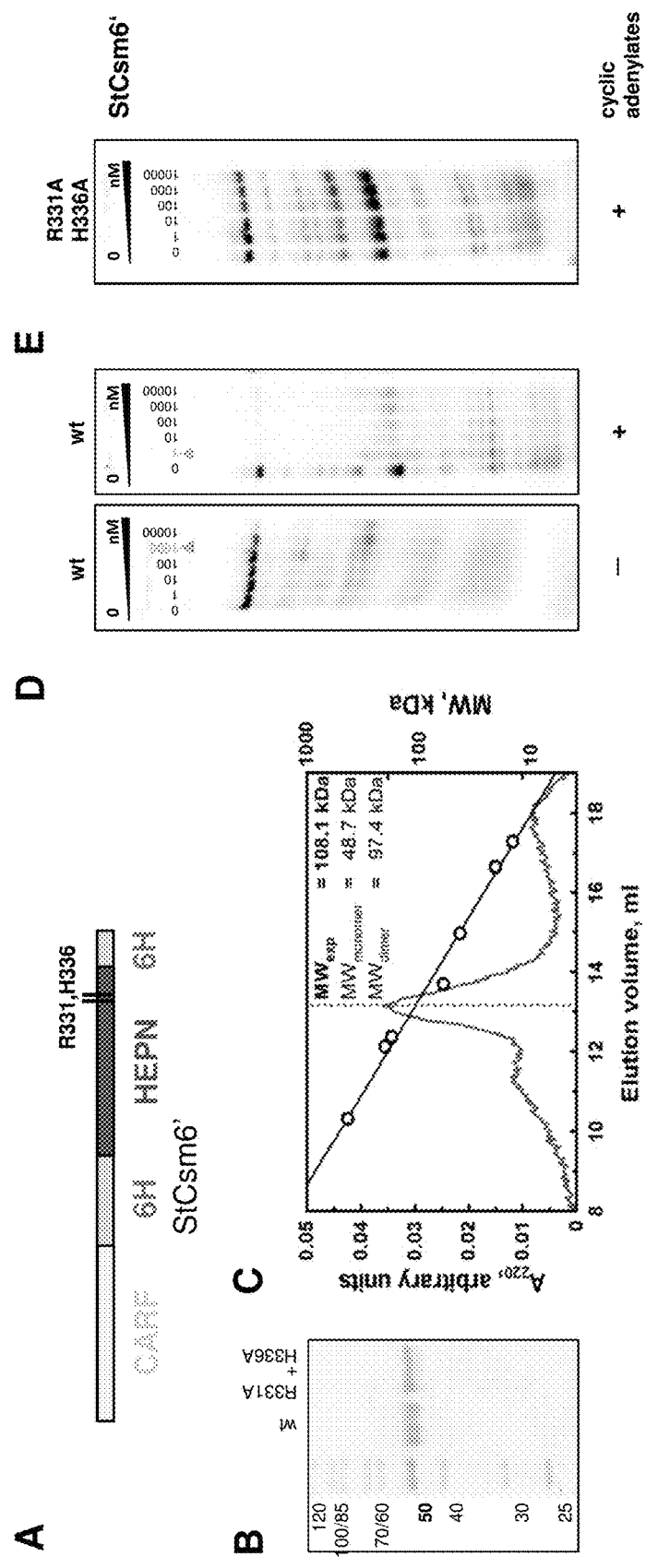
FIGS. 20A, B, C, D, and E show activation of StCsm6' ribonuclease by cyclic oligoadenylates.

FIG. 20 shows activation of StCsm6' ribonuclease by cyclic oligoadenylates. (FIG. 20A) Domain arrangement of StCsm6'. (FIG. 20B) SDS-PAGE analysis of the purified StCsm6', M-protein mass marker. (FIG. 20C) Size-exclusion chromatography. The elution profile of the StCsm6' is presented with the calculated experimental molecular weight 108.1 kDa, corresponding to protein dimer. The size markers are ferritin (398 kDa), catalase (226 kDa), aldolase (146 kDa), BSA (62.9 kDa), ovalbumin (47.6 kDa), chymotripsin (19.4 kDa), ribonuclease A (15.6 kDa). (FIG. 20D) Dependence of StCsm6' RNase activity on cyclic oligoadenylates. Nuclease assay was performed at 37° C. for 30 min in the Reaction buffer supplemented with 1 mM EDTA, 0-10 µM StCsm6' (at concentration indicated above each lane), 10 nM 5'-$^{33}$P-labeled RNA NS, in the absence or presence of 0.5 µM of cyclic oligoadenylates, produced by StCsm. (FIG. 20E) RNase activity of StCsm6' HEPN mutant. Reaction conditions as in (FIG. 20D). In the absence of cyclic oligoadenylates, StCsm6' degrades RNA only at high excess concentrations (1 µM). Addition of mixture of different cyclic oligoadenylates, same as for StCsm6, activates StCsm6' RNase (which then degrades RNA effectively at 1 nM). The concentration of StCsm, which is required for RNA degradation, is indicated by a triangle.

Figure 21:
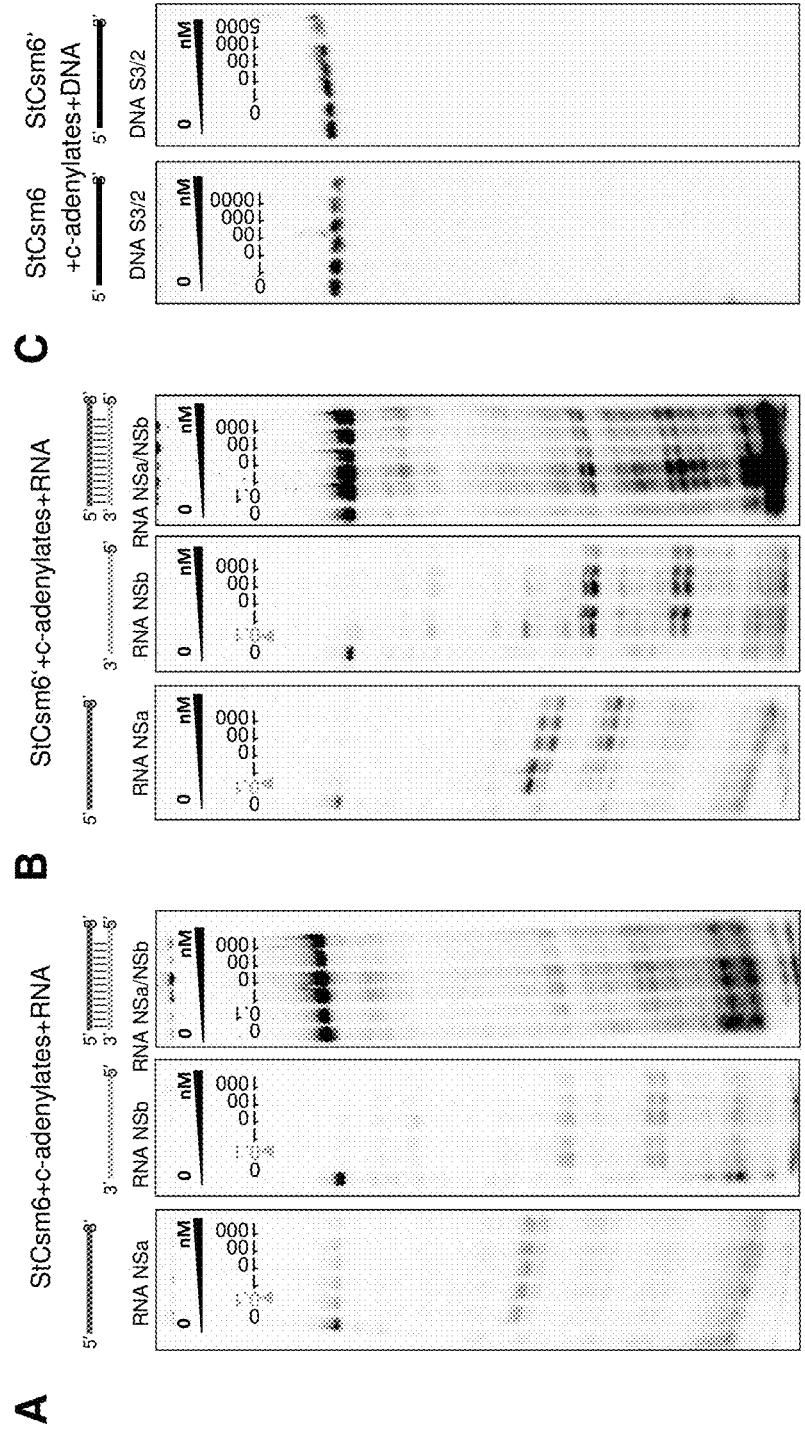
FIGS. 21A, B, and C show the nucleic acid specificity of StCsm6 and StCsm6' ribonucleases.

FIG. 21 shows the nucleic acid specificity of StCsm6 and StCsm6' ribonucleases. (FIG. 21A) Analysis of StCsm6 cleavage of dsRNA and corresponding ssRNAs in the presence of cyclic oligoadenylates. Nuclease assay was performed at 37° C. for 30 min in the Reaction buffer supplemented with 1 mM EDTA, 0-10 µM StCsm6 (at concentration indicated above each lane), 10 nM 5'-$^{33}$P-labeled NA and 0.5 µM of the cyclic oligoadenylates. (FIG. 21B) Analysis of StCsm6' cleavage of dsRNA and corresponding ssRNAs in the presence of cyclic oligoadenylates. Reaction conditions as in (FIG. 21A). (FIG. 21C) ssDNA treatment with StCsm6 or StCsm6' in the presence of cyclic oligoadenylates. Reaction conditions as in (FIG. 21A). The sequences of NA substrates used in this assay are listed in Table 1. Cartoons above the gels depict substrates. The concentration of StCsm6, required for effective RNA degradation, is indicated by a triangle.

Figure 22:
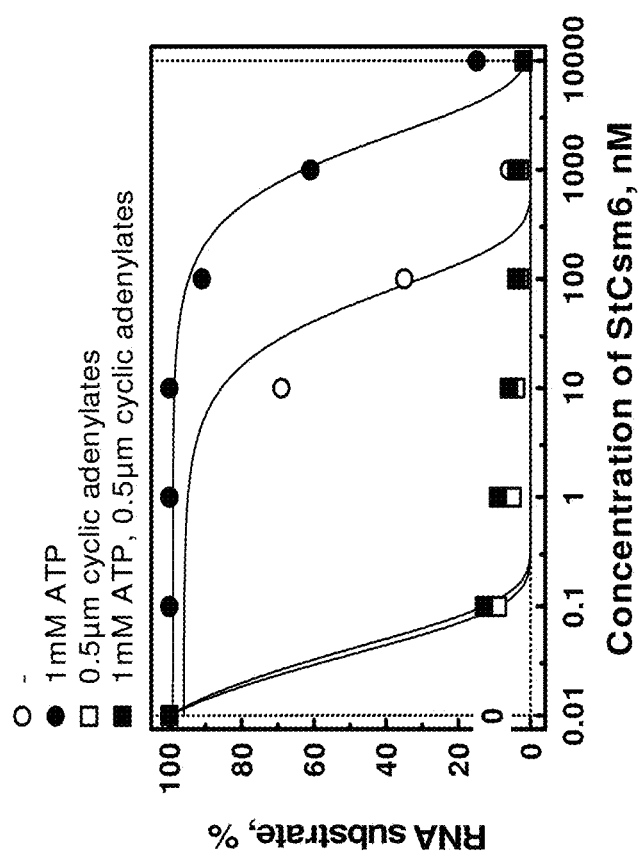
FIG. 22 shows that cyclic oligoadenylates rescue StCsm6 ribonucleolytic activity in the presence of inhibitory concentrations of ATP.

FIG. 22 shows that cyclic oligoadenylates rescue StCsm6 ribonucleolytic activity in the presence of inhibitory concentrations of ATP. StCsm6 RNase is inhibited by high (1 mM) ATP concentrations. Even a small amount (0.5 µM) of cyclic oligoadenylates rescues StCsm6 ribonucleolytic activity in the presence of inhibitory (1 mM) concentration of ATP. Nuclease assay was performed at 37° C. for 30 min in the Reaction buffer supplemented with 1 mM EDTA, 0-10 µM StCsm6 (at concentration indicated above each lane), 10 nM 5'-$^{33}$P-labeled RNA NS and the denoted amount of nucleotides. Samples were analyzed in denaturing PAAG, followed by phosphorimaging.

Figure 23:
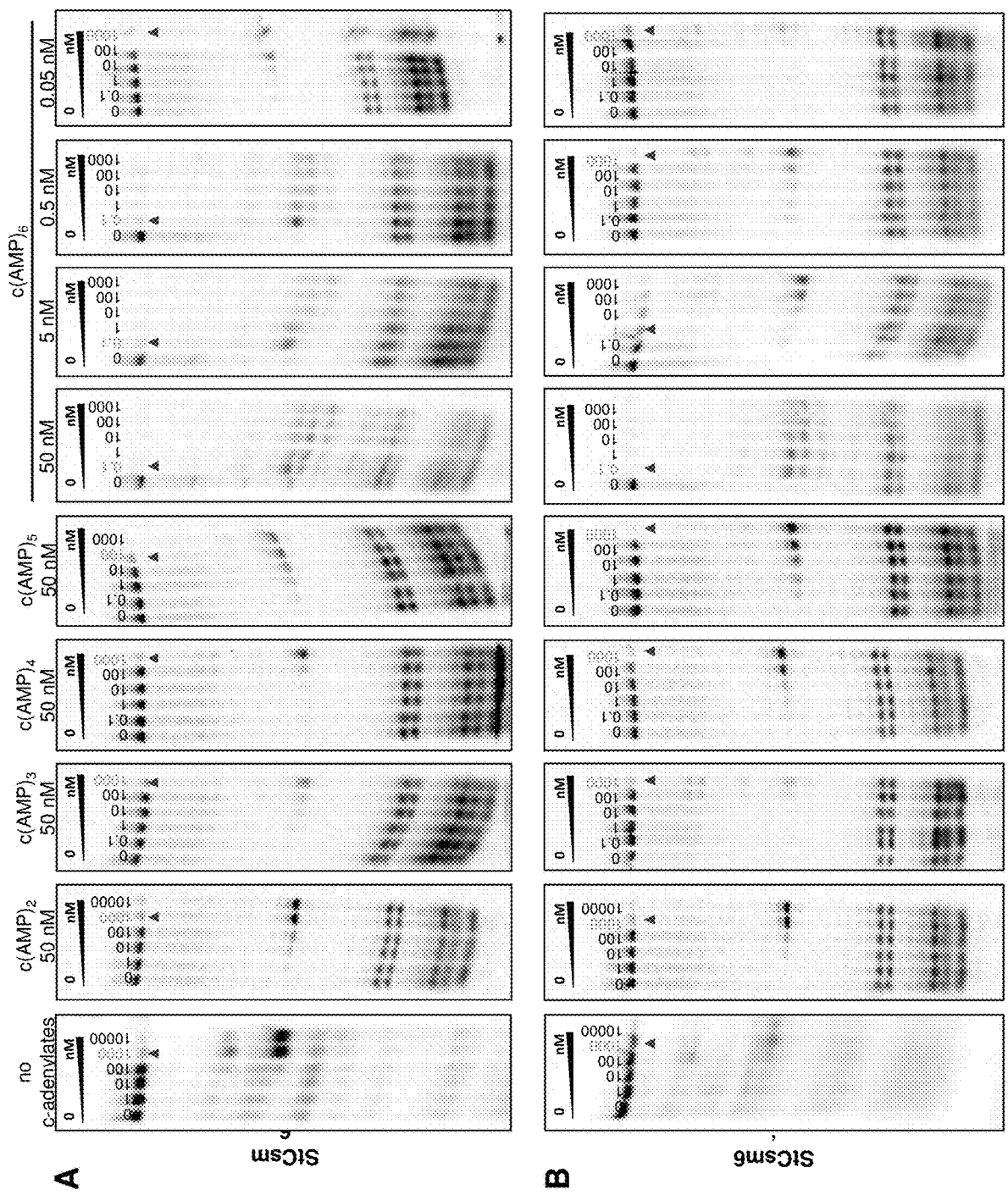
FIGS. 23A and B shows that $c(AMP)_6$ but not smaller cyclic oligoadenylates stimulates the StCsm6 and StCsm6' ribonucleases.

FIG. 23 shows that c(AMP)$_6$ but not smaller cyclic oligoadenylates stimulates the StCsm6 and StCsm6' ribonucleases. Analysis of StCsm6 (FIG. 23A) and StCsm6' (FIG. 23B) cleavage of ssRNA NS in the absence or presence of synthetic c(AMP)$_2$ (c-di-AMP) (Sigma-Aldrich) or HPLC isolated c(AMP)$_3$, c(AMP)$_4$, c(AMP)$_5$ (synthesized by StCsm from ATP) or c(AMP)$_6$ (synthesized by StCsm from pp(pA)$_6$ precursor). Nuclease assay was performed at 37° C. for 30 min in the Reaction buffer supplemented with 1 mM EDTA, 0-10 µM StCsm6 or StCsm6' (at concentration indicated above each lane), 5 nM 5'-$^{33}$P-labeled and 5 nM unlabeled RNA NS and 50 nM of the indicated cyclic oligoadenylate (unless indicated otherwise above the gel). Samples were analyzed in denaturing PAAG, followed by phosphorimaging. The concentration of StCsm6 or StCsm6', which is required for effective RNA degradation, is indicated by triangle.

Figure 24:
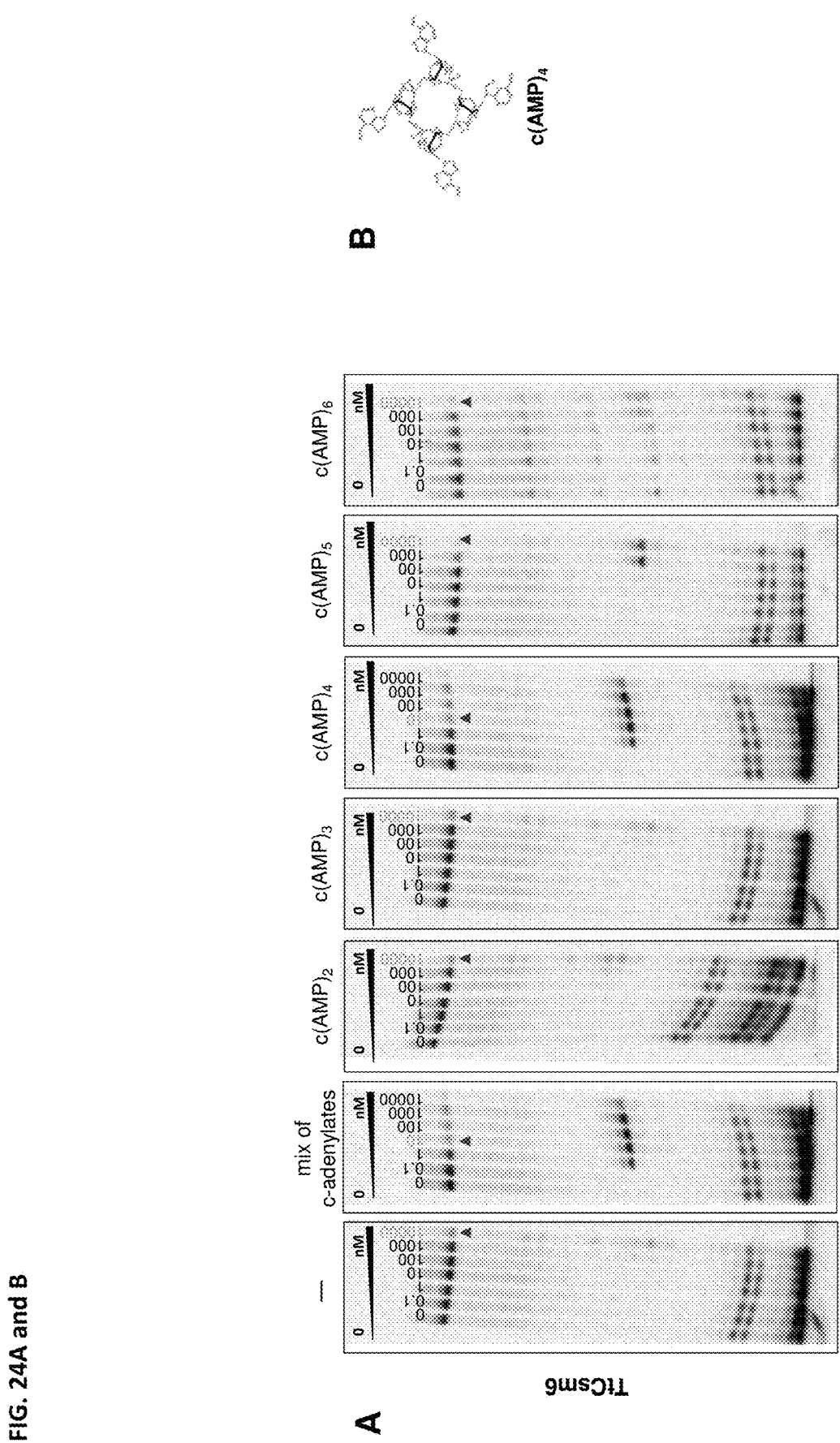
FIGS. 24A and B shows that $c(AMP)_4$ stimulates the TtCsm6 ribonuclease.

FIG. 24 shows that c(AMP)$_4$ stimulates the TtCsm6 ribonuclease. (FIG. 24A) Analysis of TtCsm6 cleavage of ssRNA NS in the presence of synthetic c(AMP)$_2$ (c-di-AMP)

(Sigma-Aldrich) or HPLC isolated c(AMP)$_3$, c(AMP)$_4$, c(AMP)$_5$ (synthesized by StCsm from ATP) or c(AMP)$_6$ (synthesized by StCsm from pp(pA)$_6$ precursor). Nuclease assay was performed at 37° C. for 30 min in the Reaction buffer supplemented with 1 mM EDTA, 0-10 µM StCsm6 or StCsm6' (at concentration indicated above each lane), 5 nM 5'-$^{33}$P-labeled and 5 nM unlabeled RNA NS and 500 nM of the indicated cyclic oligoadenylate. Samples were analyzed in denaturing PAAG, followed by phosphorimaging. The concentration of TtCsm6, which is required for effective degradation of RNA, is indicated by a triangle. (FIG. 24B) c(AMP)$_4$ is the activator molecule of TtCsm6 ribonuclease.

Figure 25:
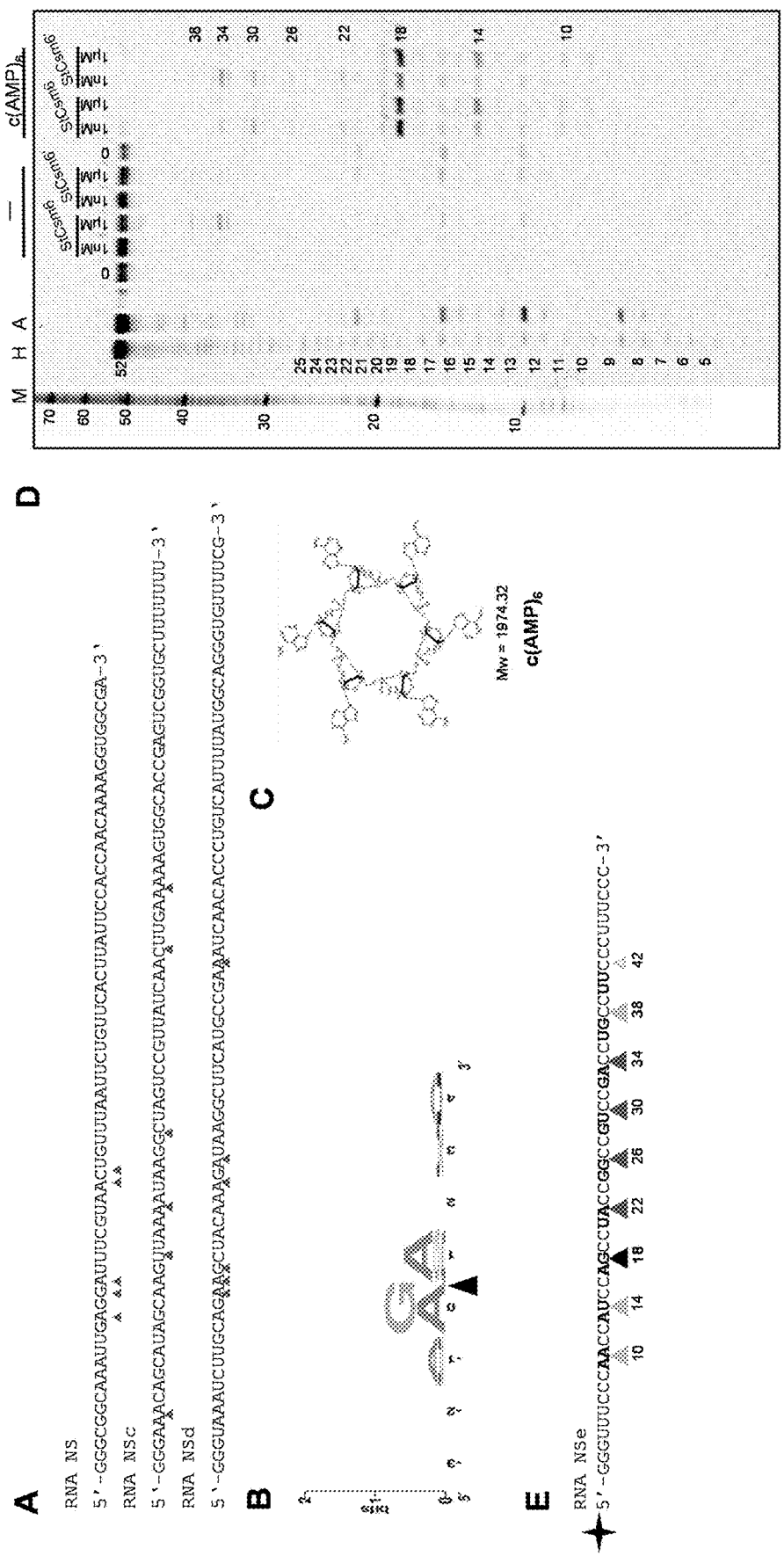
FIGS. 25A, B, C, D and E show sequence specificity of StCsm6 and StCsm6'; RNA NS (SEQ ID NO: 11), RNA NSc (SEQ ID NO: 12), RNA NSd (SEQ ID NO: 13, and RNA Nse (SEQ ID NO: 15).

FIG. 25 shows sequence specificity of StCsm6 and StCsm6'. (FIG. 25A) RNA substrates used in this assay. Mapped StCsm6 cleavage positions are indicated by triangles. (FIG. 25B) WebLogo of StCsm6 (1 µM) ribonuclease cleavage patterns of the oligonucleotides listed in (FIG. 25A) in absence of cyclic oligoadenylates. (FIG. 25C) c(AMP)$_6$ is the activator molecule of StCsm6 ribonuclease. (FIG. 25D) Analysis of StCsm6 and StCsm6' cleavage products of ssRNA NSe (SEQ ID NO: 15), which contains all possible variations of dinucleotide sequences. Nuclease assay was performed at 37° C. for 30 min in the Reaction buffer supplemented with 1 mM EDTA, 0-1 µM StCsm6 or StCsm6' (at concentration indicated above each lane), 5 nM 5'-$^{33}$P-labeled and 5 nM unlabeled RNA NSe and 5 nM of c(AMP)$_6$ (synthesized by StCsm from pp(pA)$_6$ precursor), if indicated. The samples were analyzed in denaturing PAAG, with RNA Decade marker (Ambion) (M, first lane), RNA NSe alkaline hydrolysis marker (H, second lane) and RNA NSe partial RNase A (ThermoFisher) digest (A, third lane) for reference. Numbers denote the length of adjacent RNA fragments. (FIG. 25E) Sequence of RNA NSe with mapped StCsm6 and StCsm6' cleavage positions (indicated by triangles). Both StCsm6 and StCsm6' exhibit similar specificities.

Figure 26:
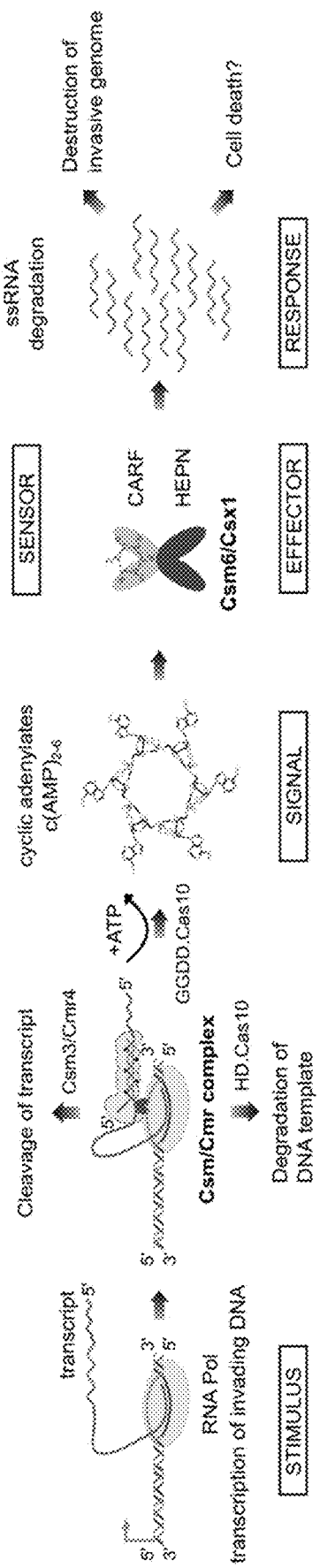
FIG. 26 is a schematic overview of inventive embodiments.

FIG. 26 shows the mechanism of cyclic oligoadenylate signaling in Type III CRISPR-Cas system. Binding of the target RNA sequence guided by the crRNA of the Cas10-containing complex triggers the three activities of the complex: (i) Csm3/Cmr4-mediated cleavage of the transcript itself, (ii) degradation of the corresponding invading DNA by the HD domain of Cas10, and (iii) synthesis of cyclic adenylates from ATP, carried out by the Palm domain of Cas10. The resultant cyclic adenylate is a signaling molecule that is recognized by the sensory CARF domain in Csm6, which in turn activates the effector HEPN domain of Csm6. Thus activated Csm6 effectively degrades ssRNA, which could buy the time necessary to ensure the destruction of invasive genome or eventually lead to cell death.

FIG. 27 shows that under certain conditions linear instead cyclic oligoadenylates could be used for stimulation of Csm6 ribonucleases. (FIG. 27A) Analysis of StCsm6 cleavage of ssRNA NS in the presence of linear hexa-adenylate with various phosphorylation levels (pp(pA)$_6$ (ChemGenes); (Ap)$_6$, (Ap)$_5$A (Metabion); (pA)$_6$). Nuclease assays were performed at 37° C. for 30 min in the Reaction buffer supplemented with 1 mM EDTA, 0-1 µM StCsm6 (at concentration indicated above each lane), 5 nM 5'-$^{33}$P-labeled and 5 nM unlabeled RNA NS and 500 nM of the indicated oligoadenylate (unless indicated otherwise above the gel). Samples were analyzed in denaturing PAAG, followed by phosphorimaging. (FIG. 27B) Analysis of StCsm6 cleavage of ssRNA NS in the presence of linear hexa-adenylate with various phosphorylation levels (pp(pA)$_4$ (ChemGenes); (Ap)$_4$, (Ap)$_3$A (Metabion); (pA)$_4$). Nuclease assays were performed as in (FIG. 27A). The concentration of StCsm6 or TtCsm6, which is required for RNA degradation, is indicated by triangle.

I. Synthesis of Oligoadenylates

In the Type III CRISPR-Cas systems, multiple Cas proteins and crRNA assemble into Csm (Type III-A) or Cmr (Type III-B) silencing complexes that provide interference against invading nucleic acids (1, 2, 9-13). Csm/Cmr complexes function as RNA-activated single-stranded (ss) DNases that ensure the destruction of foreign genetic elements while avoiding the degradation of a host's own DNA (1, 10-11, 14-15). When transcription of phage DNA is initiated, Csm/Cmr complex, guided by the crRNA, recognizes a complementary target (called a protospacer) in the nascent phage RNA. The RNA transcript binding by the Csm/Cmr complex triggers target RNA cleavage by Csm3/Cmr4 subunits and simultaneously activates the ssDNase activity of the Cas10 subunit for in cis degradation of ssDNA in the transcription bubble. Type III CRISPR-Cas systems avoid autoimmunity by checking the complementarity between the crRNA 5'-handle that originates from the repeat and the 3'-sequence flanking the protospacer in RNA target. Base-pairing between the crRNA 5'-handle and target RNA represses the Cas10 ssDNase activity thus protecting the host DNA from degradation. Non-complementarity of the crRNA 5'-handle to the RNA target in the phage RNA signals of a non-self DNA template and activates the Cas10 ssDNase for degradation (16). The temporal control of ssDNA degradation by the StCsm complex is achieved through the target RNA cleavage.

Cas10 subunit (called Csm1 and Cmr2 in the III-A and III-B systems, respectively) contains an N-terminal HD-domain, two small a-helical domains, and two Palm domains that share ferredoxin-like fold with the core domain of nucleic acid polymerases and nucleotide cyclases (17-19). Cas10 contains two putative active sites: the nuclease active site in HD-domain and the GGDD-(SEQ ID NO: 1)motif in one of the Palm domains (16). Whereas by now there is a consensus that the nuclease activity of the HD-domain is responsible for the ssDNA cleavage in vitro, the role of the GGDD-(SEQ ID NO: 1) motif of the Cas10 Palm domain in Type III-mediated DNA silencing has remained uncertain. This motif is essential for DNA interference in vivo and in vitro by Staphylococcus epidermidis Csm (SeCsm) complex (12, 20) but is dispensable for the in vitro ssDNase activity of Csm complex of Streptococcus thermophilus (StCsm) (1), Thermus thermophilus (TtCsm) (14) and Cmr complex of Pyroccocus furiosus (PfCmr) (10). The crystal structures of P. furiosus Cas10 (PfCas10) alone and the PfCas10/Cmr3 subcomplex show a single ADP, 3'-AMP or two ATP molecules coordinated together with divalent metal ions by amino acid residues of the GGDD-(SEQ ID NO: 1) and P-loop motifs in the Palm domains (18). The conservation of the complete set of catalytic residues typical of Palm domain polymerases and cyclases implies that the Palm domain of Cas10 should be enzymatically active but the nature of this activity has remained unknown. The possible ATP-related enzymatic activity of S. thermophilus DGCC8004 Cas10 (StCas10) from a Type III-A CRISPR-Cas system was thus investigated.

StCas10 alone or in the context of the binary StCsm complex [Cas10$_1$:Csm2$_3$:Csm3$_5$:Csm4$_i$:Csm5$_i$:crRNA(40 nt)] shows no ATPase or ATP cyclase activity (FIGS. 1A and 1B). However, ternary StCsm complex, comprised of binary complex bound to target RNA, converts ATP into a product that migrates faster than ATP but slower than ADP during thin-layer chromatography (TLC) (FIG. 1D). M13 mp18 ssDNA, which is subject to the HD-domain mediated hydrolysis (1), has no effect on the conversion of ATP to the reaction product (FIGS. 1C and 1E). Moreover, the D33A mutation in Csm3 protein, which prevents target RNA cleavage by StCsm complex but not target RNA binding (2), does not impair this ATP reaction (FIG. 2). Therefore, StCsm-mediated conversion of ATP to the reaction product requires target RNA binding but not target RNA cleavage. Taken together, these data indicate that formation of a ternary StCsm complex, which includes target RNA, is the only prerequisite for the StCsm-mediated ATP reaction. Notably, only target RNAs S3/2 or S3/14, which are complementary to the crRNA spacer but not to the crRNA 5'-handle, stimulate ATP conversion to the product (FIG. 3B). Complementarity between the 3'-flanking sequence and the 5'-handle of the crRNA (target RNA S3/3) inhibited the ATP reaction. Double mismatches in the target RNA sequence (target RNAs S3/7, S3/9 and S3/15) and target RNA 3'-truncation (target RNA S3/10) but not 5'-truncation (target RNA S3/14) impaired the ATP reaction (FIG. 3B). Intriguingly, the requirements for the target RNA molecule to promote the StCsm activity on ATP are similar to the rules that govern the ssDNase activity of StCsm (1). Moreover, similar to ssDNA degradation, temporal control of StCsm-mediated ATP reaction, is achieved through the target RNA cleavage (FIG. 2).

The ATP reaction, like the DNase activity of the StCas10 HD-domain (1), can be switched on or off depending on the non-complementarity/complementarity of the crRNA 5'-handle to the 3'-flanking sequence of target RNA (FIG. 3). Importantly, the D16A mutation that compromises ssDNA degradation by the StCas10 HD domain has no effect on the ATP reaction (FIG. 4) while D575A+D576A mutation in the GGDD motif of the StCas10 Palm domain abrogates ATP conversion into the reaction product (FIG. 4). Therefore, StCsm-mediated conversion of ATP to the reaction product is dependent on the GGDD (SEQ ID NO: 1) of Pol-domain and not on the HD active site of StCas10. The ATP reaction, catalyzed by the GGDD-(SEQ ID NO: 1) domain of StCas10, is dependent on $Mn^{2+}$, $Co^{2+}$, or $Zn^{2+}$ ions (FIG. 5). Taken together, these data demonstrate that the GGDD (SEQ ID NO: 1) motif of the StCas10 subunit in StCsm is responsible for metal-dependent ATP conversion into the reaction product and the reaction is critically dependent on the non-complementarity/complementarity of the crRNA 5'-handle to the 3'-flanking sequence of target RNA.

The Palm domain of StCas10 subunit in StCsm tightly binds adenosine-containing nucleotides ATP and 3'dATP with $K_d$ ranging from 10 to 20 nM in the presence or absence of target RNA but shows no significant affinity towards UTP, GTP and CTP (FIG. 6). Double D575A+D576A mutation in the GGDD (SEQ ID NO: 1) domain compromises ATP binding (FIG. 4C). 2'dATP is bound by the binary StCsm complex with the similar affinity as ATP or 3'dATP; however, target RNA binding into the ternary StCsm complex visibly decreases 2'dATP binding affinity (FIG. 6). Not surprisingly, no reaction products are formed when GTP, UTP, or CTP are used instead of ATP (FIG. 7). Unlike ATP, 3'dATP alone does not produce any reaction products while 2'dATP reacts with significantly lower efficiency (FIG. 7); however, all three of them cross-react with AMP to form respective dinucleotides (FIG. 8). Notably, AMP alone yields no products (data not shown). This suggests that StCas10 has at least two adenosine binding pockets that may have slightly different nucleotide binding modes as revealed by the crystal structures of PfCas10 (21). In the case of AMP reactions, one pocket presumably accommodates AMP, while another binds ATP, 2'dATP or 3'dATP, respectively. In conclusion, these experiments reveal following minimal substrate requirements for the reactions catalyzed by the StCas10 Palm domain: i) it should contain Ade; ii) 3'-OH in one nucleotide is required for the reaction to occur; iii) the other nucleotide should contain a triphosphate moiety.

II. Purification of Oligoadenylates

HPLC and ESI-MS analyses were performed to identify the reaction product obtained in the ATP reaction catalyzed by the StCsm complex. The major ATP reaction product (63.6%) showed molecular mass of 987.15 Da (FIG. 9). Such Mw could correspond to either cyclic or linear (containing 2',3'-cyclic phosphate) adenosine monophosphate (AMP) trinucleotide (tri-adenylate). The reaction product mix also contained compounds with Mw 1316.20 (corresponding to either cyclic or linear tetra-adenylate, yield 17.7%), Mw 1645.25 (corresponding to either cyclic or linear penta-adenylate, 8.0%) as well as traces of Mw 1974.31 (corresponding to either cyclic or linear hexa-adenylate, 0.5%), MW 1005.16 (pApApA or ApApAp, 1.0%) and Mw 836.04 (pppApA or ppApAp or pApApp or ApAppp, 4.0%) (FIG. 9). MW 1085.13 (ppApApA, ApApApp or pApApAp), Mw 676.11 (pApA or ApAp) and Mw 658.11 (corresponding to either cyclic or linear di-adenylate) were also observed, collectively constituting the remaining 5.2%. It was hypothesized that pppApA is a putative intermediate product, resulting from initial reaction between two ATP molecules, while ppApApA and pApApA could originate from pppApApA (same as pApA from pppApA), a putative product of StCsm-mediated reaction between ATP and pppApA.

HPLC was used to isolate individual ATP reaction products. HPLC was performed at room temperature on Waters Breeze HPLC system using a Discovery HS C18 Column (15 cm×10 mm, 5 µm) (Sigma-Aldrich Supelco), pre-equilibrated with buffer A (100 mM TEAA (pH 7.0)). Samples were loaded and fractionated at 1 ml/min flow rate with a linear gradient of B (60% $CH_3CN$ in buffer A) in A (0%-100% of B over 100 ml). Three separate peaks were isolated (FIG. 10A). Fractions containing different oligoadenylates were pooled and the samples were concentrated by a vacuum concentrator (Eppendorf). The purified samples were analyzed on an integrated HPLC/ESI-MS system (1290 Infinity, Agilent Technologies/Q-TOF 6520, Agilent Technologies) (FIG. 10B). Peak 1 contained compound of MW 1316.21 Da, corresponding to cyclic or linear tetra-adenylate. Peak 2 contained compound of MW 987.15, corresponding to cyclic or linear tri-adenylate. Peak 3 contained compound of MW 1645.25, corresponding to cyclic or linear penta-adenylate, with traces of Mw 658.11 (corresponding to cyclic or linear di-adenylate), 987.15 (corresponding to cyclic or linear tri-adenylate), 1316.21 (corresponding to cyclic or linear tetra-adenylate), 1974.37 (corresponding to cyclic or linear hexa-adenylate). Thus, separate oligoadenylates produced by the StCsm complex were able to be purified using HPLC.

III. Structure of Oligoadenylates

The reaction products of the ATP reaction were identified. HPLC-MS analysis revealed that StCsm converts ATP to the products with Mw 987.15 Da, 1316.20 Da, 1645.25 Da and 1974.31 Da (FIGS. 9A-9C). There are two possible compounds that have these masses: linear oligoadenylates with 2',3'-cyclic phosphate or cyclic oligoadenylates, respectively (FIG. 9D). Cyclic adenylates could be generated by ATP polymerization and cyclization into the oligoadenylate. FIG. 11 shows a proposed model for catalysis mechanism of such reaction by the StCas10 Palm domains. Cas10 protein, which is a part of the StCsm effector complex, possesses two ferredoxin-like fold domains P* and P, homologous to the Palm domain of nucleic acid polymerases and nucleotide cyclases. While one of the Palm domains appears to be catalytically inactive and the other has a putative active site featuring the conserved GGDD-(SEQ ID NO: 1) motif, both of them could be capable of binding ATP molecules (21). ATP binding in the P site positions the 3'-OH for the nucleophilic attack on the αP atom of the ATP molecule bound in the P* site. After the initial reaction, the product could reposition between the Palm domains so that the 3'-hydroxyl group of pppApA dinucleotide could attack its own triphosphate moiety, yielding cyclic (c) $(AMP)_2$ (also known as c-di-AMP). Alternatively, the triphosphate moiety of pppApA dinucleotide could be bound in only one of the Palm domains and ready for attack by the 3'-hydroxyl group of a new ATP molecule. MW could correspond to ppApApA (1085.13 Da) and pApApA (1005.16 Da), which could result from traces of ADP and AMP in the reaction mixture or degradation of triphosphate tri-adenylate, supporting that a tri-adenylate intermediate (pppApApA) forms during the reaction. After this trinucleotide intermediate is assembled, there are two competing reaction pathways. Under the experimental conditions, formation of the $c(AMP)_3$ was a predominant reaction (FIG. 11 and FIG. 10, Peak 2). In such case the trinucleotide could reposition within the two Palm domains for an intramolecular cyclisation reaction, in which the 3'-hydroxyl group of trinucleotide pppApApA would attack the 5'-triphosphate group, resulting in formation of $c(AMP)_3$. Alternatively, the trinucleotide could polymerize further with another ATP molecule before the cyclisation reaction occurs, which would result in $c(AMP)_4$, $c(AMP)_5$, or $c(AMP)_6$ (FIG. 11 and FIG. 10, Peaks 1 and 3).

To confirm the reaction mechanism, linear precursor oligonucleotide triphosphates (pppApApA, $pp(pA)_4$, $pp(pA)_5$, $pp(pA)_6$) were synthesized and used as substrates for StCsm catalyzed cyclization reaction. Corresponding triphosphate oligoadenylates were mixed with the ternary StCsm complex in the Reaction buffer supplemented with 10 mM $CoCl_2$ and reaction products were analyzed by HPLC-MS. Upon treatment with wt StCsm, pppApApA was converted into $c(AMP)_3$ (FIG. 12A). Similarly, $pp(pA)_4$ was turned into $c(AMP)_4$, $pp(pA)_5$ was converted into $c(AMP)_5$, and $pp(pA)_6$ was converted into $c(AMP)_6$ (FIGS. 12B-12D). Therefore, triphosphate oligoadenylates are intermediates of the StCsm mediated ATP cyclisation reaction and can be converted to the cyclic-oligoadenylates by StCsm.

Further, the purified oligoadenylate compounds were subjected to various biochemical reactions and analyzed them with HPLC coupled with ESI-MS or in a denaturing PAAG. First, HPLC purified tri-adenylate, tetra-adenylate, penta-adenylate and hexa-adenylate were treated with P1 nuclease. P1 nuclease from *Penicillium citrinum* degrades ssRNA (and less efficiently ssDNA) to nucleoside 5'-monophosphates. Upon treatment with P1 nuclease, the oligoadenylates were processed entirely into AMP mononucleotides (FIGS. 13A, 13B and 13D). MS analysis confirmed that neither adenosine nor adenosine 2',3'-cyclic phosphate, which would result from P1 nuclease mediated hydrolysis of linear oligoadenylate with 2',3'-cyclic phosphate, are produced in this hydrolysis (FIG. 13C). This result suggests that the oligoadenylates are cyclic and not linear molecules containing 2',3'-cyclic phosphate. Treatment of the StCsm mediated ATP reaction products with nuclease PDE12, which exhibits exonuclease activity on 2',5'- and 3',5'-adenylates [5, 6], revealed that major product tri-adenylate of the StCsm mediated ATP reaction is resistant to this exonuclease (FIG. 14). Next, the ATP reaction products could not be labeled in the usual 5'-labeling reaction (FIG. 15B), supporting their cyclic structure. Moreover, the migration of the main product of the StCsm catalyzed ATP reaction (cyclic tri-adenylate) in the polyacrylamide gel differs significantly from migration of linear pApApA (FIG. 15A).

P1 nuclease exhibits high phosphomonoesterase activity toward 3',5'-ribonucleotides but 2',5'-ribonucleotides are extremely resistant to it (3, 4). The ATP reaction products were efficiently degraded by P1 (FIG. 13); therefore, it is likely that all three of their phosphodiester bonds are 3'-5'. This is further supported by the fact that 3'-OH but not 2'-OH is prerequisite for the reaction to occur (FIG. 7 and FIG. 8). StCsm catalyzed reactions of ATP and/or 2'dATP but did not produce any products when reactions contained only 3'dATP (FIGS. 8A-8C). However, all three above mentioned nucleotides cross-react with AMP to form respective dinucleotides (FIGS. 8A-8C). This implies that 3'-OH group in adenosine triphosphate is an attacking group in a nucleophilic attack forming 3'-5' phosphodiester bond in cyclic oligoadenylates.

Taken together, these data show that in the presence of target RNA the GGDD (SEQ ID NO: 1) active site in the Palm domain of Cas10 subunit in the StCsm ternary complex of a Type III-A CRISPR-Cas system catalyzes synthesis of cyclic oligoadenylates (FIG. 16). Small nucleotide-based compounds often act as signaling molecules in various organisms: cAMP and cGMP are key messengers in both bacteria and higher organisms; ppGpp and pppGpp act as alarmones in bacteria; nicotinic acid adenine dinucleotide phosphate (NAADP), adenosine diphosphoribose (ADPR) and cyclic ADP-ribose (cADPR) are involved in $Ca^{2+}$ regulation in higher eukaryotes; diadenosine polyphosphates $(Ap_{2-6}A)$ and 2',5'-oligoadenylates participate in certain mammalian immune responses (22). Therefore, it was hypothesized that the cyclic oligoadenylates, synthesised by StCsm complex of the Type III-A CRISPR-Cas system, could act as signaling molecules in an anti-phage defense pathway of bacteria. As in all the other described cases there are complementary proteins that act as sensors for the nucleotide-based messengers and generate the required response, there should be a corresponding sensory protein adjacent to the Type III-A CRISPR-Cas system.

IV. Cyclic Adenylates Activate CARF-Domain Ribonucleases

Many CRISPR-Cas systems are associated with genes that appear not to be directly implicated in spacer acquisition, CRISPR transcript processing or interference against invading nucleic acids (23-27; K. S. Makarova et al. The basic building blocks and evolution of CRISPR-CAS systems. Biochemical Society transactions 41 (2013), p. 1392-1400). For example, csm6 gene, that belongs to the COG1517 family [24-25], is associated with Type III-A CRISPR-Cas locus of *S. thermophilus* DGCC8004 strain. *S. thermophilus* StCsm6' and StCsm6 proteins do not belong to the StCsm effector complex that provides interference against invading nucleic acids (2). Bioinformatic analysis revealed that StCsm6 and StCsm6' proteins are related (~35% sequence identity) (16). They both have a typical Csm6 architecture, which includes the N-terminal CARF (CRISPR-asssociated Rossman fold) domain (FIG. 17), the middle α-helical "6H" domain and the C-terminal HEPN domain (nucleotide binding domain, characteristic to both prokaryotes and higher eukaryotes) (8, 28-29) (FIG. 18). Molecular modeling revealed that N-terminal CARF domains of both StCsm6 and StCsm6' are most similar to the corresponding domain of the TtCsm6 (PDB: 5FSH) (29) (FIG. 17). The middle (6H) and the C-terminal (HEPN) domains were found to be the most similar to the structure of Csm6 from *Streptococcus mutans* (PDB: 4RGP) (FIG.

18). Structural models reveal that the CARF domain in both StCsm6 and StCsm6' is highly similar. The largest difference between the two proteins is observed within the HEPN domain, which is more compact in StCsm6' (FIGS. 18D and 18E).

Previously, it was shown that activity of the TtCsm6 RNase resides in the composite active site formed by a pair of HEPN domains, whereas the interface of the CARF domains features a putative ligand-binding site (29). The putative binding site formed by CARF domains might be the site for binding the cyclic oligoadenylates, produced by Cas10 of the Csm complex; to test this, docking experiments were performed using the dimeric structure of TtCsm6 CARF domains as a receptor and adenosine as the ligand. The nucleoside over nucleotide was chosen to test the compatibility of shape with the putative binding site while at the same time avoiding potential complications due to the electrostatic interaction between the nucleotide phosphate(s) and the positively charged cleft formed by the CARF domains. Docking revealed that two distinct pockets within the cleft can bind adenosine (FIG. 17D). Since the TtCsm6 structure is a dimer, there is another symmetry-related pair of pockets. However, as the asymmetric unit in the crystal structure corresponds to a dimer, the two pairs of pockets are not identical. That could be the reason why the adenosine was docked only into the two and not all four pockets.

CARF domains of both StCsm6 and StCsm6' lack a couple of a-helices at the N-terminus compared to the CARF domain of TtCsm6 but otherwise are quite similar to it (FIGS. 17E and 17F). Therefore, the docking results for TtCsm6 were considered to perhaps be relevant to StCsm6 and StCsm6'. Based on StCsm6 and StCsm6' structural models residues corresponding to the two distinct pockets at the interface of CARF domains were identified, and those likely contributing to the nucleobase binding (His24 and Gln129 in StCsm6) were selected. In addition, three other conserved residues were selected that are involved in forming the bottom of the cleft (Asn102, Ser105 and Thr107 in StCsm6) (FIG. 17).

Domains belonging to the HEPN superfamily often exhibit ribonuclease activity and are commonly found in prokaryotic toxin-anti-toxin (T-A) and abortive infection (Abi) defense systems (30). It has been proposed that Csm6 and other CARF family proteins associated with the Type III CRISPR-Cas systems may degrade RNA transcripts of DNA invaders complementing the DNA- and RNA-targeting endonuclease activities of the Csm complex (8). Indeed, in S. epidermidis Csm6 protein is involved in the degradation of RNA transcripts for the late expressed viral genes (31). Alternatively, it was suggested that Csm6/Csx1 proteins could contribute to CRISPR immunity by targeting host (i.e., self) transcripts in order to induce dormancy or promote programmed cell death of the host (28, 29).

To understand the role of the Csm6' and Csm6 proteins in S. thermophilus immunity, StCsm6 (FIG. 19B) and StCsm6' (FIG. 20B) were expressed in heterologous E. coil host and purified. Both StCsm6 and StCsm6', like homologous SeCsm6, TtCsm6, and PfCsm6 proteins (29, 31), exhibited ssRNA degradation activity in a metal-independent manner (FIGS. 19D and 20D). Alanine replacement of the conserved putative active site residues (RXXXXH) (SEQ ID NO: 14) located in the HEPN domain impaired the ssRNase activity of StCsm6 and StCsm6' (FIGS. 19F and 20E). Notably, the StCsm6 and StCsm6' ssRNase activity was rather weak and observed only at high (micromolar range) protein concentrations. StCsm6 (and StCsm6') protein, like most of the other COG1517 family proteins, contains an N-terminal CARF domain that could act as a ligand sensor. It was hypothesized that cyclic oligoadenylates, produced by the StCsm complex, could act as a ligand for StCsm6 (StCsm6'). Indeed, the mixture of cyclic oligoadenylates effectively stimulated both StCsm6 and StCsm6' ssRNase activity, reducing the required protein concentration ~1000-fold (FIGS. 19D and 20D). Addition of cyclic oligoadenylates did not result in any hydrolysis dsRNA or ssDNA (FIG. 21), confirming StCsm6 and StCsm6' are ssRNA-specific nucleases. Mutation of conserved amino acid residues H24, N102, S105, T107 or Q129 in the putative ligand binding pocket in the CARF domain of StCsm6 significantly impaired ligand-stimulated ssRNase activity (FIG. 19E).

StCsm6, StCsm6' and TtCsm6 are homodimers in solution (FIGS. 19C and 20C) [29]. Homology model of the StCsm6 indicates that the ligand binding site is located at dimer interface of the CARF domains (FIG. 17). It is likely that cyclic oligoadenylate binding to the CARF domain induces structural rearrangements in the HEPN domain as well, thus stimulating the ssRNase activity of the StCsm6. This observation indicates that CARF domain of the Csm6 proteins acts a sensor for the ligand produced by the StCsm complex of the Type III-A CRISPR system. Biologically relevant ATP concentrations inhibit the StCsm6 RNase but its activity can be easily rescued by the cyclic adenylates (FIG. 22).

Next, it was determined which of the cyclic oligoadenylates, synthesized by the ternary StCsm complex, was the activator of the StCsm6 and StCsm6' nucleases. For this a synthetic $c(AMP)_2$ (c-di-AMP) was used and the compounds that isolated from StCsm ATP or triphosphate oligoadenylate reaction mixtures by HPLC: $c(AMP)_3$, $c(AMP)_4$, $c(AMP)_5$ and $c(AMP)_6$. Nuclease assays revealed that of all the cyclic adenylates tested, only $c(AMP)_6$ stimulated ribonuclease activity of StCsm6 and StCsm6' (FIG. 23). Even 0.5 nM (5 nM in case StCsm6') of $c(AMP)_6$ was sufficient for efficient StCsm6 ribonuclease activity.

To elucidate if cyclic oligoadenylates synthesized by Type III StCsm effector complex are universal activators for Csm6 proteins, considering the TtCsm6 ssRNase activity was also observed only at high (micromolar range) protein concentrations (29), it was examined in the presence of cyclic oligoadenylates, synthesized by the StCsm ternary complex. Only $c(AMP)_4$ stimulated TtCsm6 ribonuclease activity (FIG. 24). This is in agreement with the docking and structure modelling experiments that show four possible adenosine binding sites in the dimeric TtCsm6 CARF domain structure (FIG. 17D). Seemingly, the cyclic oligoadenylates are signaling molecules in various Type III CRISPR-Cas systems; however, the exact size of the active compound can vary between organisms.

To investigate whether StCsm6 and StCsm6' ribonucleases possess sequence specificity, cleavage of 5'-radiolabeled ssRNA substrates with random sequences (FIG. 25A) was analyzed. Initial analysis suggested preference for dinucleotide with different variation of purines (FIG. 25B). To test the sequence specificity further, RNA NSe oligonucleotide was synthesized containing all possible dinucleotide combinations, interspaced by a CC sequence. StCsm6 and StCsm6' cleavage of this substrate both in the absence and the presence of $c(AMP)_6$ was analyzed. In the absence of nucleotide effector and at high nuclease concentrations, residual cleavage was most prominently visible at GA dinucleotide (FIGS. 25A, 25B and 25E), as indicated by the initial analysis. Addition of $c(AMP)_6$ not only stimulated effective RNA NSe hydrolysis at low enzyme concentrations but also promoted cleavage at other positions, containing a purine nucleotide, especially AG (FIGS. 25E and 25F).

Smaller cyclic dinucleotides (c-di-GMP, c-di-AMP or cGAMP) across the three superkingdoms of life are often encountered as intracellular messengers that convey specific as well as global signals (32, 33). They are synthesized in a cell by specific enzymes in response to different stimuli and are recognized by sensor domains embedded within different effector proteins. For example, c-di-AMP is generated in response to direct sensing of endogenous branched DNA, making it a checkpoint regulator (34). In vertebrates, linear 2'-5' oligoadenylates (2'-5'A), ranging from 2 to 30 oligomers, are produced in response to sensing of double-stranded viral RNA and stimulate latent ribonucleases (RNaseL) for the degradation of the invading RNA (35). In prokaryotes, signaling systems utilizing cyclic di-nucleotides have been considerably well studied; however, systems centered on other oligonucleotides remained largely unknown. The data herein show that the cyclic hexa-adenylate $c(AMP)_6$ synthesized by Cas10 protein in the StCsm complex of the Type III-A CRISPR-Cas system in response to the target RNA recognition acts as a novel messenger that activates RNA degradation by Csm6 ribonuclease through binding to the sensor CARF domain (FIG. 26), thereby expanding the role of cyclic oligonucleotide signaling to prokaryotic defense systems.

V. Applications

The inventive method provides a basis for easy enzymatic synthesis of cyclic oligoadenylates under broad reaction conditions. In one embodiment, the synthesis reaction of cyclic oligoadenylates is conducted in vitro by the StCsm complex by adding 10 mM $CoCl_2$ into a mix of 200 nM StCsm, 200 nM target RNA, 50 µM ATP in the Reaction buffer (33 mM Tris-acetate (pH 7.9 at 37° C.), 66 mM K-acetate, 0.1 mg/ml BSA) and incubated at 37° C. for 1 h. If needed, reaction conditions could be changed: (i) incubation could be extended or reduced to a time more or less than one hour, for example, 15 minutes; or (ii) other bivalent metal ions could be used as cofactors, for instance, $Mg^{2+}$, $Mn^{2+}$, $Ni^{2+}$, $Zn^{2+}$ or $Fe^{2+}$ or (iii) both StCsm and target RNA concentrations could be changed, or (iv) different substrates could be used at various concentrations, e.g., 17 µM short 5'ppp oligoadenylates could be used instead of 50 µM ATP; or (v) different reaction buffers with different pH, ionic strength could be used. These compounds are stable and can be stored at +4° C. or −20° C. for months and re-thawed multiple times.

Ternary StCsm complex, comprised of Cas10, Csm2, Csm3, Csm4, and Csm5 proteins, a crRNA, and a target RNA transcript which is substantially complementary to a portion of the crRNA was employed. However, other complexes containing Cas10, such as Csm complexes from other organisms or related Cmr complexes (16), should be capable of a very similar if not identical activity. Therefore the invention is not limited to the complex used in the exemplary descriptions and other Cas10-containing complexes may be used in the described methods.

Given that the StCsm complex is capable of polymerizing two ATP molecules and the general mechanism of StCsm-mediated cyclic oligoadenylate synthesis (FIG. 11), it should be able to cyclize any RNA that has 5'-pppA and A-3'OH. 5'-pppRNAs-3'OH, are naturally occurring in abundance in prokaryotes, and obtained using in vitro transcription kits. Moreover, eukaryotic RNA also contains a triphosphate moiety at its 5' side and a 3'-polyA tail, which makes them potentially good targets for StCsm-mediated RNA cyclization reaction. Stability of RNA, especially when delivered to cell cultures, has always been an issue. It has been shown that cyclization of silencing RNA improves its stability (Abe et al., Dumbbell-shaped nanocircular RNAs for RNA interference. J Am Chem Soc. 129 (2007) p. 15108-15109). This could be extended to other RNAs, for example, stabilization of aptamers. Lately, circular RNAs have been established as a type of eukaryotic noncoding RNAs, involved in regulation of a number of cellular processes (Hsiao et al., New member of noncoding RNA with novel functions. Experimental Biology and Medicine (2017)). They have been implicated in neuronal, cardiovascular and oncogenic diseases; therefore their studies could shed more light on these conditions. For this, the described method for circular RNA synthesis, such as the Cas10-containing complex, would be of great use. Moreover, under described conditions StCsm complex also mediated synthesis of cyclic oligodeoxyadenylates, extending its applications to DNA as well.

Since the Cas10-containing complex was able to synthesize these molecules only in the presence of target RNA, the synthesis of cyclic oligoadenylates (or any cyclic nucleic acid synthesized in Cas10-dependent manner) could be used as a signal to report appearance of target nucleic acids in vitro and in vivo. Neither ssDNA nor dsDNA can cause the StCsm complex to synthesize cyclic compounds. However, known techniques can be used to transcribe a desired DNA and thus produce target RNA for the Cas10-containing complex based on a desired DNA. Thus the described method can be applied for not only RNA but also DNA detection in various samples. The appearance of cyclic oligoadenylates could be detected using, for example, mass spectrometry analysis.

We discovered that a family of CARF-containing nucleases can be activated by cyclic oligoadenylates. CARF-containing RNases Csm6 from different organisms are activated by differently sized cyclic oligoadenylates. Small amounts of cyclic oligoadenylates are required for efficient activation of CARF-containing RNases: 0.5 nM $c(AMP)_6$ for StCsm6, 5 nM $c(AMP)_6$ for StCsm6', 50 nM $c(AMP)_4$ for TtCsm6. However, we found that much higher amount of linear oligoadenylates can also activate these proteins (FIG. 27). While the RNA degradation is essentially non-specific, StCsm6 and StCsm6' show preference for purine sites. Stimulated by cyclic oligoadenylates, StCsm6 is able to degrade ssRNA at subnanomolar concentrations. In general, signaling systems have a way to remove the effector molecule. Removal of cyclic oligoadenylates would inactivate this enzyme. For example, the oligoadenylates are degradable by nuclease P1 (FIG. 13). Therefore, CARF-containing RNases can be used to remove RNA from various samples in a controllable fashion. Given the nature and size of the cyclic oligoadenylates, this could allow initiation of total cell RNA degradation in cells as well as complete ssRNA hydrolysis in vitro. Often the CARF domain is found combined with different RNases, such as members of the RelE (23) and HEPN families (30) suggesting that other RNases could also be activated for RNA degradation in vitro and in vivo by cyclic or linear oligoadenylates similar to Csm6.

Naturally, the cyclic adenylates, required for activation of CARF-containing proteins, can be synthesized by the previously described enzymatic synthesis, using a Cas10-containing complex. CARF-containing protein can be coupled with Cas10-containing complex to create a unique system for in vitro platforms and in vivo tools. For instance, such system could be used for detection of selected nucleic acids, e.g., viral transcripts, in a manner similar to the SHERLOCK platform (36). In vivo such system could be used to induce cell dormancy at desired time and/or desired cell by choosing an appropriate target transcript. This target transcript could appear at certain stage of cell cycle or under certain other conditions. The system allows assaying the cellular content upon emergence of the selected target transcript. Alternatively, the system could be used to distinguish between cells that transcribe the target sequence (either constitutively or occasionally) from the target-free cells. The system could be applied to induce cell suicide in response to a foreign or malignant transcript, e.g., viral or lethal.

For in vivo applications all the necessary components could be delivered to the cells either as DNA, RNA, or proteins, or any combination of them, by transformation, electroporation, transfection, etc. Genes encoding the necessary components could also be integrated into the genome of desired cells. When delivered in DNA form, the expression of system components could be inducible or constitutive, depending on the need. The target transcript, which is substantially complementary to a portion of the crRNA, could be (i) delivered as DNA (for instance, expressed from an expression plasmid), (ii) delivered as RNA, (iii) emerge after infection (for instance, viral) of the cell culture, or (iv) any endogenous gene product or non-coding RNA of the cell could be selected as a target. In embodiments, in the case of eukaryotic cells, the expression of these components would be optimized.

Other CRISPR-Cas systems possess Csm6 analogues, such as Csx1 (28, 40). CARF domains occur fused not only to RNases but also DNases, membrane-associated protein domains, TIM barrel adenosine deaminase Ada domain (8) and more domain combinations might be found. It is likely that such proteins could be allosterically regulated by cyclic oligoadenylates or similar compounds; expanding the inventive methods to their regulation. Therefore, while *S. thermophilus* and *T. thermophilus* Csm6 proteins are used in the above exemplary descriptions, the invention is not limited to this source of proteins and other proteins may be used in the described methods.

We demonstrated here that cyclic or linear oligoadenylates could be used to activate ribonucleolytic activity of different Csm6 proteins through stimulation of their CARF-domain. Often the CARF domain is found combined with different effector domains. Most of the CARF domain proteins contain a winged HTH (wHTH) DNA-binding domain immediately C-terminal of CARF, for example in CRISPR-Cas associated protein Csa3 (8, 41). It has been suggested that such proteins are allosterically controlled transcriptional regulators (41). Therefore, CARF-containing DNA-binding proteins could be used to regulate gene expression in a variety of both prokariotyc and eukaryotic cells using cyclic or linear oligoadenylates.

Many CARF-domain proteins possess additional not only RNase, but also DNase domains, in particular those of the restriction endonuclease, for example protein VC1899 from *Vibrio cholera* (8, 25). Therefore, CARF-containing DNases could be used specifically to cleave target DNA seguence or non-specifically to remove DNA from various samples in a controllable fashion in vitro and in vivo.

CARF domains are also found in RtcR proteins, sigma-54 RNA polymerase dependent regulators of the rtcBA tRNA and mRNA splicing and repair operon (8, 42, 43). Binding of RtcR protein near promoter of rtcBA activates transcription of two proteins, RNA ligase RtcB (44) and 3'-terminal phosphate RNA cyclase RtcA (45). It was demonstrated that in *Escherichia coli* bacteria expression of rtcAB is activated by agents and genetic lesions which impair the translation apparatus (42). Therefore, CARF-containing RtcR-like protein could be used to regulate protein translation in a variety of both prokariotyc and eukaryotic cells using cyclic or linear oligoadenylates.

Sometimes CARF domain is fused to a TIM barrel adenosine deaminase Ada domain the enzyme that catalyzes deamination of adenosine to inosine in the purine salvage pathway (8). Therefore, CARF-containing deaminase protein could be fused to Cas9 or Cpf1 cleavage deficient or nicking variants to engineer base editor regulated with cyclic or linear oligoadenylates via CARF-domain in vitro and in vivo.

TABLE 1

Nucleic acid substrates used *

| | | |
|---|---|---|
| S3 crRNA in StCsm complex | Spacer S3        5'-handle<br>3'-CUUAUUCACUUGUCUUAAUUUGUCAAUGCUUUCAAAGGCA-5' (SEQ ID NO: 16) | |

| Target RNA | Description | Sequence |
|---|---|---|
| RNA S3/2 | single stranded activator | \|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>5'-GGGAUCCCCAAAUAUAAGGUGGAAUAAGUGAACAGAAUUAAACAGUUACGAAAAAAAAAAAGGGUACC-3'<br>(SEQ ID NO: 17) |
| RNA S3/3 | RNA 68-mer containing 32 nt | \|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>5'-GGGAUCCCCAAAUAUAAGGUGGAAUAAGUGAACAGAAUUAAACAGUUACGAAA<u>GUUUCCGU</u>GGGUACC-3'<br>(SEQ ID NO: 18) |
| RNA S3/7 | fragment complementary to S3 spacer | \|\|\|\|\|\|\|\|\|\|\|\|\|\|\|\|\|\|\|\|\|\|\|\|\|\|\|\|\|\|\|\|\|\|\|\|\|\|\|\|\|\|\|  \|\|<br>5'-GGGAUCCCCAAAUAUAAGGUGGAAUAAGUGAACAGAAUUAAACAGUUAC<u>CU</u>AAAAAAAAAAAGGGUACC-3'<br>(SEQ ID NO: 19) |
| RNA S3/15 | | \|\|   \|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>5'-GGGAUCCCCAAAUAUAAGGUGGAUAAAGUGAACAGAAUUAAACAGUUACGAAAAAAAAAAAGGGUACC-3'<br>(SEQ ID NO: 20) |
| RNA S3/9 | | \|\|\|\|\|\|\|\|\|\|\|\|\|\|\|\|   \|\|\|\|\|\|\|\|\|\|\|\|\|\|\|\|\|\|\|\|\|\|\|\|\|<br>5'-GGGAUCCCCAAAUAUAAGGUGGAAUAAGUGAACACUAUUAAACAGUUACGAAAAAAAAAAAGGGUACC-3'<br>(SEQ ID NO: 21) |
| RNA S3/10 | single stranded activator RNA 53-mer containing | \|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>5'-GGGAUCCCCAAAUAUAAGGUGGAAUAAGUGAACAGAAUUAAACAGUUACGAAA-3'<br>(SEQ ID NO: 22) |

TABLE 1-continued

Nucleic acid substrates used *

| | | |
|---|---|---|
| | 32 nt fragment complementary to S3 spacer | |
| RNA S3/14 | single stranded activator RNA 48-mer containing 32 nt fragment complementary to S3 spacer | 5'-GGAAUAAGUGAACAGAAUUAAACAGUUACGAAAAAAAAAAAGGGUACC-3' (SEQ ID NO: 23) |
| RNA NS | single stranded RNA 68-mer lacking the fragment complementary to crRNA | 5'-GGGCGGCAAAUUGAGGAUUUCGUAACUGUUUAAUUCUGUUCACUUAUUCCACCAACAAAAGGUGGCGA-3' (SEQ ID NO: 11) |
| ssRNA NSa | single stranded RNA 84-mer lacking the fragment complementary to crRNA | 5'-GGGUACCGAGCUCGAAUUGAAAUUCUAAACGCUAAAGAGGAAGAGGACAUGGUGAAUUCGUAAUCAUGGUCAUAGCUGUUUCCC-3' (SEQ ID NO: 24) |
| ssRNA NSb | | 5'-GGGAAACAGCUAUGACCAUGAUUACGAAUUCACCAUGUCCUCUUCCUCUUUAGCGUUUAGAAUUUCAAUUCGAGCUCGGUACCC-3' (SEQ ID NO: 25) |
| dsRNA NSa/NSb | double stranded RNA 84 bp duplex lacking the 3'-fragment complementary to crRNA | 5'-GGGUACCGAGCUCGAAUUGAAAUUCUAAACGCUAAAGAGGAAGAGGACAUGGUGAAUUCGUAAUCAUGGUCAUAGCUGUUUCCC-3' (SEQ ID NO: 24)<br>CCCAUGGCUCGAGCUUAACUUUAAGAUUUGCGAUUUCUCCUUCUCCUGUACCACUUAAGCAUUAGUACCAGUAUCGACAAAGGG-5' (SEQ ID NO: 25) |
| ssRNA NSc | single stranded RNA 78-mer lacking the fragment complementary to crRNA | 5'-GGGAAACAGCAUAGCAAGUUAAAAUAAGGCUAGUCCGUUAUCAACUUGAAAAAGUGGCACCGAGUCGGUGCUUUUUUU-3' (SEQ ID NO: 12) |
| ssRNA NSd | single stranded RNA 80-mer lacking the fragment complementary to crRNA | 5'-GGGUAAAUCUUGCAGAAGCUACAAAGAUAAGGCUUCAUGCCGAAAUCAACACCCUGUCAUUUUAUGGCAGGGUGUUUUCG-3' (SEQ ID NO: 13) |
| ssRNA NSe | single stranded RNA 52-mer lacking the fragment complementary to crRNA | 5'-GGGUUUCCCAACCAUCCAGCCUACCGGCCGUCCGACCUGCCUUCCCUUUCCC-3' (SEQ ID NO: 15) |
| ssDNA S3/2 | single stranded oligodeoxynucleotide | 5'-AAATATAAGGTGGAATAAGTGAACAGAATTAAACAGTTACGAAAAAAAAAAA-3' (SEQ ID NO: 26) |

TABLE 1-continued

Nucleic acid substrates used *

52-mer containing 32 nt fragment complementary to S3 spacer

* Above the Table crRNA bound in the StCsm is shown for clarity.

Red and black lettering in crRNA indicates the spacer and 5'-handle sequences, respectively. Bold lettering in the substrates represents protospacer sequence.

The 32-mer fragment in the substrates complementary to S3 spacer of crRNA is colored in bold red. Protospacer 3'-flanking sequence which is complementary to the 5'-handle of crRNA is underlined. Dashes above the sequences of single-stranded RNA and DNA indicate nucleotides which are complementary to the crRNA (shown above the Table). Complementarities in double-stranded RNA are indicated with the dashes between the strands. First 5'-GGG nucleotides (or 5'-GGA in S3/14) were incorporated into RNA during in vitro transcription.

Each of the following references are expressly incorporated by references herein in its entirety.

1. Kazlauskiene et al., *Spatiotemporal Control of Type III-A CRISPR-Cas Immunity: Coupling DNA Degradation with the Target RNA Recognition*. Mol Cell, 2016. 62(2): p. 295-306.
2. Tamulaitis et al., *Programmable RNA shredding by the type III-A CRISPR-Cas system of Streptococcus thermophilus*. Mol Cell, 2014. 56(4): p. 506-17.
3. Fujimoto et al. *Identity of Phosphodiesterase and Phosphomonoesterase Activities with Nuclease P1 (a Nuclease from Penicillium citrinum)*. Agricultural and Biological Chemistry, 1974. 38(4): p. 785-790.
4. Fujimoto et al. *Specificity of Nuclease P1*. Agricultural and Biological Chemistry, 1974. 38(9): p. 1555-1561.
5. Kubota et al., *Identification of 2'-phosphodiesterase, which plays a role in the 2-5A system regulated by interferon*. J Biol Chem, 2004. 279(36): p. 37832-41.
6. Poulsen et al., *Human 2'-phosphodiesterase localizes to the mitochondrial matrix with a putative function in mitochondrial RNA turnover*. Nucleic Acids Res, 2011. 39(9): p. 3754-70.
7. Poulsen et al., *Enzyme assays for synthesis and degradation of 2-5As and other 2'-5' oligonucleotides*. BMC Biochem, 2015. 16: p. 15.
8. Makarova et al., *CARF and WYL domains: ligand-binding regulators of prokaryotic defense systems*. Front Genet, 2014. 5: p. 102.
9. Cao et al., *Identification and functional study of type III-A CRISPR-Cas systems in clinical isolates of Staphylococcus aureus*. Int J Med Microbiol, 2016.
10. Elmore et al., *Bipartite recognition of target RNAs activates DNA cleavage by the Type III-B CRISPR-Cas system*. Genes Dev, 2016. 30(4): p. 447-59.
11. Estrella et al. *RNA-activated DNA cleavage by the Type III-B CRISPR-Cas effector complex*. Genes Dev, 2016. 30(4): p. 460-70.
12. Samai et al., *Co-transcriptional DNA and RNA Cleavage during Type III CRISPR-Cas Immunity*. Cell, 2015. 161(5): p. 1164-74.
13. Goldberg et al., *Conditional tolerance of temperate phages via transcription-dependent CRISPR-Cas targeting*. Nature, 2014. 514(7524): p. 633-7.
14. Liu et al., *RNA and DNA Targeting by a Reconstituted Thermus thermophilus Type III-A CRISPR-Cas System*. PLoS One, 2017. 12(1): p. e0170552.
15. Han et al., *A type III-B CRISPR-Cas effector complex mediating massive target DNA destruction*. Nucleic Acids Res, 2016.
16. Tamulaitis et al. *Type III CRISPR-Cas Immunity: Major Differences Brushed Aside*. Trends Microbiol, 2017. 25(1): p. 49-61.
17. Zhu and Ye, *Crystal structure of Cmr2 suggests a nucleotide cyclase-related enzyme in type Ill CRISPR-Cas systems*. FEBS Lett, 2012. 586(6): p. 939-45.
18. Cocozaki et al., *Structure of the Cmr2 subunit of the CRISPR-Cas RNA silencing complex*. Structure, 2012. 20(3): p. 545-53.
19. Makarova et al., *A DNA repair system specific for thermophilic Archaea and bacteria predicted by genomic context analysis*. Nucleic Acids Res, 2002. 30(2): p. 482-96.
20. Hatoum-Aslan et al., *Genetic characterization of antiplasmid immunity through a type III-A CRISPR-Cas system*. J Bacteriol, 2014. 196(2): p. 310-7.
21. Osawa, T., H. Inanaga, and T. Numata, *Crystal structure of the Cmr2-Cmr3 subcomplex in the CRISPR-Cas RNA silencing effector complex*. J Mol Biol, 2013. 425(20): p. 3811-23.
22. Opoku-Temeng, C., et al., *Cyclic dinucleotide (c-di-GMP, c-di-AMP, and cGAMP) signalings have come of age to be inhibited by small molecules*. Chem Commun (Camb), 2016. 52(60): p. 9327-42.
23. Koonin, E. V. and K. S. Makarova, *CRISPR-Cas: evolution of an RNA-based adaptive immunity system in prokaryotes*. RNA Biol, 2013. 10(5): p. 679-86.
24. Makarova, K. S., et al., *Unification of Cas protein families and a simple scenario for the origin and evolution of CRISPR-Cas systems*. Biol Direct, 2011. 6: p. 38.
25. Makarova, K. S., et al., *A putative RNA-interference-based immune system in prokaryotes: computational analysis of the predicted enzymatic machinery, functional analogies with eukaryotic RNAi, and hypothetical mechanisms of action*. Biol Direct, 2006. 1: p. 7.
26. Makarova, K. S., et al., *Evolution and classification of the CRISPR-Cas systems*. Nat Rev Microbiol, 2011. 9(6): p. 467-77.
27. Wiedenheft, B., S. H. Sternberg, and J. A. Doudna, *RNA-guided genetic silencing systems in bacteria and archaea*. Nature, 2012. 482(7385): p. 331-8.
28. Kim, Y. K., Y. G. Kim, and B. H. Oh, *Crystal structure and nucleic acid-binding activity of the CRISPR-associated protein Csx1 of Pyrococcus furiosus*. Proteins, 2013. 81(2): p. 261-70.

29. Niewoehner, O. and M. Jinek, *Structural basis for the endoribonuclease activity of the type III-A CRISPR-associated protein Csm6*. RNA, 2016. 22(3): p. 318-29.
30. Anantharaman, V., et al., *Comprehensive analysis of the HEPN superfamily: identification of novel roles in intra-genomic conflicts, defense, pathogenesis and RNA processing*. Biol Direct, 2013. 8: p. 15.
31. Jiang, W., P. Samai, and L. A. Marraffini, *Degradation of Phage Transcripts by CRISPR-Associated RNases Enables Type III CRISPR-Cas Immunity*. Cell, 2016. 164(4): p. 710-21.
32. Xiao, T. S. and K. A. Fitzgerald, *The cGAS-STING pathway for DNA sensing*. Mol Cell, 2013. 51(2): p. 135-9.
33. Danilchanka, O. and J. J. Mekalanos, *Cyclic dinucleotides and the innate immune response*. Cell, 2013. 154(5): p. 962-70.
34. Corrigan, R. M. and A. Grundling, *Cyclic di-AMP: another second messenger enters the fray*. Nat Rev Microbiol, 2013. 11(8): p. 513-24.
35. Silverman, R. N., *A scientific journey through the 2-5A/RNase L system*. Cytokine Growth Factor Rev, 2007. 18(5-6): p. 381-8.
36. Gootenberg, J. S., et al., *Nucleic acid detection with CRISPR-Cas13a/C2c2*. Science, 2017.
37. Zheng, L., U. Baumann, and J. L. Reymond, *An efficient one-step site-directed and site-saturation mutagenesis protocol*. Nucleic Acids Res, 2004. 32(14): p. e115.
38. Zhang, B. Z., et al., *An easy-to-use site-directed mutagenesis method with a designed restriction site for convenient and reliable mutant screening*. J Zhejiang Univ Sci B, 2009. 10(6): p. 479-82.
39. Yoshioka, K., *KyPlot—A User-oriented Tool for Statistical Data Analysis and Visualization*. CompStat, 2002. 17(3): p. 425-437.
40. Sheppard et al. *The CRISPR-associated Csx1 protein of Pyrococcus furiosus is an adenosine-specific endoribonuclease*, RNA, 22 (2016) p. 216-224
41. Lintner, N. G., Frankel, K. A., Tsutakawa, S. E., Alsbury, D. L., Copie, V, Young, M. J., Tainer, J. A., Lawrence, C. M., *The structure of the CRISPR-associated protein Csa3 provides insight into the regulation of the CRISPR/Cas system*, 2011.
42. Engl C, Schaefer J, Kotta-Loizou I, Buck M., *Cellular and molecular phenotypes depending upon the RNA repair system RtcAB of Escherichia coli*, 2016
43. Tanaka N, Meineke B, Shuman S., *RtcB, a novel RNA ligase, can catalyze tRNA splicing and HAC1 mRNA splicing in vivo*, 2011
44. Chakravarty A. K., Subbotin R., Chait B. T. and Shuman, S., *RNA ligase RtcB splices 3'-phosphate and 5'-OH ends via covalent RtcB-(histidinyl)-GMP and polynucleotide-(3')pp(5')G intermediates*, 2012
45. Genschik P., Drabikowski, K., and Filipowicz, W., *Characterization of the Escherichia coli RNA 3'-terminal phosphate cyclase and its sigma 54-regulated operon*, 1998.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims.

The invention claimed is:

1. A method for activation and/or regulation of a protein containing a CRISPR-Associated Rossmann Fold (CARF) domain using a cyclic oligoadenylate, selected from the group consisting of c(AMP)3, c(AMP)4, c(AMP)6 and c(dAMP)3, or a linear oligoadenylate, selected from the group consisting of tetraadenylate, tetraadenylate phosphate, tetraadenylate triphosphate, hexaadenylate, hexaadenylate phosphate, hexaadenylate triphosphate and any combinations thereof.

2. The method according to claim 1, wherein the protein containing CARF domain is a ribonuclease, a deoxyribonuclease, a transcriptional activator, DNA-binding protein, a RtcR-like protein or a deaminase.

3. The method according to claim 1, wherein the protein containing a CARF domain is a ribonuclease, and wherein the method is used for the degradation of single stranded ribonucleic acid (ssRNA) in controllable fashion, the method further comprising contacting a biological sample containing ssRNA with said ribonuclease and a cyclic or linear oligoadenylate under conditions resulting in degradation of the ssRNA.

4. The method according to claim 1, wherein the protein containing a CARF domain is a ribonuclease, and wherein the method further comprises cleaving RNA in controllable fashion in vitro by using said ribonuclease and cyclic or linear oligoadenylates.

5. The method according to claim 3, wherein the CARF-containing ribonuclease is selected from Csm6, StCsm6, StCsm6', TtCsm6 or Csx1 or any other ribonuclease containing CARF domain.

6. The method according to claim 1, wherein the protein containing a CARF domain is a deoxyribonuclease, and wherein the method further comprises cleaving DNA in controllable fashion in vitro by using said deoxyribonuclease and cyclic or linear oligoadenylates.

7. The method according to claim 3, wherein the CARF-containing ribonuclease or deoxyribonuclease is inactivated by degrading the cyclic or linear oligoadenylate.

8. A method for activation and/or regulation of a CRISPR-Associated Rossmann Fold (CARF) domain containing proteins in vitro and in vivo, comprising effectively applying cyclic or linear oligoadenylates.

* * * * *

SEQUENCE LISTING

```
<160> NUMBER OF SEQ ID NOS: 26

<210> SEQ ID NO 1
<211> LENGTH: 4
<212> TYPE: PRT
<213> ORGANISM: Streptococcus thermophilus

<400> SEQUENCE: 1

Gly Gly Asp Asp
1

<210> SEQ ID NO 2
<211> LENGTH: 10
<212> TYPE: PRT
<213> ORGANISM: Streptococcus thermophilus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 2

Asp Asn Xaa Ser Thr Xaa Xaa Xaa Arg Lys
1               5                   10

<210> SEQ ID NO 3
<211> LENGTH: 190
<212> TYPE: PRT
<213> ORGANISM: Streptococcus thermophilus
```

```
<400> SEQUENCE: 3

Val Glu Asp Leu Asp Ala Leu Trp Glu Arg Tyr Arg Glu Ala Val Arg
1               5                   10                  15

Ala Gly Gly Asn Pro Gln Ala Leu Tyr Gln Glu Met Val Trp Pro Ala
            20                  25                  30

Leu Leu Ala Leu Trp Arg Glu Lys Pro Arg Val Tyr Pro Phe Pro Gln
        35                  40                  45

Ala Phe Ala Val Ser Val His Thr Leu Gly Thr Ser Pro Glu Ala Thr
    50                  55                  60

Ala Leu Ala Ile Leu Gly Ala Gly Ala Glu Arg Val Tyr Val Leu His
65                  70                  75                  80

Thr Pro Glu Ser Ala Arg Phe Leu Pro Arg Leu Arg Gln Asp Thr Gly
                85                  90                  95

Lys Asp Leu Tyr Pro Val Glu Ile Gly Lys Ser Asp Val Glu Ala Ile
            100                 105                 110

Tyr Arg Glu Val Lys Arg Leu Leu Glu Lys His Pro Glu Val Pro Val
        115                 120                 125

Ala Leu Asp Leu Thr Ser Gly Thr Lys Ala Met Ser Ala Gly Leu Ala
    130                 135                 140

Ala Ala Gly Phe Phe Phe Gln Arg Phe Tyr Pro Lys Val Arg Val Val
145                 150                 155                 160

Tyr Val Asp Asn Glu Asp Tyr Asp Pro Glu Leu Arg Arg Pro Arg Ala
                165                 170                 175

Gly Thr Glu Lys Leu Arg Ile Leu Pro Asn Pro His Glu Ala
            180                 185                 190

<210> SEQ ID NO 4
<211> LENGTH: 180
<212> TYPE: PRT
<213> ORGANISM: Streptococcus thermophilus

<400> SEQUENCE: 4

Met Lys Ile Leu Phe Ser Pro Ile Gly Asn Ser Asp Pro Trp Arg Asn
1               5                   10                  15

Asp Arg Asp Gly Ala Met Leu His Ile Val Arg His Tyr Asn Leu Asp
            20                  25                  30

Lys Val Val Leu Tyr Phe Thr Arg Thr Ile Trp Glu Gly Asn Glu Asn
        35                  40                  45

Arg Lys Gly His Lys Ile Tyr Glu Trp Glu Lys Ile Ile Gln Thr Val
    50                  55                  60

Ser Pro Asn Thr Glu Val Glu Ile Ile Glu Asn Val Asp Asn Ala
65                  70                  75                  80

Gln Asp Tyr Asp Val Phe Lys Glu Lys Phe His Lys Tyr Leu Lys Ile
                85                  90                  95

Ile Glu Asp Ser Tyr Glu Asp Cys Glu Ile Ile Leu Asn Val Thr Ser
            100                 105                 110

Gly Thr Pro Gln Met Glu Ser Thr Leu Cys Leu Glu Tyr Ile Val Tyr
        115                 120                 125

Pro Glu Asn Lys Lys Cys Val Gln Val Ser Thr Pro Thr Lys Asp Ser
    130                 135                 140

Asn Ala Gly Ile Glu Tyr Ser Asn Pro Lys Asp Lys Val Glu Glu Phe
145                 150                 155                 160

Glu Ile Val Asn Glu Val Glu Lys Lys Ser Glu Lys Arg Cys Lys Glu
                165                 170                 175
```

```
Ile Asn Ile Leu
            180

<210> SEQ ID NO 5
<211> LENGTH: 173
<212> TYPE: PRT
<213> ORGANISM: Streptococcus thermophilus

<400> SEQUENCE: 5

Leu Lys Ile Leu Ile Ser Ala Val Gly Thr Thr Asp Pro Ile Ser Asn
1               5                   10                  15

Asn His Asp Ala Ala Leu Leu His Ile Ala Arg Asn Tyr Arg Pro Asp
            20                  25                  30

Lys Ile Val Leu Val Tyr Ser Gln Glu Met Met Val Lys Gln Asp Leu
        35                  40                  45

Ile Asn Lys Val Leu Leu Ser Ile Glu Gly Tyr Asn Pro Ile Ile Glu
    50                  55                  60

Ile Asp Ser Thr Ile Leu Asn Asn Asp Glu Val Phe Leu Phe Asp Lys
65                  70                  75                  80

Met Tyr Glu Val Met Gly Gln Ile Val Gln Lys Tyr Thr Asn Asp Asp
                85                  90                  95

Asn Glu Ile Ile Leu Asn Leu Ser Ser Gly Thr Pro Gln Ile Ile Ser
            100                 105                 110

Ala Leu Phe Ala Leu Asn Arg Ile Asn Asp Tyr Asn Thr Gln Ala Ile
        115                 120                 125

Gln Val Ala Thr Pro Lys Asn Arg Ala Asn Arg Glu Tyr Thr Ala Leu
    130                 135                 140

Thr Glu Ser Glu Ile Asp Ala Leu Ile Met Glu Asn Gln Asp Asn Arg
145                 150                 155                 160

Leu Asp Phe Val Asp Arg Ser Ile Lys Asp Lys Ser Glu
                165                 170

<210> SEQ ID NO 6
<211> LENGTH: 174
<212> TYPE: PRT
<213> ORGANISM: Streptococcus thermophilus

<400> SEQUENCE: 6

Met Arg Val Leu Ile Ser Ala Val Gly Asp Thr Asp Pro Phe Arg Asn
1               5                   10                  15

Phe His Asp Gly Ser Leu Ile His Ile Ala Arg Lys Tyr Arg Pro Glu
            20                  25                  30

Lys Val Ile Leu Ile Phe Ser Glu His Thr Ala Lys Lys Gln Gly Asn
        35                  40                  45

Ile Glu Lys Ala Leu Phe Ser Ile Ala Pro Asn Tyr Glu Pro Glu Leu
    50                  55                  60

Ile Ile His Asp Pro Ile Ile Ser Asp Asn Glu Val His Ile Phe Asp
65                  70                  75                  80

Val Met Phe Gln Arg Phe Ser Asp Ile Leu Gln Glu Tyr Tyr Thr Lys
                85                  90                  95

Glu Asp Glu Phe Ile Leu Asn Leu Ser Ser Ala Thr Pro Gln Ile Lys
            100                 105                 110

Ser Ala Leu Phe Val Ile Asn Arg Leu Asn Gly Ile Asn Val Lys Ala
        115                 120                 125

Val Gln Val Ser Ser Pro Glu His Ala Ser Asn Glu Asn Ile Gly His
    130                 135                 140
```

Asp Asn Asp Glu Asn Ile Asp Glu Leu Ile Glu Val Asn Lys Asp Asn
145                 150                 155                 160

Lys Val Asn Phe Ile Asp Arg Thr Ile Glu Asp Asn Ala Glu
                165                 170

<210> SEQ ID NO 7
<211> LENGTH: 254
<212> TYPE: PRT
<213> ORGANISM: Streptococcus thermophilus

<400> SEQUENCE: 7

Thr Glu Gln Glu Thr Leu Thr Ile Leu Leu Asp Val Tyr Ala Tyr Tyr
1               5                   10                  15

Gln Ala Tyr Gln Ile Val Lys Ala Ser Gln Phe Phe Ser Asp Asp Ile
                20                  25                  30

Ile Phe Leu Leu Glu Leu Leu Lys Glu Arg Arg Glu Leu Asn Val Asp
                35                  40                  45

Phe Leu Phe Gln Asn Gln Val His Leu Gln Glu Leu Glu Leu Thr Tyr
50                  55                  60

His Ile Ser Leu Leu Asp Asn Ala Tyr Glu Glu Leu Leu Ala Asn
65                  70                  75                  80

Tyr Ile Met Asp Leu Glu Ala Lys Leu Arg Asn Asp His Ile Ile Asp
                85                  90                  95

Phe Val Arg Ser Val Ser Pro Ile Leu Tyr Arg Leu Leu Met Arg Leu
                100                 105                 110

Met Gln Ser Gln Val Ala Asp Ile Asn Asp Tyr Ile Tyr Asp Ala Lys
                115                 120                 125

Asn Asp Gln Tyr Asp Thr Trp Lys Phe Asp Lys Met His Asp Ser Ala
130                 135                 140

Asn Pro Phe Val Gln Asn Phe Val Ala Lys Gly Arg Asp Ser Lys Ile
145                 150                 155                 160

Thr Ser Arg Ser Leu Ala Asp Phe Ile Gln Leu Thr Asp Leu Pro Gln
                165                 170                 175

Ala Ile Lys Asp Asn Ile Leu Leu Leu Arg Asp Phe Glu Lys Ser Val
                180                 185                 190

Arg Asn Pro Leu Ala His Leu Ile Lys Pro Phe Asp Glu Glu Leu
                195                 200                 205

His Arg Thr Thr Gly Phe Ser Ser Gln Thr Phe Leu Gly Lys Ile Ile
                210                 215                 220

Gln Leu Ala Val Phe Ser Gly Ile His Tyr Asp Asn Asp Lys Phe Tyr
225                 230                 235                 240

Phe Asp Lys Val Asn Glu Leu Ile Lys Arg Ile Tyr Gln Asn
                245                 250

<210> SEQ ID NO 8
<211> LENGTH: 242
<212> TYPE: PRT
<213> ORGANISM: Streptococcus thermophilus

<400> SEQUENCE: 8

Ser Phe Arg Glu Ala Met Ile Arg Ser Gln Ile Leu Gly Leu Ile Asp
1               5                   10                  15

Asn Tyr Asp Tyr Glu Gly Ala Leu Asn Leu Val Ser Asn Gln Lys Ser
                20                  25                  30

Phe Arg Asn Gly Lys Leu Leu Arg Lys Leu Leu Ser Leu Thr Lys
                35                  40                  45

-continued

```
Gln Ile Lys Thr His Glu Val Phe Pro Glu Ile Asn Glu Lys Tyr Arg
 50                  55                  60

Asp Asp Ala Leu Lys Lys Ser Leu Phe His Tyr Leu Leu Asn Met
 65                  70                  75                  80

Arg Tyr Asn Arg Leu Asp Val Ala Glu Thr Leu Ile Arg Val Lys Ser
                 85                  90                  95

Ile Ala Glu Phe Ile Leu Lys Thr Tyr Ile Glu Ile His Trp Pro Thr
            100                 105                 110

Leu Ile Ile Glu Lys Asp Gly Lys Pro Tyr Leu Asn Asp Glu Asp Asn
            115                 120                 125

Leu Ser Phe Val Tyr Lys Tyr Asn Leu Leu Glu Lys Arg Lys Gln
130                 135                 140

Asn Phe Asp Val Ser Arg Ile Leu Gly Leu Pro Ala Phe Ile Asp Ile
145                 150                 155                 160

Leu Thr Ile Leu Glu Pro Asn Ser Gln Leu Leu Lys Glu Val Asn Ala
                165                 170                 175

Val Asn Asp Ile Asn Gly Leu Arg Asn Ser Ile Ala His Asn Leu Asp
            180                 185                 190

Thr Leu Asn Leu Asp Lys Asn Lys Asn Tyr Lys Lys Ile Met Leu Ser
            195                 200                 205

Val Glu Ala Ile Lys Asn Met Leu His Ile Ser Phe Pro Glu Ile Glu
210                 215                 220

Glu Glu Asp Tyr Asn Tyr Phe Glu Glu Lys Asn Lys Glu Phe Lys Glu
225                 230                 235                 240

Leu Leu

<210> SEQ ID NO 9
<211> LENGTH: 255
<212> TYPE: PRT
<213> ORGANISM: Streptococcus thermophilus

<400> SEQUENCE: 9

Lys Phe Thr Gln Ala Leu Val Lys Arg His Leu Arg Ser Leu Ile Ala
  1               5                  10                  15

Ser Phe Asp Tyr Gln Ala Ala Glu Ala Ile Ile Asn Arg Lys Glu Tyr
                 20                  25                  30

Asn Lys Leu Leu Ser Lys Lys Ile Ala Tyr Ile Arg Glu Lys Leu
             35                  40                  45

Tyr Asp Phe Ser Arg Val Phe Lys Asn Gln Ser Ile Leu Ser Asp Ile
 50                  55                  60

Leu Ser Phe Pro Leu Asp Ser Gln Lys Lys Ala Leu Asn Tyr Tyr
 65                  70                  75                  80

Leu Met Ile Asp Val Leu Lys Glu Arg Glu His Ile Ala Asp Val Leu
                 85                  90                  95

Ile Lys Ala Lys Ser Leu Ala Glu Phe Val Ile Glu Glu Thr Ile Lys
            100                 105                 110

Lys Asp His Glu Gly Leu Ile Val Phe Asp Gly Asn Leu Pro Lys Leu
            115                 120                 125

Asn Pro Ser Phe Pro Asp Cys Glu Ala Ile Leu Asp Asp Ile Asp Lys
130                 135                 140

Lys Met Lys Lys Ser Arg Gly Ile Glu Asp Thr Glu Glu Arg Ile Phe
145                 150                 155                 160

Ser Val Gln Ser Thr Leu Asn Leu Leu Ser Tyr Leu Asn Ile Leu Glu
                165                 170                 175
```

```
Phe Tyr Glu Tyr Asp Ser Gln Leu Gln Thr Ala Ile Asn Gly Ile Leu
            180                 185                 190

Ser Leu Asn Gly Glu Arg Asn Lys Val Ala His Gly Leu Ser Glu Ile
        195                 200                 205

Asp Thr Arg Leu Leu Ser Arg Lys Lys Leu Lys Gln Leu Ser Glu Asn
    210                 215                 220

Leu Arg Leu Leu Leu Val Asp Cys Leu Gly Ile Asp Ser Ser Tyr Phe
225                 230                 235                 240

Asn Tyr Tyr Asp Lys Gln Asn Lys Glu Leu Ile Lys Met Leu Glu
                245                 250                 255

<210> SEQ ID NO 10
<211> LENGTH: 212
<212> TYPE: PRT
<213> ORGANISM: Streptococcus thermophilus

<400> SEQUENCE: 10

Lys Phe Ser Gln Ala Leu Leu Lys Lys Thr Ala Arg Asp Phe Ile Glu
1               5                   10                  15

Lys Phe Asp Tyr Lys Ala Ala Leu Asp Ile Leu Asp Gln Leu Ser Asp
            20                  25                  30

Phe Pro Asn Leu Lys Ser Val Arg Glu Glu Ile Arg Asp Val Val Asn
        35                  40                  45

Cys Leu Ser Lys Gln Asp Val Pro Lys Gly Leu Arg His Lys Lys Leu
    50                  55                  60

Lys Glu Glu Glu Gln Lys Ile Leu Ser Ala Tyr Leu Thr Ile Glu Leu
65                  70                  75                  80

Gln Arg Glu Arg Gly Asn Val Ser Glu Ser Phe Ile Arg Ile Lys Asn
                85                  90                  95

Leu Thr Glu Phe Ile Leu Glu Asp Tyr Ile Glu Lys Arg Tyr Pro Gly
            100                 105                 110

Leu Ile Asp Glu Tyr Cys Glu Asp Ile Gln Lys Tyr Tyr Leu Ser Leu
        115                 120                 125

Phe Asp Tyr Ser Lys Leu Leu Lys Ala Thr Lys Glu Phe Lys Leu Lys
    130                 135                 140

Arg Thr Ile Ala Pro Ile Ile Asp Met Asn Ser Ser Arg Asn Lys Val
145                 150                 155                 160

Ala His Ser Leu Ser Pro Leu Asp Ser Asp Ala Val Lys Gln Leu Gly
                165                 170                 175

Ile Ala Met Lys Thr Leu Lys Thr Leu Val Arg Glu Gln Tyr His Phe
            180                 185                 190

Ser Gln Ser Asp Phe Asn Phe Tyr His Asp Leu Asn Lys Ile Leu Leu
        195                 200                 205

Thr Lys Leu Asn
    210

<210> SEQ ID NO 11
<211> LENGTH: 68
<212> TYPE: RNA
<213> ORGANISM: Artificial Sequence
<220> FEATURE:
<223> OTHER INFORMATION: synthesized

<400> SEQUENCE: 11
gggcggcaaa uugaggauuu cguaacuguu uaauucuguu cacuuauucc accaacaaaa     60
gguggcga                                                              68
```

```
<210> SEQ ID NO 12
<211> LENGTH: 78
<212> TYPE: RNA
<213> ORGANISM: Artificial Sequence
<220> FEATURE:
<223> OTHER INFORMATION: synthesized

<400> SEQUENCE: 12
gggaaacagc auagcaaguu aaaauaaggc uaguccguua ucaacuugaa aaaguggcac      60
cgagucggug cuuuuuuu                                                   78

<210> SEQ ID NO 13
<211> LENGTH: 80
<212> TYPE: RNA
<213> ORGANISM: Artificial Sequence
<220> FEATURE:
<223> OTHER INFORMATION: synthesized

<400> SEQUENCE: 13
ggguaaaucu ugcagaagcu acaaagauaa ggcuucaugc cgaaaucaac acccgucau      60 uuuauggcag gguguuuucg                                                 80

<210> SEQ ID NO 14
<211> LENGTH: 6
<212> TYPE: PRT
<213> ORGANISM: Streptococcus thermophilus
<220> FEATURE:
<221> NAME/KEY: misc_feature
<222> LOCATION: (2)..(5)
<223> OTHER INFORMATION: Xaa can be any naturally occurring amino acid

<400> SEQUENCE: 14

Arg Xaa Xaa Xaa Xaa His
1               5

<210> SEQ ID NO 15
<211> LENGTH: 52
<212> TYPE: RNA
<213> ORGANISM: Artificial Sequence
<220> FEATURE:
<223> OTHER INFORMATION: synthesized

<400> SEQUENCE: 15
ggguuuccca accauccagc cuaccggccg uccgaccugc cuucccuuuc cc             52

<210> SEQ ID NO 16
<211> LENGTH: 40
<212> TYPE: RNA
<213> ORGANISM: Streptococcus thermophilus

<400> SEQUENCE: 16
cuuauucacu ugucuuaauu ugucaaugcu uucaaaggca                           40

<210> SEQ ID NO 17
<211> LENGTH: 68
<212> TYPE: RNA
<213> ORGANISM: Artificial Sequence
<220> FEATURE:
<223> OTHER INFORMATION: synthesized

<400> SEQUENCE: 17
gggaucccca aauauaaggu ggaauaagug aacagaauua aacaguuacg aaaaaaaaaa     60
aggguacc                                                              68
```

```
<210> SEQ ID NO 18
<211> LENGTH: 68
<212> TYPE: RNA
<213> ORGANISM: Artificial Sequence
<220> FEATURE:
<223> OTHER INFORMATION: synthesized

<400> SEQUENCE: 18
gggaucccca aauauaaggu ggauaaagug aacagaauua aacaguuacg aaaguuuccg    60
uggguacc                                                            68

<210> SEQ ID NO 19
<211> LENGTH: 68
<212> TYPE: RNA
<213> ORGANISM: Artificial Sequence
<220> FEATURE:
<223> OTHER INFORMATION: synthesized

<400> SEQUENCE: 19 gggauccca aauauaaggu ggauaaagug aacagaauua aacaguuacc uaaaaaaaaa    60
aggguacc                                                            68

<210> SEQ ID NO 20
<211> LENGTH: 68
<212> TYPE: RNA
<213> ORGANISM: Artificial Sequence
<220> FEATURE:
<223> OTHER INFORMATION: RNA S3/15

<400> SEQUENCE: 20
gggaucccca aauauaaggu ggauaaagug aacagaauua aacaguuacg aaaaaaaaaa    60
aggguacc                                                            68

<210> SEQ ID NO 21
<211> LENGTH: 68
<212> TYPE: RNA
<213> ORGANISM: Artificial Sequence
<220> FEATURE:
<223> OTHER INFORMATION: synthesized

<400> SEQUENCE: 21
gggaucccca aauauaaggu ggauaaagug aacacuauua aacaguuacg aaaaaaaaaa    60
aggguacc                                                            68

<210> SEQ ID NO 22
<211> LENGTH: 53
<212> TYPE: RNA
<213> ORGANISM: Artificial Sequence
<220> FEATURE:
<223> OTHER INFORMATION: synthesized

<400> SEQUENCE: 22
gggaucccca aauauaaggu ggauaaagug aacagaauua aacaguuacg aaa          53

<210> SEQ ID NO 23
<211> LENGTH: 48
<212> TYPE: RNA
<213> ORGANISM: Artificial Sequence
<220> FEATURE:
<223> OTHER INFORMATION: synthesized

<400> SEQUENCE: 23
ggaauaagug aacagaauua aacaguuacg aaaaaaaaaa aggguacc                48
```

```
<210> SEQ ID NO 24
<211> LENGTH: 84
<212> TYPE: RNA
<213> ORGANISM: Artificial Sequence
<220> FEATURE:
<223> OTHER INFORMATION: synthesized

<400> SEQUENCE: 24
ggguaccgag cucgaauuga aauucuaaac gcuaaagagg aagaggacau ggugaauucg      60
uaaucauggu cauagcuguu uccc                                            84

<210> SEQ ID NO 25
<211> LENGTH: 84
<212> TYPE: RNA
<213> ORGANISM: Artificial Sequence
<220> FEATURE:
<223> OTHER INFORMATION: synthesized

<400> SEQUENCE: 25
gggaaacagc uaugaccaug auuacgaauu caccaugucc ucuuccucuu uagcguuuag      60
aauuucaauu cgagcucggu accc                                            84

<210> SEQ ID NO 26
<211> LENGTH: 52
<212> TYPE: DNA
<213> ORGANISM: Artificial Sequence
<220> FEATURE:
<223> OTHER INFORMATION: synthesized

<400> SEQUENCE: 26
aaatataagg tggaataagt gaacagaatt aaacagttac gaaaaaaaaa aa              52
```